United States Patent [19]
Janjic et al.

[11] Patent Number: 5,459,015
[45] Date of Patent: Oct. 17, 1995

[54] HIGH-AFFINITY RNA LIGANDS OF BASIC FIBROBLAST GROWTH FACTOR

[75] Inventors: Nebojsa Janjic; Larry Gold, both of Boulder, Colo.

[73] Assignee: NeXstar Pharmaceuticals, Inc., Boulder, Colo.

[21] Appl. No.: 195,005

[22] Filed: Feb. 10, 1994

Related U.S. Application Data

[63] Continuation-in-part of Ser. No. 61,691, Apr. 22, 1993, and Ser. No. 714,131, Jun. 10, 1991, which is a continuation-in-part of Ser. No. 536,428, Jun. 11, 1990, abandoned.

[51] Int. Cl.$^6$ .............................. C12Q 1/68; C12P 19/34
[52] U.S. Cl. .................. 435/6; 435/91.2; 935/77; 935/78
[58] Field of Search .......................... 435/6, 91.2

[56] References Cited

U.S. PATENT DOCUMENTS

| | | | |
|---|---|---|---|
| 5,118,672 | 6/1992 | Schinazi | 514/47 |
| 5,270,163 | 12/1993 | Gold et al. | 435/6 |

FOREIGN PATENT DOCUMENTS

WO92/03568  3/1992  WIPO.

OTHER PUBLICATIONS

Bock et al., Nature 355:564–566 (6 Feb. 1992).
Koch et al., Science 258:1798–1801 (11 Dec. 1992).
Tuerk et al., Science 249:505–510 (3 Aug. 1990).
Carey et al. (1983) Biochemistry 22:2601.
Uhlenbeck et al. (1983) J. Biomol. Structure Dynamics 1:539.
Witherell and Uhlenbeck (1989) Biochemistry 28:71.
Joyce (1989) in *RNA: Catalysis, Splicing, Evolution*, Belfort and Shub (eds.), Elsevier, Amsterdam pp. 83–87.
Robertson and Joyce (1990) Nature 344:467.
Romaniuk et al. (1987) Biochemistry 26:1563.
Kramer et al. (1974) J. Mol. Biol. 89:719.
Bass and Cech (1984) Nature 308:820.
Yarus (1988) Science 240:1751.
Rich et al. (1984) Ann. Rev. Biochem. 53:791.
Schimmel (1989) Cell 58:9.
Tuerk et al. (1988) Proc. Natl. Acad. Sci. USA 85:1364.
Mills et al. (1967) Proc. Natl. Acad. Sci. USA 58:217.
Levisohn and Spiegelman (1968) Proc. Natl. Acad. Sci. USA 60:866.
Levisohn and Spiegelman (1969) Proc. Natl. Acad. Sci. USA 63:805.
Baird and Bohlen (1991) in *Peptide Growth Factors and Their Receptors* (Sporn, M. B. and Roberts, A. B., Eds) pp. 369–418, Springer, N.Y.: Fibroblast Growth Factors.
Jaye et al. (1986) Science 233:541.
Abraham et al. (1986) Science 233:545.
Moore et al. (1986) Embo J. 5:919.
Delli Bovi et al. (1987) Cell 50:729.
Taira et al. (1987) Proc. Natl. Acad. Sci. USA 84:2980.
Zhan et al. (1988) Mol. Cell. Biol. 8:3487.
Marics et al. (1988) Oncogene 4:335.
Finch et al. (1989) Science 245:752.
Presta et al. (1986) Mol. Cell. Biol. 6:4060.
Moscatelli et al. (1986) Proc. Natl. Acad. Sci. USA 83:2091.
Folkman and Klagsbrun (1987) Science 235:442.
Gospodarowicz (1991) Cell Biology Reviews 25:307.
Zhang et al. (1991) Proc. Natl. Acad. Sci. USA 88:3446.
Eriksson et al. (1991) Proc. Natl. Acad. Sci. USA 88:3441.
Ago et al. (1991) J. Biochem. 110:360.
Zhu et al. (1991) Science 251:90.
Reidy et al. (1992) Circulation, Suppl. III 86:III–43.
Takahashi et al. (1990) Proc. Natl. Acad. Sci. USA 87:5710.
Middaugh et al. (1992) Biochemistry 31:9016.

(List continued on next page.)

*Primary Examiner*—Stephanie W. Zitomer
*Attorney, Agent, or Firm*—Swanson & Bratschun

[57] ABSTRACT

Methods are described for the identification and preparation of nucleic acid ligands and ligand solutions to basic fibroblast growth factor (bFGF). Included in the invention are nucleic acid ligands to bFGF which are inhibitors of bFGF and 2'-amino-modified RNA ligands to bFGF.

6 Claims, 12 Drawing Sheets

OTHER PUBLICATIONS

Folkman et al. (1983) Science 221:719.
Crum et al. (1985) Science 230:1375.
Hobbs et al. (1973) Biochem. 12:5138.
Guschlbauer et al. (1977) Nucleic Acids Res. 4:1933.
Shibahara et al. (1987) Nucleic Acids Res. 15:4403.
Pieken et al. (1991) Science 253:314.
Tuerk et al. (1992) Proc. Natl. Acad. Sci. USA 89:6988.
Yarus and Berg (1970) Anal. Biochem. 35:450.
Lowary and Uhlenbeck (1987) Nucleic Acids Res. 15:10483.
Schneider et al. (1992) J. Mol. Biol. 228:862.
Irvine et al. (1991) J. Mol. Biol. 222:739.
Jellinek et al. (1993) Proc. Natl. Acad. Sci. USA 90:11227.
Tuerk et al. (1990) J. Mol. Biol. 213:749.
Gimbrone et al. (1974) JNCI 52:413.
Langer and Folkman (1976) Nature 263:797.
Polverini et al. (1977) Nature 269:804.
Moscatelli (1987) J. Cell. Physiol. 131:123.
Rifkin and Moscatelli (1989) J. Cell. Biol. 109:1.
Basilico and Moscatelli (1992) Adv. Cancer Research 59:115.
Mignatti et al. (1989) J. Cell. Biol. 108:671.
Vlodavsky et al. (1991) Trends Biol. Sci. 16:268.
Mignatti and Rifkin (1991) J. Cell. Biochem. 47:201.
Ueno et al. (1992) J. Biol. Chem. 267:1470.
Armstrong et al. (1992) Cancer Research 52:2004.
Yayon et al. (1991) Cell 64:841.
Rapraeger et al. (1991) Science 252:1705.
Nugent and Edelman (1992) Biochemistry 31:8876.
Halaban et al. (1991) Ann. N.Y. Acad. Sci. 638:232.
Fujimoto et al. (1991) Biochem. Biophys. Res. Commun. 180:386.
Hori et al. (1991) Cancer Res. 51:6180.
Ishai–Michaeli et al. (1992) Biochemistry 31:2080.
Turnbull et al. (1992) J. Biol. Chem. 267:10337.
Roghani and Moscatelli (1992) J. Biol. Chem. 267:22156.
Saffhill et al. (1970) J. Mol. Biol. 51:531.
Kacian et al (1972) Proc. Natl. Acad. Sci. USA 69:3038.
Mills et al. (1973) Science 180:916.

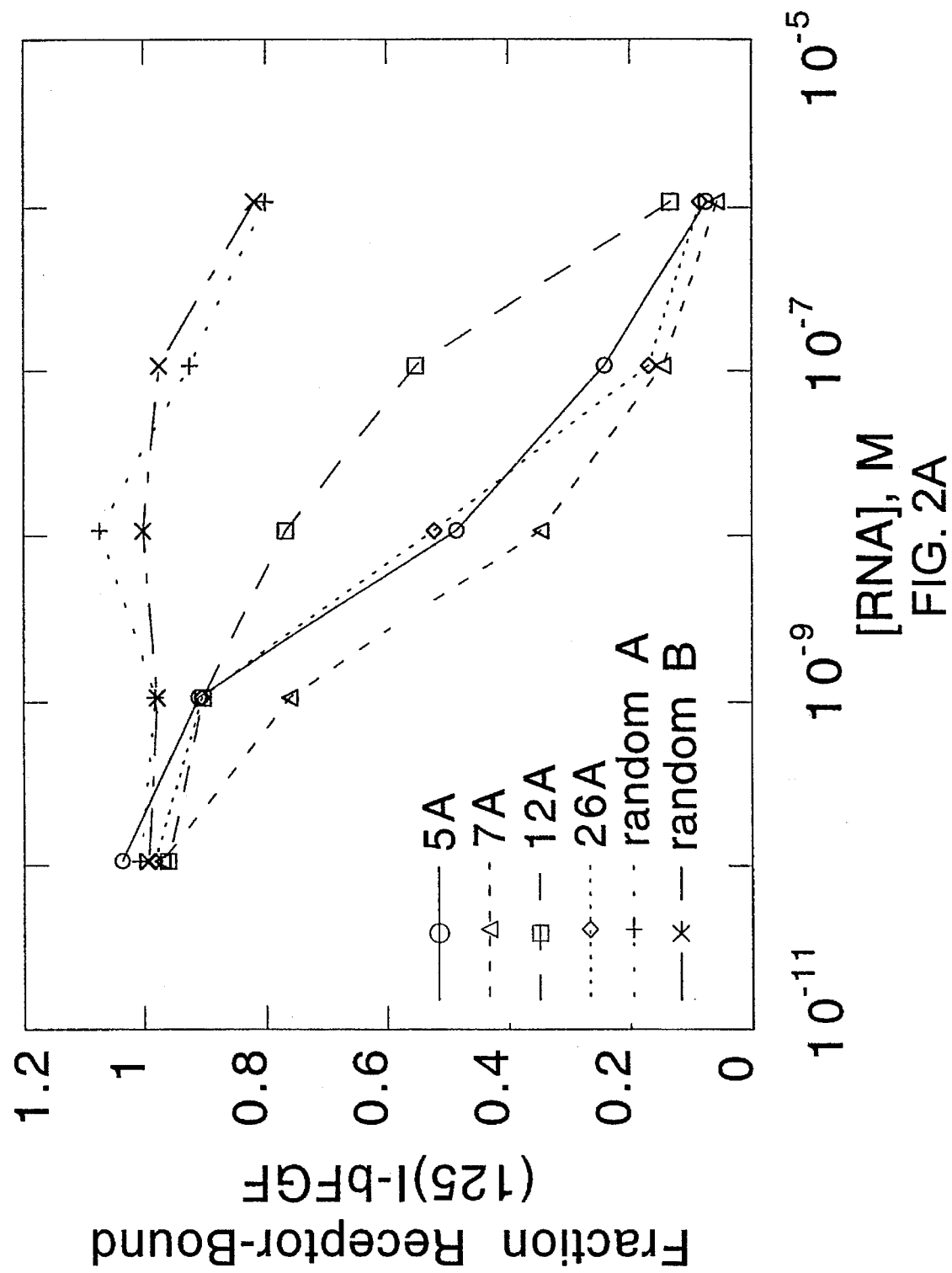

FIGURE 4

| | | SEQ ID NO. |
|---|---|---|
| 4A | gggagcucagaauaaacgcucaaUGCUAUUCGCCUAACUCGGCGCUCCUACCUuucgacaugaggcccgauccggc | 189 |
| 5A | gggagcucagaauaaacgcucaaAUCUCCCCGUCGAAGCUAACCUGGCCACuucgacaugaggcccgauccggc | 190 |
| 7A | gggagcucagaauaaacgcucaaUCGGCGAGCUAACCAAGACACUCGCAcuucgacaugaggcccggauccggc | 191 |
| 10A | gggagcucagaauaaacgcucaaGUAGCACUAUCGGCCUAACCCGGUAGCUCcuucgacaugaggcccgauccggc | 192 |
| 13A | gggagcucagaauaaacgcucaaACCCGGCCUCCGAAGCUAACCAGGACACuucgacaugaggcccgauccggc | 193 |
| 14A | gggagcucagaauaaacgcucaaUGGGUGCUAACCAGGACACACCGCUGUuucgacaugaggcccgauccggc | 194 |
| 16A | gggagcucagaauaaacgcucaaCACGCACUGCCACUGUCCCuucgacaugaggcccgauccggc | 195 |
| 18A | gggagcucagaauaaacgcucaaCUGCGUGGUAUAACCACAUGCCCGGCGAuucgacaugaggcccgauccggc | 196 |
| 21A | gggagcucagaauaaacgcucaaUGGGUGCUAACCAGGCCACACCCUGCUGUuucgacaugaggcccgauccggc | 197 |
| 25A | gggagcucagaauaaacgcucaaCUAGGUGCUAUCCAGGACACUCUCCUGGUCCuucgacaugaggcccgauccggc | 198 |
| 29A | gggagcucagaauaaacgcucaaUGCUAUUCGCCUAGCUCGGCGCUCCUACCUuucgacaugaggcccgauccggc | 199 |
| 38A | gggagcucagaauaaacgcucaaAGCUAUUCGCCUGGCGCGCUCCCCGACCuucgacaugaggcccgauccggc | 200 |
| 39A | gggagcucagaauaaacgcucaaACCAGCUGCGUGCAACCGCACAUGCCUGGuucgacaugaggcccgauccggc | 201 |
| 56A | gggagcucagaauaaacgcucaaCAGGCCCCGUCGUAAGCUAACCUGGACCCuucgacaugaggcccgauccggc | 202 |
| 61A | gggagcucagaauaaacgcucaaUGGGUGCUAACCACCACCACACUCACGCUGUuucgacaugaggcccgauccggc | 227 |

FIGURE 5

| | Sequence | SEQ ID NO. |
|---|---|---|
| 11A | gggagcucagaauaaacgcucaaGGGUAACGUUGU--GACAAGUACACCUGCGUCuucgacaugaggcccggauccggc | 203 |
| 12A | gggagcucagaauaaacgcucaaGGGGCAACGUCACA-GACAAGUCACCCAACuucgacaugaggcccggauccggc | 204 |
| 26A | gggagcucagaauaaacgcucaaCGUCAGAAGGCAACGUAUA--GGCAAGCACACuucgacaugaggcccggauccggc | 205 |
| 27A | gggagcucagaauaaacgcucaaCCUCUCGAAGACAACGCUGU--GACAAGA-CACuucgacaugaggcccggauccggc | 206 |
| 47A | gggagcucagaauaaacgcucaaAGUGGGAAACGCUACUUGACAAGA-CACCACuucgacaugaggcccggauccggc | 207 |
| 65A | gggagcucagaauaaacgcucaaGGCUACGCUAAU-GACAAGUGCACUUGGGUGuucgacaugaggcccggauccggc | 208 |
| 1B | gggagaugccugucgagcaugcugCUCUGGUAACGCAAU--GUCAAGUGCACAUGAguagcuaaacagcuuugucgacggg | 209 |
| 2B | gggagaugccugucgagcaugcugAGCCGCAGGUAACGGACC--GGCGAGACCAUuguagcuaaacagcuuugucgacggg | 210 |
| 6B | gggagaugccugucgagcaugcugACGAGCUUCGUAACGCUAUC-GACAAGUGCAguagcuaaacagcuuugucgacggg | 211 |
| 8B | gggagaugccugucgagcaugcugAAGGGAAACGGUAACGUUGA--GUCCGGUACACCCUGguagcuaaacagcuuugucgacggg | 212 |
| 9B | gggagaugccugucgagcaugcugAGGGUAACGUACU--GGCAAGCUCACACUCCAGCguagcuaaacagcuuugucgacggg | 213 |
| 11B | gggagaugccugucgagcaugcugGAGGUAACGUAC---GACAAGACCACUCCAACUguagcuaaacagcuuugucgacggg | 214 |
| 12B | gggagaugccugucgagcaugcugAGGUAACGUCGA--GUCAAGUGCACUCGACAUguagcuaaacagcuuugucgacggg | 215 |
| 13B | gggagaugccugucgagcaugcugGGGAAACGCUAUC-GACGAGUGCACCCGGCAguagcuaaacagcuuugucgacggg | 216 |
| 14B | gggagaugccugucgagcaugcugGGGUAACGUUGG--GUCAAGCACACCUUCguagcuaaacagcuuugucgacggg | 217 |
| 15B | gggagaugccugucgagcaugcugUCGGGGUAACGUAUU--GGCAAGG-CACCCGACguagcuaaacagcuuugucgacggg | 218 |

FIGURE 5 (cont'd)

```
19B  gggagaugccugucgagcaugcugGGUAACGCCUGUG-GACAAGUGCACCAGCUGCguagcuaaacagcuuugucgacggg   219
22B  gggagaugccugucgagcaugcugAGGGUAACGUACU--GGCAAGCUCACCUCAGCguagcuaaacagcuuugucgacggg   220
28B  gggagaugccugucgagcaugcugAGGGUAACGUAUA--GUCAAGA-CACCUCAAGUguagcuaaacagcuuugucgacggg   221
29B  gggagaugccugucgagcaugcugGGGUAACGCAUU--GGCAAGA-CACCCAGCCCguagcuaaacagcuuugucgacggg   222
36B  gggagaugccugucgagcaugcugGAGGAAACGUACC--GUCGAGC-CACUCCAUGCguagcuaaacagcuuugucgacggg   223
38B  gggagaugccugucgagcaugcugAGGUAACGCUGA--GUCAAGUGCACUCGACAUguagcuaaacagcuuugucgacggg   224
48B  gggagaugccugucgagcaugcugGGGUAACGUGU---GACAAGAUCACCCAGUUUGguagcuaaacagcuuugucgacggg   225
49B  gggagaugccugucgagcaugcugCACAGGGCAACGCUGCU-GACAAGUGCACCUguagcuaaacagcuuugucgacggg    226
```

FIGURE 7

SELEX Experiment A

Starting RNA:

5'-GGGAGACAAGAAUAACGCUCAA [-30N-] UUCGACAGGAGGCUCACAACAGGC-3'
(SEQ ID NO:95)

PCR Primer 1:

5'-<u>TAATACGACTCACTATAG</u>GGAGACAAGAAUAACGCUCAA-3'
        T7 Promoter
(SEQ ID NO:96)

PCR Primer 2:

5'-GCCTGTTGTGAGCCTCCTGTCGAA-3'
(SEQ ID NO:97)

SELEX Experiment B

Starting RNA:

5'-GGGAGGACGAUGCGG [-50N-] CAGACGACTCGCCCGA-3'
(SEQ ID NO:98)

PCR Primer 1:

5'-<u>TAATACGACTCACTATAG</u>GGAGGACGAUGCGG-3'
        T7 Promoter
(SEQ ID NO:99)

PCR Primer 2:

5'-TCGGGCGAGTCGTCTG-3'
(SEQ ID NO:100)

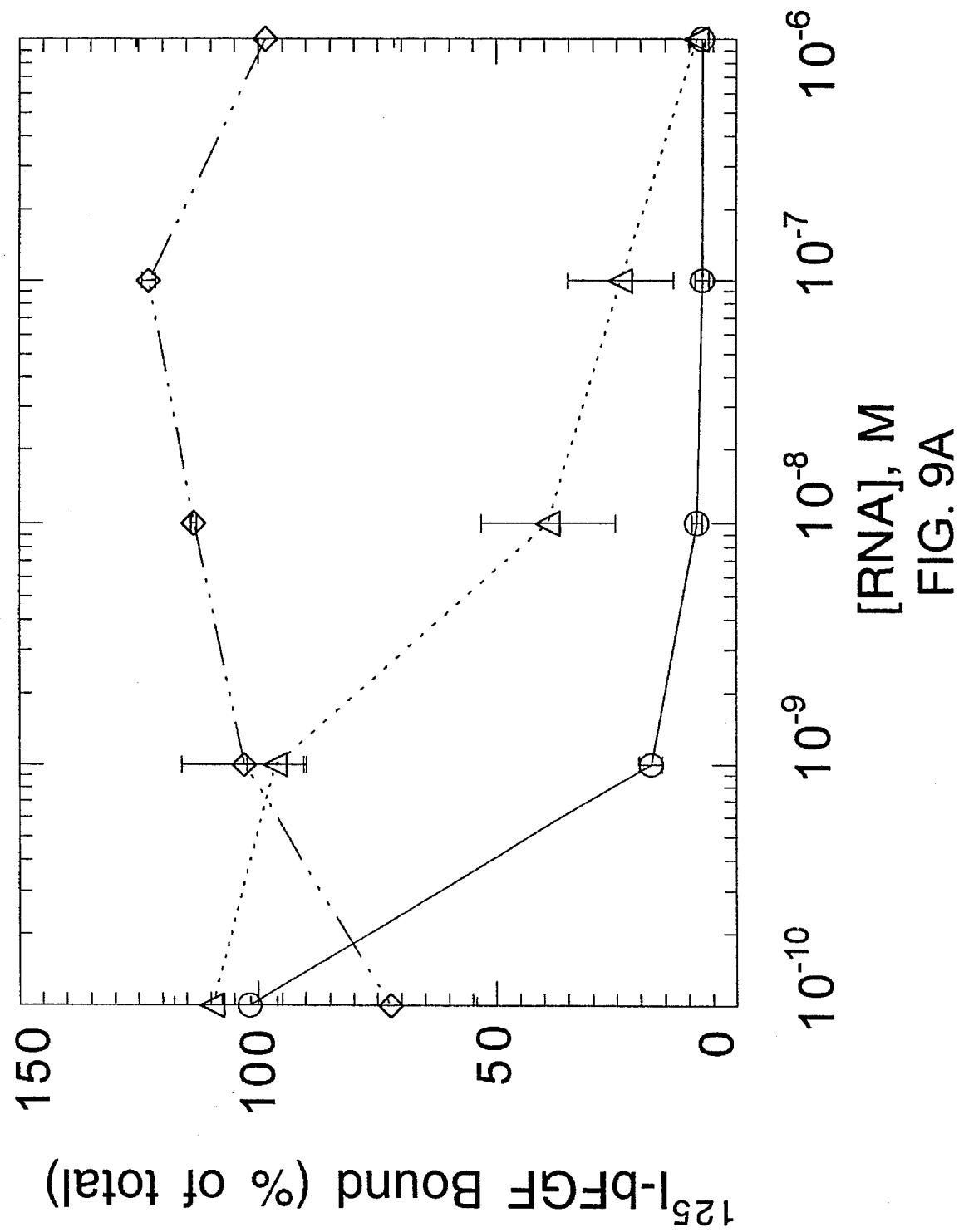

HIGH-AFFINITY RNA LIGANDS OF BASIC FIBROBLAST GROWTH FACTOR

This application is a Continuation-in-Part of U.S. patent application Ser. No. 08/061,691, filed Apr. 22, 1993, entitled High-Affinity RNA Ligands of Basic Fibroblast Growth Factor, and U.S. patent application Ser. No. 07/714,131, filed Jun. 10, 1991, entitled Nucleic Acid Ligands which is a Continuation-in-Part of U.S. patent application Ser. No. 07/536,428, filed Jun. 11, 1990, entitled Systematic Evolution of Ligands by Exponential Enrichment, now abandoned.

FIELD OF THE INVENTION

Described herein are methods for identifying and preparing high-affinity RNA ligands to basic fibroblast growth factor (bFGF). The method utilized herein for identifying such RNA ligands is called SELEX, an acronym for Systematic Evolution of Ligands by EXponential enrichment. This invention includes high-affinity RNA ligand inhibitors of bFGF. Further included within the scope of this invention are modified RNA ligands and mimetic ligands that are informed by the RNA ligands identified herein. Specifically disclosed are 2'-amino (2'-$NH_2$) modified RNA ligands to bFGF. 2'-$NH_2$-modified RNA ligands to bFGF were identified which inhibited the biological activity of bFGF both in vivo and in vitro.

BACKGROUND OF THE INVENTION

Most proteins or small molecules are not known to specifically bind to nucleic acids. The known protein exceptions are those regulatory proteins such as repressors, polymerases, activators and the like which function in a living cell to bring about the transfer of genetic information encoded in the nucleic acids into cellular structures and the replication of the genetic material. Furthermore, small molecules such as GTP bind to some intron RNAs.

Living matter has evolved to limit the function of nucleic acids to a largely informational role. The Central Dogma, as postulated by Crick, both originally and in expanded form, proposes that nucleic acids (either RNA or DNA) can serve as templates for the synthesis of other nucleic acids through replicative processes that "read" the information in a template nucleic acid and thus yield complementary nucleic acids. All of the experimental paradigms for genetics and gene expression depend on these properties of nucleic acids: in essence, double-stranded nucleic acids are informationally redundant because of the chemical concept of base pairs and because replicative processes are able to use that base pairing in a relatively error-free manner.

The individual components of proteins, the twenty natural amino acids, possess sufficient chemical differences and activities to provide an enormous breadth of activities for both binding and catalysis. Nucleic acids, however, are thought to have narrower chemical possibilities than proteins, but to have an informational role that allows genetic information to be passed from virus to virus, cell to cell, and organism to organism. In this context nucleic acid components, the nucleotides, possess only pairs of surfaces that allow informational redundancy within a Watson-Crick base pair. Nucleic acid components need not possess chemical differences and activities sufficient for either a wide range of binding or catalysis.

However, some nucleic acids found in nature do participate in binding to certain target molecules and even a few instances of catalysis have been reported. The range of activities of this kind is narrow compared to proteins and more specifically antibodies. For example, where nucleic acids are known to bind to some protein targets with high affinity and specificity, the binding depends on the exact sequences of nucleotides that comprise the DNA or RNA ligand. Thus, short double-stranded DNA sequences are known to bind to target proteins that repress or activate transcription in both prokaryotes and eukaryotes. Other short double-stranded DNA sequences are known to bind to restriction endonucleases, protein targets that can be selected with high affinity and specificity. Other short DNA sequences serve as centromeres and telomeres on chromosomes, presumably by creating ligands for the binding of specific proteins that participate in chromosome mechanics. Thus, double-stranded DNA has a well-known capacity to bind within the nooks and crannies of target proteins whose functions are directed to DNA binding. Single-stranded DNA can also bind to some proteins with high affinity and specificity, although the number of examples is rather smaller. From the known examples of double-stranded DNA binding proteins, it has become possible to describe some of the binding interactions as involving various protein motifs projecting amino acid side chains into the major groove of B form double-stranded DNA, providing the sequence inspection that allows specificity.

Double-stranded RNA occasionally serves as a ligand for certain proteins, for example, the endonuclease RNase III from E. coli. There are more known instances of target proteins that bind to single-stranded RNA ligands, although in these cases the single-stranded RNA often forms a complex three-dimensional shape that includes local regions of intramolecular double-strandedness. The amino-acyl tRNA synthetases bind tightly to tRNA molecules with high specificity. A short region within the genomes of RNA viruses binds tightly and with high specificity to the viral coat proteins. A short sequence of RNA binds to the bacteriophage T4-encoded DNA polymerase, again with high affinity and specificity. Thus, it is possible to find RNA and DNA ligands, either double- or single-stranded, serving as binding partners for specific protein targets. Most known DNA binding proteins bind specifically to double-stranded DNA, while most RNA binding proteins recognize single-stranded RNA. This statistical bias in the literature no doubt reflects the present biosphere's statistical predisposition to use DNA as a double-stranded genome and RNA as a single-stranded entity in the roles RNA plays beyond serving as a genome. Chemically there is no strong reason to dismiss single-stranded DNA as a fully able partner for specific protein interactions.

RNA and DNA have also been found to bind to smaller target molecules. Double-stranded DNA binds to various antibiotics, such as actinomycin D. A specific single-stranded RNA binds to the antibiotic thiostreptone; specific RNA sequences and structures probably bind to certain other antibiotics, especially those whose function is to inactivate ribosomes in a target organism. A family of evolutionary related RNAs binds with specificity and decent affinity to nucleotides and nucleosides (Bass, B. and Cech, T. (1984) Nature 308:820–826) as well as to one of the twenty amino acids (Yarus, M. (1988) Science 240:1751–1758). Catalytic RNAs are now known as well, although these molecules perform over a narrow range of chemical possibilities, which are thus far related largely to phosphodiester transfer reactions and hydrolysis of nucleic acids.

Despite these known instances, the great majority of proteins and other cellular components are thought not to bind to nucleic acids under physiological conditions and such binding as may be observed is non-specific. Either the capacity of nucleic acids to bind other compounds is limited to the relatively few instances enumerated supra, or the chemical repertoire of the nucleic acids for specific binding is avoided (selected against) in the structures that occur naturally. The present invention is premised on the inventors' fundamental insight that nucleic acids as chemical compounds can form a virtually limitless array of shapes, sizes and configurations, and are capable of a far broader repertoire of binding and catalytic functions than those displayed in biological systems.

The chemical interactions have been explored in cases of certain known instances of protein-nucleic acid binding. For example, the size and sequence of the RNA site of bacteriophage R17 coat protein binding has been identified by Uhlenbeck and coworkers. The minimal natural RNA binding site (21 bases long) for the R17 coat protein was determined by subjecting variable-sized labeled fragments of the mRNA to nitrocellulose filter binding assays in which protein-RNA fragment complexes remain bound to the filter (Carey et al. (1983) Biochemistry 22:2601). A number of sequence variants of the minimal R17 coat protein binding site were created in vitro in order to determine the contributions of individual nucleic acids to protein binding (Uhlenbeck et al. (1983) J. Biomol. Structure Dynamics 1:539 and Romaniuk et al. (1987) Biochemistry 26:1563). It was found that the maintenance of the hairpin loop structure of the binding site was essential for protein binding but, in addition, that nucleotide substitutions at most of the single-stranded residues in the binding site, including a bulged nucleotide in the hairpin stem, significantly affected binding. In similar studies, the binding of bacteriophage Qβ coat protein to its translational operator was examined (Witherell and Uhlenbeck (1989) Biochemistry 28:71). The Qβ coat protein RNA binding site was found to be similar to that of R17 in size, and in predicted secondary structure, in that it comprised about 20 bases with an 8 base pair hairpin structure which included a bulged nucleotide and a 3 base loop. In contrast to the R17 coat protein binding site, only one of the single-stranded residues of the loop is essential for binding and the presence of the bulged nucleotide is not required. The protein-RNA binding interactions involved in translational regulation display significant specificity.

Nucleic acids are known to form secondary and tertiary structures in solution. The double-stranded forms of DNA include the so-called B double-helical form, Z-DNA and superhelical twists (Rich, A. et al. (1984) Ann. Rev. Biochem. 53:791–846). Single-stranded RNA forms localized regions of secondary structure such as hairpin loops and pseudoknot structures (Schimmel, P. (1989) Cell 58:9–12). However, little is known concerning the effects of unpaired loop nucleotides on stability of loop structure, kinetics of formation and denaturation, thermodynamics, and almost nothing is known of tertiary structures and three dimensional shape, nor of the kinetics and thermodynamics of tertiary folding in nucleic acids (Tuerk, C. et al. (1988) Proc. Natl. Acad. Sci. U.S.A. 85:1364–1368).

A type of in vitro evolution was reported in replication of the RNA bacteriophage Qβ. Mills, D. R. et al. (1967) Proc. Natl. Acad. Sci U.S.A. 58:217–224; Levisohn, R. and Spiegelman, S. (1968) Proc. Natl. Acad. Sci. U.S.A. 60:866–872; Levisohn, R. and Spiegelman S. (1969) Proc. Natl. Acad. Sci. U.S.A. 63:805–811; Saffhill, R. et al. (1970) J. Mol. Biol. 51:531–539; Kacian, D. L. et al. (1972) Proc. Natl. Acad. Sci. U.S.A. 69:3038–3042; Mills, D. R. et al. (1973) Science 180:916–927. The phage RNA serves as a poly-cistronic messenger RNA directing translation of phage-specific proteins and also as a template for its own replication catalyzed by Qβ RNA replicase. This RNA replicase was shown to be highly specific for its own RNA templates. During the course of cycles of replication in vitro small variant RNAs were isolated which were also replicated by Qβ replicase. Minor alterations in the conditions under which cycles of replication were performed were found to result in the accumulation of different RNAs, presumably because their replication was favored under the altered conditions. In these experiments, the selected RNA had to be bound efficiently by the replicase to initiate replication and had to serve as a kinetically favored template during elongation of RNA. Kramer et al. (1974) J. Mol. Biol. 89:719 reported the isolation of a mutant RNA template of Qβ replicase, the replication of which was more resistant to inhibition by ethidium bromide than the natural template. It was suggested that this mutant was not present in the initial RNA population but was generated by sequential mutation during cycles of in vitro replication with Qβ replicase. The only source of variation during selection was the intrinsic error rate during elongation by Qβ replicase. In these studies what was termed "selection" occurred by preferential amplification of one or more of a limited number of spontaneous variants of an initially homogenous RNA sequence. There was no selection of a desired result, only that which was intrinsic to the mode of action of Qβ replicase.

Joyce and Robertson (Joyce (1989) in *RNA: Catalysis, Splicing., Evolution,* Belfort and Shub (eds.), Elsevier, Amsterdam pp. 83–87; and Robertson and Joyce (1990) Nature 344:467) reported a method for identifying RNAs which specifically cleave single-stranded DNA. The selection for catalytic activity was based on the ability of the ribozyme to catalyze the cleavage of a substrate ssRNA or DNA at a specific position and transfer the 3'-end of the substrate to the 3'-end of the ribozyme. The product of the desired reaction was selected by using a deoxyoligonucleotide primer which could bind only to the completed product across the junction formed by the catalytic reaction and allowed selective reverse transcription of the ribozyme sequence. The selected catalytic sequences were amplified by attachment of the promoter of T7 RNA polymerase to the 3'-end of the cDNA, followed by transcription to RNA. The method was employed to identify from a small number of ribozyme variants the variant that was most reactive for cleavage of a selected substrate.

The prior art has not taught or suggested more than a limited range of chemical functions for nucleic acids in their interactions with other substances: as targets for proteins that had evolved to bind certain specific oligonucleotide sequences; and more recently, as catalysts with a limited range of activities. Prior "selection" experiments have been limited to a narrow range of variants of a previously described function. Now, for the first time, it will be understood that the nucleic acids are capable of a vastly broad range of functions and the methodology for realizing that capability is disclosed herein.

U.S. patent application Ser. No. 07/536,428, filed Jun. 11, 1990, entitled Systematic Evolution of Ligands by Exponential Enrichment, now abandoned, U.S. Pat. No. 5,270,163, issued Dec. 14, 1993, and U.S. patent application Ser. No. 07/714,131 filed Jun. 10, 1991, both entitled Nucleic Acid Ligands (See also PCT/US91/04078) describe a fundamentally novel method for identifying a nucleic acid ligand for any desired target. Each of these applications, collectively referred to herein as the SELEX Patent Applications, is specifically incorporated herein by reference.

The method of the SELEX Patent Applications is based on the unique insight that nucleic acids have sufficient capacity for forming a variety of two- and three-dimensional structures and sufficient chemical versatility available within their monomers to act as ligands (form specific binding pairs) with virtually any chemical compound, whether large or small in size.

The method involves selection from a mixture of candidates and step-wise iterations of structural improvement, using the same general selection theme, to achieve virtually any desired criterion of binding affinity and selectivity. Starting from a mixture of nucleic acids, preferably comprising a segment of randomized sequence, the method, termed SELEX herein, includes steps of contacting the mixture with the target under conditions favorable for binding, partitioning unbound nucleic acids from those nucleic acids which have bound to target molecules, dissociating the nucleic acid-target pairs, amplifying the nucleic acids dissociated from the nucleic acid-target pairs to yield a ligand-enriched mixture of nucleic acids, then reiterating the steps of binding, partitioning, dissociating and amplifying through as many cycles as desired.

While not bound by theory, SELEX is based on the inventors' insight that within a nucleic acid mixture containing a large number of possible sequences and structures there is a wide range of binding affinities for a given target. A nucleic acid mixture comprising, for example, a 20 nucleotide randomized segment can have $4^{20}$ candidate possibilities. Those which have the higher affinity constants for the target are most likely to bind to the target. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested for binding affinity as pure ligands.

Cycles of selection and amplification are repeated until a desired goal is achieved. In the most general case, selection/amplification is continued until no significant improvement in binding strength is achieved on repetition of the cycle. The method may be used to sample as many as about $10^{18}$ different nucleic acid species. The nucleic acids of the test mixture preferably include a randomized sequence portion as well as conserved sequences necessary for efficient amplification. Nucleic acid sequence variants can be produced in a number of ways including synthesis of randomized nucleic acid sequences and size selection from randomly cleaved cellular nucleic acids. The variable sequence portion may contain fully or partially random sequence; it may also contain subportions of conserved sequence incorporated with randomized sequence. Sequence variation in test nucleic acids can be introduced or increased by mutagenesis before or during the selection/amplification iterations.

In one embodiment of the method of the SELEX Patent Applications, the selection process is so efficient at isolating those nucleic acid ligands that bind most strongly to the selected target, that only one cycle of selection and amplification is required. Such an efficient selection may occur, for example, in a chromatographic-type process wherein the ability of nucleic acids to associate with targets bound on a column operates in such a manner that the column is sufficiently able to allow separation and isolation of the highest affinity nucleic acid ligands.

In many cases, it is not necessarily desirable to perform the iterative steps of SELEX until a single nucleic acid ligand is identified. The target-specific nucleic acid ligand solution may include a family of nucleic acid structures or motifs that have a number of conserved sequences and a number of sequences which can be substituted or added without significantly effecting the affinity of the nucleic acid ligands to the target. By terminating the SELEX process prior to completion, it is possible to determine the sequence of a number of members of the nucleic acid ligand solution family.

A variety of nucleic acid primary, secondary and tertiary structures are known to exist. The structures or motifs that have been shown most commonly to be involved in non-Watson-Crick type interactions are referred to as hairpin loops, symmetric and asymmetric bulges, pseudoknots and myriad combinations of the same. Almost all known cases of such motifs suggest that they can be formed in a nucleic acid sequence of no more than 30 nucleotides. For this reason, it is often preferred that SELEX procedures with contiguous randomized segments be initiated with nucleic acid sequences containing a randomized segment of between about 20–50 nucleotides.

The SELEX Patent Applications also describe methods for obtaining nucleic acid ligands that bind to more than one site on the target molecule, and to nucleic acid ligands that include non-nucleic acid species that bind to specific sites on the target. The SELEX method provides means for isolating and identifying nucleic acid ligands which bind to any envisionable target. However, in preferred embodiments the SELEX method is applied to situations where the target is a protein, including both nucleic acid-binding proteins and proteins not known to bind nucleic acids as part of their biological function.

Basic fibroblast growth factor (bFGF) is a multifunctional effector for many cells of mesenchymal and neuroectodermal origin (Rifkin & Moscatelli (1989) J. Cell Biol. 109:1; Baird & Bohlen (1991) in Peptide Growth Factors and Their Receptors (Sporn, M. B. & Roberts, A. B., eds.); pp. 369–418, Springer, N.Y.; Basilico & Moscatelli (1992) Adv. Cancer Res. 59:115). It is one of the most studied and best characterized members of a family of related proteins that also includes acidic FGF (Jaye et al. (1986) Science 233:541; Abraham et al. (1986) Science 233:545), int-2 (Moore et al. (1986) EMBO J. 5:919), kFGF/hst/KS3 (Delli-Bovi et al. (1987) Cell 50:729; Taira et al. (1987) Proc. Natl. Acad. Sci. U.S.A. 84:2980), FGF-5 (Zhan et al. (1988) Mol. Cell. Biol. 8:3487), FGF-6 (Marics et al. (1988) Oncogene 4:335) and keratinocyte growth factor/FGF-7 (Finch et al. (1989) Science 245:752).

In vitro, bFGF stimulates cell proliferation, migration and induction of plasminogen activator and collagenase activities (Presta et al. (1986) Mol. Cell. Biol. 6:4060; Moscatelli et al. (1986) Proc. Natl. Acad. Sci. U.S.A. 83:2091; Mignatti et al. (1989) J. Cell Biol. 108:671). In vivo, it is one of the most potent inducers of neovascularization. Its angiogenic activity in vivo suggests a role in tissue remodeling and wound healing but also in some disease states that are characterized by pathological neovascularization such as tumor proliferation, tumor metastasis, diabetic retinopathy and rheumatoid arthritis (Folkman & Klagsbrun (1987) Science 235:442; Gospodarowitz (1991) Cell Biology Reviews 25:307).

Although bFGF does not have a signal sequence for secretion, it is found on both sides of the plasma membrane, presumably being exported via exocytosis (Vlodavsky et al. (1991) Trends Biol. Sci. 16:268; Mignatti & Rifkin (1991) J. Cell. Biochem. 47:201). In the extracellular matrix, it is typically associated with a fraction that contains heparan sulfate proteoglycans. Indeed, heparin affinity chromatography has been a useful method for purification of this and other heparin-binding growth factors. In cell culture, bFGF binds to low- and high-affinity sites. The low-affinity sites are composed of cell-associated heparan sulfate proteoglycans to which bFGF binds with approximately nanomolar affinity (Moscatelli (1987) J. Cell. Physiol. 131:123). All biological effects of bFGF are mediated through interaction with the high-affinity binding sites (10–100 pM) that represent the dimeric tyrosine kinase FGF receptor (Ueno et al. (1992) J. Biol. Chem. 267:1470). Five FGF receptor genes have been identified to date, each of which can produce several structural variants as a result of alternative mRNA splicing (Armstrong et al. (1992) Cancer Res. 52:2004; Ueno et al. (1992) supra). There is by now substantial evidence that the low- and the high-affinity binding sites act cooperatively in determining the overall affinity of bFGF. Experiments with mutant cell lines that are deficient in glycosaminoglycan synthesis (Yayon et al. (1991) Cell 64:841) or heparitinase treated cells (Rapraeger et al. (1991) Science 252:1705) have shown that binding of either cell-associated heparan sulfate or, in its absence, exogenously added heparin to bFGF is required for signaling via the tyrosine kinase receptor. Recent resolution of observed Kd into its kinetic components demonstrates that while the association rates of bFGF to the low- and the high-affinity sites are comparable, the dissociation rate of bFGF from the cell surface receptor is 23-fold slower than that for the cell-associated heparan sulfate (Nugent & Edelman (1992) Biochemistry 31:8876). The slower off-rate, however, is only observed when the receptor is bound to the cell surface suggesting that simultaneous binding to both sites contributes to the overall high-affinity binding. This is plausible in light of the observation that the heparin-binding and the receptor-binding sites are located on adjacent but separate regions of the molecule, as determined from the recently solved X-ray crystal structure of bFGF (Zhang et al. (1991) Proc. Natl. Acad. Sci. U.S.A. 88:3446; Eriksson et al. (1991) Proc. Natl. Acad. Sci. U.S.A. 88:3441; Ago et al. (1991) J. Biochem. 110:360; Zhu et al. (1991) Science 251:90).

The idea that bFGF antagonists may have useful medicinal applications is not new (reviewed in Gospodarowitz (1991) supra). bFGF is now known to play a key role in the development of smooth-muscle cell lesions following vascular injury (Reidy et al. (1992) Circulation, Suppl. III 86:III-43). Overexpression of bFGF (and other members of the FGF family) is correlated with many malignant disorders (Halaban et al. (1991) Ann. N.Y. Acad. Sci. 638:232; Takahashi et al. (1990) Proc. Natl. Acad. Sci. U.S.A. 87:5710; Fujimoto et al. (1991) Biochem. Biophys. Res. Commun. 180:386) and recently, neutralizing anti-bFGF antibodies have been found to suppress solid tumor growth in vivo by inhibiting tumor-linked angiogenesis (Hori et al. (1991) Cancer Res. 51:6180). Notable in this regard is the recent therapeutic examination of suramin, a polysulfated naphthalene derivative with known antiprotozoal activity, as an anti-tumor agent. Suramin is believed to inhibit the activity of bFGF through binding in the polyanion binding site and disrupting interaction of the growth factor with its receptor (Middaugh et al. (1992) Biochemistry 31:9016; Eriksson et al. (1991) supra). In addition to having a number of undesirable side effects and substantial toxicity, suramin is known to interact with several other heparin-binding growth factors which makes linking of its beneficial therapeutic effects to specific drug-protein interactions difficult (La Rocca et al. (1990) Cancer Cells 2:106). Anti-angiogenic properties of certain heparin preparations have also been observed (Folkman et al. (1983) Science 221:719; Crum et al. (1985) Science 230:1375) and these effects are probably based at least in part on their ability to interfere with bFGF signaling. While the specific heparin fraction that contributes to bFGF binding is now partially elucidated (Ishai-Michaeli et al. (1992) Biochemistry 31:2080; Turnbull et al. (1992) J. Biol. Chem. 267:10337), a typical heparin preparation is heterogeneous with respect to size, degree of sulfation and iduronic acid content. Additionally, heparin also affects many enzymes and growth factors. Excluding monoclonal antibodies, therefore, specific antagonists of bFGF are not known.

SUMMARY OF THE INVENTION

The present invention includes methods for identifying and producing nucleic acid ligands and the nucleic acid ligands so identified and produced.

Nucleic acid sequences are provided that are ligands of bFGF. Specifically, RNA sequences are provided that are capable of binding specifically to bFGF. Included within the invention are the nucleic acid ligand sequences shown in Tables II–IV.

Also included in this invention are nucleic acid ligands of bFGF that are inhibitors of bFGF. Specifically, RNA ligands are identified and described which inhibit the binding of bFGF to its receptors.

Further included in this invention is a method of identifying nucleic acid ligands and ligand sequences to bFGF comprising the steps of a) preparing a candidate mixture of nucleic acids; b) partitioning between members of said candidate mixture on the basis of affinity to bFGF; and c) amplifying the selected molecules to yield a mixture of nucleic acids enriched for nucleic acid sequences with a relatively higher affinity for binding to bFGF.

More specifically, the present invention includes the RNA ligands to bFGF identified according to the above-described method, including those ligands listed in Tables II–IV. Also included are RNA ligands to bFGF that are substantially homologous to any of the given ligands and that have substantially the same ability to bind and inhibit bFGF. Further included in this invention are RNA ligands to bFGF that have substantially the same structural form as the ligands presented herein and that have substantially the same ability to bind and inhibit bFGF.

The present invention also includes modified nucleotide sequences based on the nucleic acid ligand sequences identified herein and mixtures of the same. Specifically included in this invention are RNA ligands, comprising nucleotides modified at the 2'-amino (2'-NH$_2$) position. The 2'-NH$_2$-modified RNA ligands possess improved in vivo stability.

BRIEF DESCRIPTION OF THE FIGURES

FIG. 4 shows the proposed secondary structures for Family 1 ligands that bind to bFGF with high affinity. Arrows indicate double stranded (stem) regions that flank the conserved loop. Lower case symbols indicate nucleotides in the constant region. The upper case symbols indicate the 30 random nucleotides depicted in Table II.

FIG. 5 shows the proposed secondary structures for Family 2 ligands. The upper case symbols indicate the 30 random nucleotides depicted in Table III.

FIG. 7 shows the starting random RNAs for experiments A and B, and PCR primers used in identifying 2'-NH$_2$-RNA ligands to bFGF (Example 5).

DETAILED DESCRIPTION OF THE PREFERRED EMBODIMENTS

Figure 1:
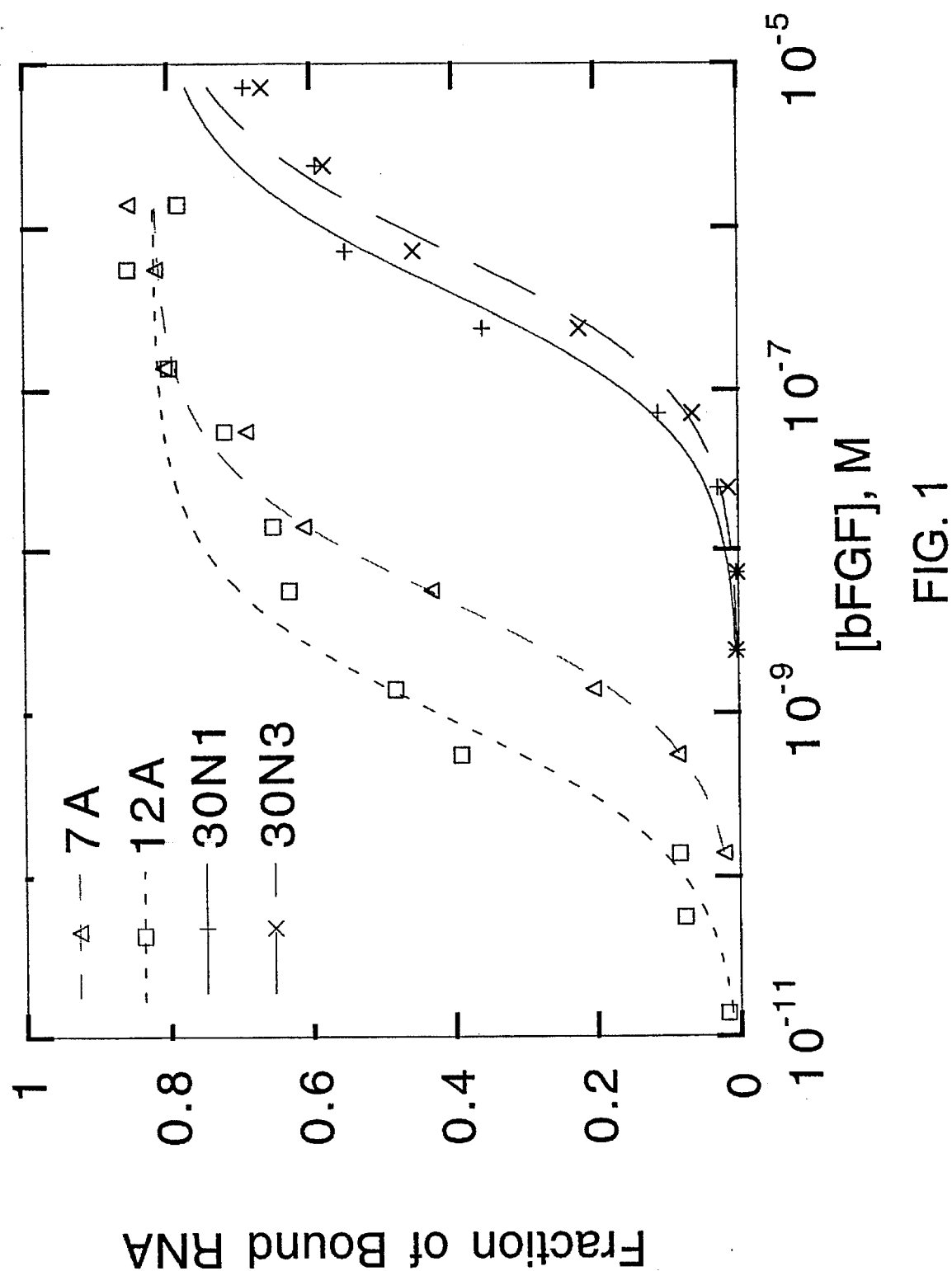
FIG. 1 shows binding curves for family 1 ligand 7A (SEQ ID NO:10) (Δ), family 2 ligand 12A (SEQ ID NO:25) (□), random RNA, SELEX experiment A(+) and random RNA, SELEX experiment B (x). The fraction of RNA bound to nitrocellulose filters is plotted as a function of free protein concentration and data points were fitted to equation 2 as defined in Example 3 below. The following concentrations of RNA were used: <100 pM for 7A and 12A, and 10 nM for random RNAs. Binding reactions were done at 37° C. in phosphate buffered saline containing 0.01% human serum albumin.

This application is an extension and an application of the method for identifying nucleic acid ligands referred to as SELEX. The SELEX method is described in detail in U.S. patent application Ser. No. 07/714,131 filed Jun. 10, 1991 entitled Nucleic Acid Ligands, 07/536,428 filed June 11, 1990 entitled Systematic Evolution of Ligands by EXponential Enrichment, 07/931,473 filed Aug. 17, 1992, now U.S. Pat. No. 5,270,163. These applications are collectively referred to herein as the SELEX Applications. The full text of these applications, including but not limited to, all definitions and descriptions of the SELEX process, are specifically incorporated herein by reference.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: a) to assist in the amplification steps described below; b) to mimic a sequence known to bind to the target; or c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and the nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for the preparation of the initial candidate mixture; methods for partitioning nucleic acids within a candidate mixture; and methods for amplifying partitioned nucleic acids to generate enriched candidate mixtures. The SELEX Patent Applications also describe ligand solutions obtained to a number of target species, including both protein targets wherein the protein is and is not a nucleic acid binding protein.

SELEX provides high affinity ligands of a target molecule. This represents a singular achievement that is unprecedented in the field of nucleic acids research. The present invention applies the SELEX procedure to a specific target, bFGF. In the Example section below, the experimental parameters used to isolate and identify the nucleic acid ligand solutions to bFGF are described.

In order to produce nucleic acids desirable for use as a pharmaceutical, it is preferred that the nucleic acid ligand 1) binds to the target in a manner capable of achieving the desired effect on the target; 2) be as small as possible to obtain the desired effect; 3) be as stable as possible; and 4) be a specific ligand to the chosen target. In most, if not all, situations it is preferred that the nucleic acid ligand have the highest possible affinity to the target.

In co-pending and commonly assigned U.S. patent application Ser. No. 07/964,624, filed Oct. 21, 1992, methods are described for obtaining improved nucleic acid ligands after SELEX has been performed. This application, entitled Methods of Producing Nucleic Acid Ligands is specifically incorporated herein by reference. Included in this application are the following methods relating to: Assays of ligand effects on target molecules; Affinity assays of the ligands; Information boundaries determination; Quantitative and qualitative assessment of individual nucleotide contributions to affinity via secondary SELEX, nucleotide substitution, and chemical modification experiments; and Structural determination. The present invention includes improvements to the nucleic acid ligand solution derived according to these procedures.

This invention includes the specific nucleic acid ligands shown in Tables II–IV. These tables include unmodified RNA ligands to bFGF identified by the SELEX method as described herein. The scope of the ligands covered by this invention extends to all ligands to bFGF identified according to the SELEX procedure. More specifically, this invention includes nucleic acid sequences that are substantially homologous to and that have substantially the same ability to bind bFGF as the specific nucleic acid ligands shown in Tables II–IV. By substantially homologous, it is meant, a degree of primary sequence homology in excess of 70%, most preferably in excess of 80%. Substantially the same ability to bind bFGF means that the affinity is within two orders of magnitude of the affinity of the ligands described herein. It is well within the skill of those of ordinary skill in the art to determine whether a given sequence—substantially homologous to those specifically described herein—has substantially the same ability to bind bFGF.

This invention also includes the specific 2'-NH$_2$-modified nucleic acid ligands shown in Table VIII. These ligands were identified by the SELEX method utilizing a candidate mixture of RNAs wherein all pyrimidines were 2'-deoxy-2'-NH$_2$. All purines utilized in these experiments were unmodified, or 2'-OH. More specifically, this invention includes nucleic acid sequences that are substantially homologous to and that have substantially the same ability to bind bFGF as the specific nucleic acid ligands shown in Table VIII.

Figure 6:
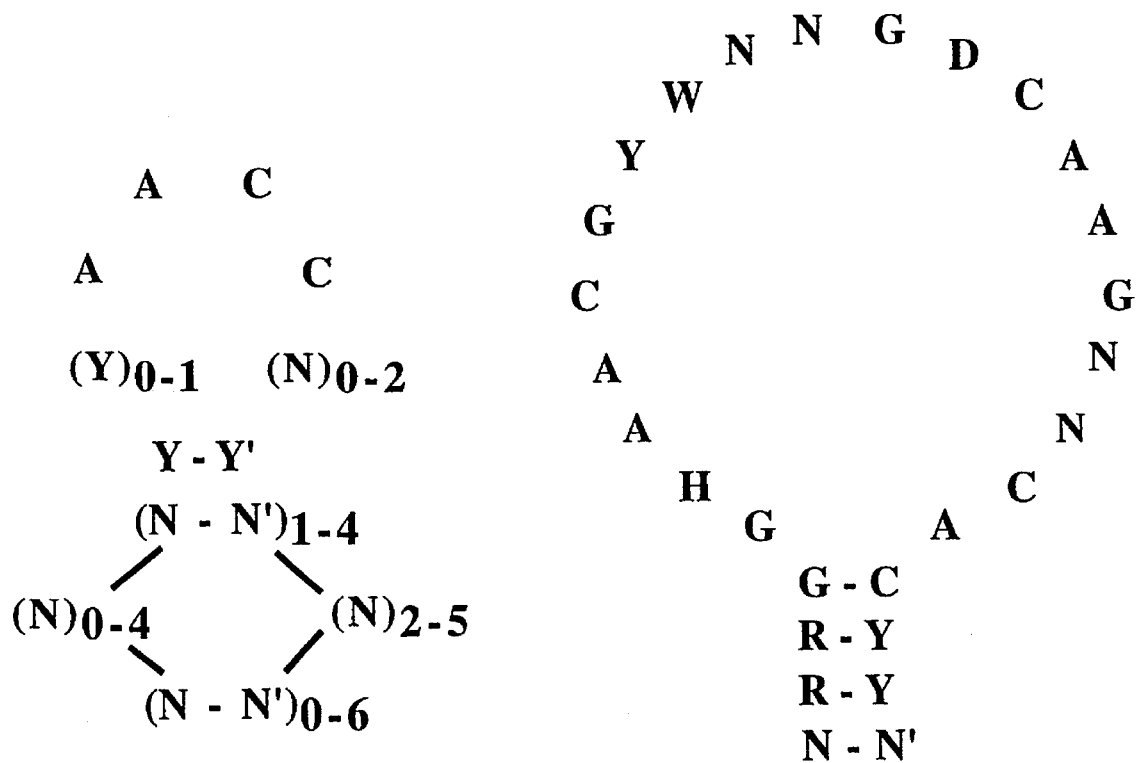
FIG. 6 shows the consensus structures for Family 1 and Family 2 ligands. Y=C or U; R=A or G; W=A or U; H=A, U, or C; D=A, G, or U; N=any base. Complementary bases are primed. Symbols in parenthesis indicate a variable number of bases or base pairs at that position ranging within limits given in the subscript.

A review of the proposed structural formations shown in FIG. 6 for the family 1 and 2 unmodified ligands shows that sequences that have little or no primary sequence homology may still have substantially the same ability to bind bFGF. It can be assumed that the disparate sequences have similar structures that give rise to the ability to bind to bFGF, and that each of the family 1 and family 2 sequence ligands are able to assume structures that appear very similar to the binding site of bFGF even though they do not bind the same site. For these reasons, the present invention also includes RNA ligands that have substantially the same structure as the ligands presented herein and that have substantially the same ability to bind bFGF as the RNA ligands shown in Tables II and III. "Substantially the same structure" includes all RNA ligands having the common structural elements of the sequences given in Tables II,III and VIII.

Two SELEX experiments were conducted to select unmodified RNA ligands to bFGF (Example 2). These experiments yielded two sequence families of high-affinity nucleic acid ligands to bFGF. A review of the two sequence families (Tables II and III) shows that sequences that have little or no primary sequence homology may still have substantially the same ability to bind bFGF. It appears that the disparate sequences may have a common structure that gives rise to the ability to bind to bFGF, and that each of the sequence family 1 and 2 ligands are able to assume structures that appear very similar to the binding site of bFGF even though they do not bind the same site. High-affinity nucleic acid ligands selected in the presence of heparin (Experiment B) exhibited the consensus sequence of family 2. These ligands bind a bFGF protein in which a conformation change has been induced by heparin. The present invention also includes RNA ligands that have substantially the same structure as the ligands presented herein and that have substantially the same ability to bind bFGF as the RNA ligands shown in Tables II, III and VIII. "Substantially the same structure" includes all RNA ligands having the common structural elements of the sequences given in Tables II, III and VIII.

This invention also includes the ligands described above, wherein certain chemical modifications have been made in order to increase the in vivo stability of the ligand, enhance or mediate the delivery of the ligand, or reduce the clearance rate from the body. Examples of such modifications include chemical substitutions at the ribose and/or phosphate and/or base positions of a given RNA sequence. See, e.g., Cook et al. PCT Application WO 92/03568; U.S. Pat. No. 5,118,672 of Schinazi et al.; Hobbs et al. (1973) Biochem. 12:5138; Guschlbauer et al. (1977) Nucleic Acids Res. 4:1933; Ghibahara et al. (1987) Nucleic Acids Res. 15:4403; Pieken et al. (1991) Science 253:314, each of which is specifically incorporated herein by reference. Such modifications may be made post-SELEX (modification of previously identified unmodified ligands) or by incorporation into the SELEX process as described below.

The high-affinity nucleic acid ligands of the present invention may also have various properties, including the ability to inhibit the biological activity of bFGF. Representative ligands from sequence family 1 and 2 were found to inhibit binding of bFGF to both low- and high-affinity cell-surface receptors (Example 4). These nucleic acid ligands may be useful as specific and potent neutralizers of bFGF activity in vivo.

Two SELEX experiments were conducted with RNA candidate mixtures wherein all pyrimidine moieties were 2'-deoxy-2'-NH$_2$-pyrimidines (Example 5, experiments A and B). These experiments yielded the sequences shown in Table VIII. Sequence families 1A, 1B, 1C, 2 and 3 were identified, as well as four families containing two sequences each ("two-member families"), single sequences ("other sequences"), and sequences binding nitrocellulose ("nitrocellulose-binding family"). The nitrocellulose-binding ligands have an increased affinity to nitrocellulose as well as an increased affinity to bFGF. The high affinity of identified 2'-NH$_2$ ligands for bFGF is shown in Table IX and FIG. 8. 2'-NH$_2$-modified RNA ligands able to inhibit the in vitro activity of bFGF were identified (FIG. 9). These ligands were shown to inhibit the biological activity of bFGF in vivo (Example 6).

The nucleic acid ligands and nucleic acid ligand solutions to bFGF described herein are useful as pharmaceuticals, and as part of gene therapy treatments. Example 6 shows the ability of 2'-NH$_2$-modified RNA ligands to inhibit the in vivo biological activity of bFGF. Further, the nucleic acid ligands to bFGF described herein may be used beneficially for diagnostic purposes.

Example 1. Experimental Procedures

Materials. bFGF was obtained from Bachem California (molecular weight 18,000 Da, 154 amino acids). Tissue culture grade heparin (average molecular weight 16,000 Da) was purchased from Sigma. Low molecular weight heparin (5,000 Da) was from Calbiochem. All other chemicals were at least reagent grade and were purchased from commercial sources.

SELEX. Essential features of the SELEX protocol have been described in detail in the SELEX Applications and in previous papers (Tuerk & Gold (1990) Science 249:505; Tuerk et al. (1992a) Proc. Natl. Acad. Sci. U.S.A. 89:6988; Tuerk et al. (1992b) in Polymerase Chain Reaction (Ferre, F. Mullis, K., Gibbs, R. & Ross, A., eds.) Birkhauser, N.Y.). The SELEX protocol may be performed in generally the same manner for unmodified RNA selection as for selection with 2'-deoxy-2'-$NH_2$ pyrimidines as described in Example 5 below. Briefly, DNA templates for in vitro transcription (that contain a region of thirty random positions flanked by constant sequence regions) and the corresponding PCR primers were synthesized chemically (Operon). The random region was generated by utilizing an equimolar mixture of the four nucleotides during oligonucleotide synthesis. The two constant regions were designed to contain PCR primer annealing sites, a primer annealing site for cDNA synthesis, T7 RNA polymerase promoter region, and restriction enzyme sites that allow cloning into vectors (See Table I).

An initial pool of RNA molecules was prepared by in vitro transcription of about 200 picomoles (pmol) ($10^{14}$ molecules) of the double stranded DNA template utilizing T7 RNA polymerase (New England Biolabs). Transcription mixtures consisted of 100–300 nM template, 5 units/ul T7 RNA polymerase, 40 mM Tris-Cl buffer (pH 8.0) containing 12 mM $MgCl_2$, 5 mM DTT, 1 mM spermidine, 0.002% Triton X-100, and 4% PEG. Transcription mixtures were incubated at 37° C. for 2–3 hours. These conditions typically resulted in transcriptional amplification of 10- to 100-fold.

Selections for high affinity RNA ligands were done by incubating bFGF (10–100 pmol) with RNA (90–300 pmol) for 10 minutes at 37° C. in 50 ul of phosphate buffered saline (PBS)(10.1 mM $Na_2HPO_4$, 1.8 mM $KH_2PO_4$, 137 mM NaCl, 2.7 mM KCl, pH 7.4), then separating the protein-RNA complexes from the unbound species by nitrocellulose filter partitioning (Tuerk & Gold (1990) supra). The selected RNA (which typically amounts to 0.3–8% of the total input RNA) was then extracted from the filters and reverse transcribed into cDNA by avian myeloblastosis virus reverse transcriptase (AMV RT, Life Sciences). Reverse transcriptions were done at 48° C. (30 minutes) in 50 mM Tris buffer (pH 8.3), 60 mM NaCl, 6 mM Mg(OAc)$_2$, 10 mM DTT, and 1 unit/ul AMV RT. Amplification of the cDNA by PCR under standard conditions yielded sufficient amounts of double-stranded DNA for the next round of in vitro transcription.

Nitrocellulose Filter Binding Assay.

Oligonucleotides bound to proteins can be effectively separated from the unbound species by filtration through nitrocellulose membrane filters (Yarus & Berg (1970) Anal. Biochem. 35:450; Lowary & Uhlenbeck (1987) Nucleic Acids Res. 15:10483; Tuerk & Gold (1990) supra). Nitrocellulose filters (Millipore, 0.45 um pore size, type HA) were secured on a filter manifold and washed with 4–10 ml of buffer. Following incubations of $^{32}$P-labeled RNA with serial dilutions of the protein (5–10 min) at 37° C. in buffer (PBS) containing 0.01% human serum albumin (HSA), the solutions were applied to the filters under gentle vacuum in 45 ul aliquots and washed with 5 ml of PBS. The filters were then dried under an infrared lamp and counted in a scintillation counter.

Cloning and Sequencing. Individual members of the enriched pools were cloned into pUC18 vector and sequenced as described (Schneider et al. (1992) J. Mol. Biol. (228:862–869); Tuerk & Gold (1990) supra).

Example 2. SELEX Experiments Targeting bFGF.

Following the procedures described in Example 1 above, two SELEX experiments (Experiments A and B) targeting bFGF were initiated with separate pools of randomized unmodified RNA, each pool consisting of approximately $10^{14}$ molecules. The constant sequence regions that flank the randomized region, along with the corresponding primers, were different in each experiment. The two template/primer combinations used are shown in Table I.

Selections were conducted in PBS at 37° C. The selection conducted in Experiment B was done in the presence of heparin (Sigma, molecular weight 5,000–32,000 Da, average molecular weight 16,000 Da) in the selection buffer at the molar ratio of 1/100 (heparin/bFGF). Heparin competes for binding of randomized RNA to bFGF. The amount of heparin used significantly reduced but did not eliminate RNA binding to bFGF (data not shown). The rationale for using heparin was two-fold. First, heparin is known to induce a small conformational change in the protein and also stabilizes bFGF against thermal denaturation. Second, the apparent competitive nature of binding of heparin with randomized RNA to bFGF was expected to either increase the stringency of selection for the heparin binding site or direct the binding of RNA ligands to alternative site(s).

Significant improvement in affinity of RNA ligands to bFGF was observed in Experiment A after ten rounds, and in Experiment B after thirteen rounds. Sequencing of these enriched pools of RNA ligands revealed a definite departure from randomness which indicated that the number of different molecules remaining in the pool was substantially reduced. Individual members of the enriched pools were then cloned into pUC18 vector and sequenced as described in Example 1.

49 clones were sequenced from Experiment A, and 37 clones from Experiment B. From the total of 86 sequences, 71 were unique. Two distinct families could be identified based on overlapping regions of sequence homology (FIGS. A and 5 and Tables II and III). A number of sequences with no obvious homology to members of either of the two families were also present, as expected (Irvine et al. (1991) J. Mol. Biol. 222:739), and are shown in Table IV.

The consensus sequence from family 1 ligands (Table II) is defined by a contiguous stretch of 9 bases, CUAACCNGG (SEQ ID NO:7). This suggests a minimal structure consisting of a 4–5 nucleotide loop that includes the strongly conserved AACC sequence and a bulged stem (FIG. 6 and Table VI). The consensus sequence for family 2 ligands (Table III) is more extended and contains less conserved regions, RRGGHAACGYWNNGDCAAGNNCACYY (SEQ ID NO:23). Here, most of the strongly conserved positions are accommodated in a larger (19–21 nucleotide) loop (FIG. 6 and Table VII). Additional structure within the loop is possible.

The existence of two distinct sequence families in the enriched pools of RNA suggest that there are two convergent solutions for high-affinity binding to bFGF. SELEX experiment A contributed members to both sequence families (Table II). All of the sequences from the SELEX experiment B (selected in the presence of heparin), on the other hand, belong either to family 2 (Table III) or to the "other sequences" family (Table IV), but none were found in family 1. This is surprising in view of the fact that bFGF was present in a molar excess of 100-fold over heparin during selections. The effective molar excess of bFGF over heparin, however, was probably much smaller. Average molecular weight of heparin used in selections was 16,000 Da. Since each sugar unit weighs 320 Da and at least eight sugar units are required for high-affinity binding to bFGF, six molecules of bFGF, on average, can bind to a molecule of heparin. This reduces the molar ratio of heparin to bFGF to 1:16. In practice, this amount of heparin is sufficient to reduce the observed affinity of the unselected RNA pool for bFGF by a factor of five (data not shown). The observed exclusion of an entire ligand family by the presence of a relatively small amount of heparin in the selection buffer may be a consequence of a conformational change in the protein induced by heparin. Because of the relative amounts of heparin and bFGF that were used in selections, this model requires that the heparin-induced conformation persist after the protein-heparin complex has dissociated, and that the lifetime of this conformer is long enough to permit equilibration with the RNA ligands.

Family 2 sequences are comprised of clones derived from both SELEX experiments. This suggests that the flanking constant regions typically play a relatively minor role in determining the affinity of these ligands and supports the premise that the consensus sequence in this family is the principal determinant of high-affinity binding to bFGF.

Example 3. Determination of Binding Affinities for bFGF.

Equilibrium Dissociation Constants.

In the simplest case, equilibrium binding of RNA to bFGF can be described by equation 1:

$$RNA.bFGF \rightleftharpoons RNA + bFGF \qquad (1)$$

The fraction of bound RNA (q) is related to the concentration of free protein, [P] (equation 2):

$$q = f[P]/([P] + K_d) \qquad (2)$$

where $K_d$ is the equilibrium dissociation constant and f reflects the efficiency of retention of the protein-RNA complexes on nitrocellulose filters. Mean value of f for bFGF was 0.82.

In order to eliminate higher order structures, all RNA solutions were heated to 90° C. in PBS for 2–3 minutes and cooled on ice prior to incubation with protein. Only single bands for all RNA clones were detected on non-denaturing polyacrylamide gels following this treatment.

Relative binding affinity of individual ligands to bFGF cannot be predicted from sequence information. Unique sequence clones were therefore screened for their ability to bind to bFGF by measuring the fraction of radiolabeled RNA bound to nitrocellulose filters following incubation with 4 and 40 nM protein. This screening method was sufficiently accurate to allow several clones to be identified that had dissociation constants in the nanomolar range. Binding of these select clones was then analyzed in more detail.

High-affinity RNA ligands for bFGF were found in both sequence families (Tables VI and VII). The affinity of clones that did not belong to either family was generally lower (data not shown).

The original, unselected RNA pools bound to bFGF with 300 nM (set A) and 560 nM (set B) affinities (FIG. 1). SELEX therefore allowed the isolation of ligands with at least 2 orders of magnitude better affinity for bFGF.

In order to address the question of specificity, a representative set of high-affinity ligands for bFGF (5A (SEQ ID NO:9) and 7A (SEQ ID NO:10) from family 1; 12A (SEQ ID NO:25) and 26A (SEQ ID NO:26) from family 2) was tested for binding to four other heparin-binding proteins. It was found that the affinity of these ligands for acidic FGF, thrombin, antithrombin III, and vascular endothelial growth factor was relatively weak ($K_d$ > 0.3 uM)(data not shown).

Example 4. RNA Ligand Inhibition of bFGF Receptor Binding.

The same four high-affinity RNA ligands (5A and 7A from family 1, 12A and 26A from family 2) were also tested for their ability to inhibit binding of bFGF to the low- and the high-affinity cell-surface receptors.

Receptor Binding Studies. bFGF was labeled with $^{125}$I by the Iodo-Gen (Pierce) procedure as described by Moscatelli (1987) supra. Confluent baby hamster kidney (BHK) cells were washed extensively with PBS and then incubated for 2 hours at 4° C. with αMEM medium containing 10 ng/ml $^{125}$I-bFGF in PBS, 0.1% HSA, 1 unit/ml RNasein, and serial dilutions of high-affinity RNA. In a separate experiment it was established that the RNA is not significantly degraded under these conditions. The amount of $^{125}$I-bFGF bound to the low- and the high-affinity receptor sites was determined as described by Moscatelli (1987) supra.

Figure 2B:
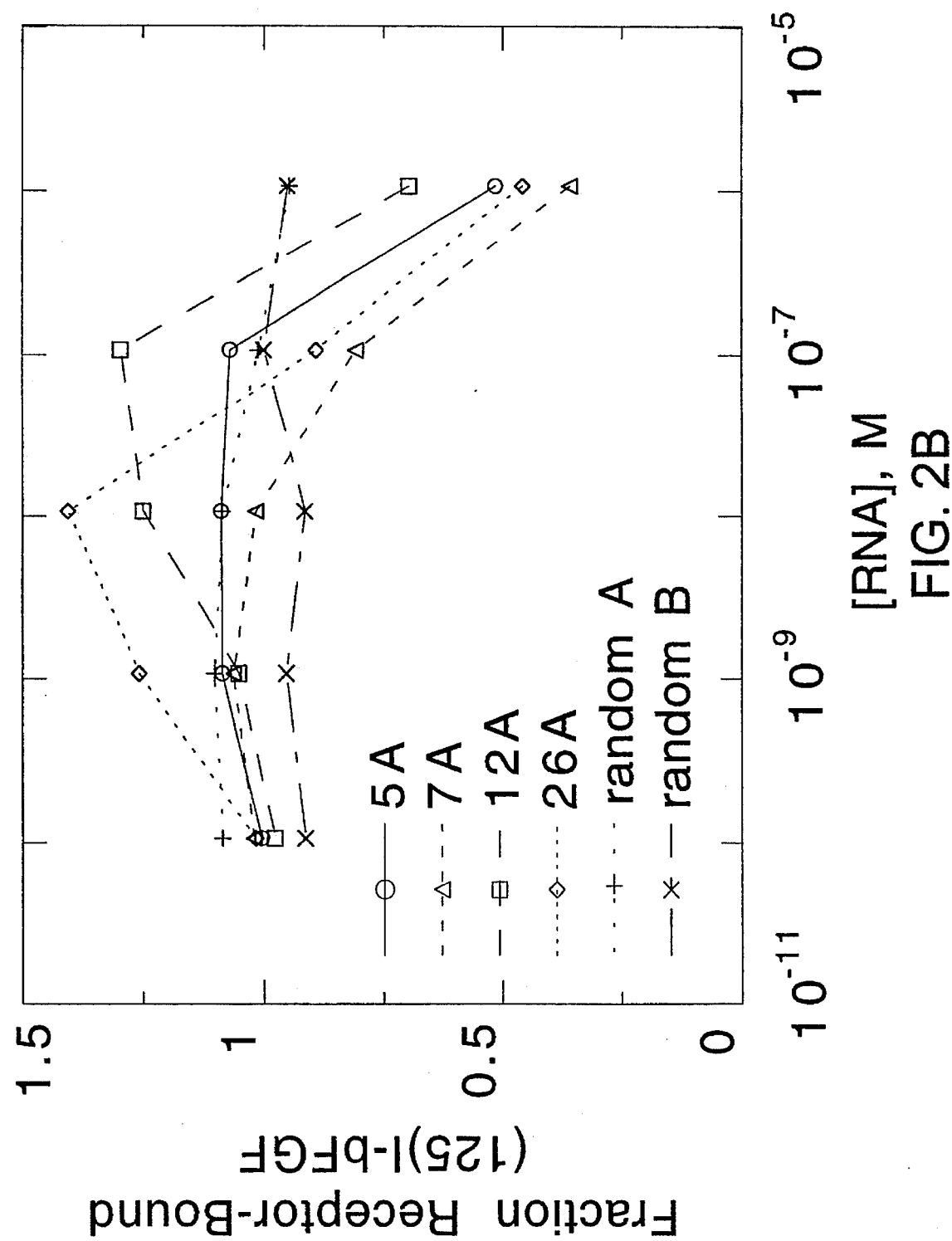
FIG. 2 shows the effect of RNA ligands 5A (SEQ ID NO:9) (○), 7A (SEQ ID NO:10) (Δ), 12A (SEQ ID NO:25) (□), 26A (SEQ ID NO:26) (◊), random RNA, SELEX experiment A (+) and random RNA, SELEX experiment B (x) on binding of $^{125}$I-bFGF to the low-affinity (FIG. 2A) and the high-affinity (FIG. 2B) cell-surface receptors. Experiments were done essentially as described in Roghani & Moscatelli (1992) J. Biol. Chem. 267:22156.

All four ligands competed for the low-affinity receptor sites while the unselected (random) RNAs did not (FIG. 2A). The concentration of RNA required to effect half-displacement of bFGF from the low-affinity receptor was 5–20 nM for ligands 5A, 7A and 26A, and >100 nM for ligand 12A. Half-displacement from the high-affinity sites is observed at the concentration of RNA near 1 uM for ligands 5A, 7A and 26A, and >1 uM for ligand 12A (FIG. 2B). Again, random RNAs did not compete for the high-affinity receptor. The observed difference in concentration of RNA required to displace bFGF from the low- and high-affinity receptors is expected as a reflection of the difference in affinity of the two receptor classes for bFGF (2–10 nM for the low-affinity sites and 10–100 pM for the high-affinity sites).

Figure 3:
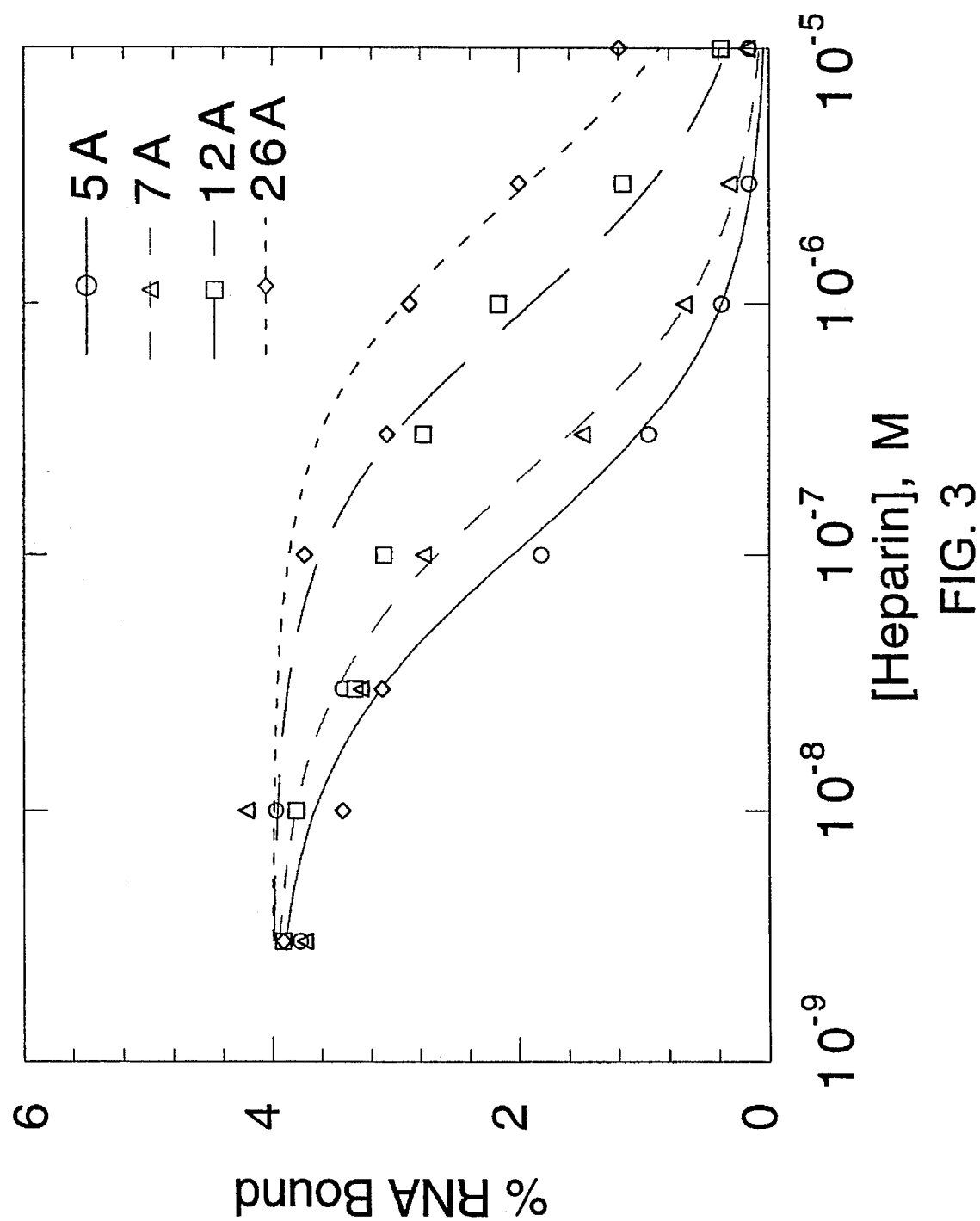
FIG. 3 shows the competitive displacement of $^{32}$P-labeled RNA ligands 5A (SEQ ID NO:9) (○), 7A (SEQ ID NO:10) (Δ), 12A (SEQ ID NO:25) (□), and 26A (SEQ ID NO:26) (◊) by heparin (average molecular weight 5,000 Da). Percent of total input RNA bound to nitrocellulose filters is plotted as a function of heparin concentration. Experiments were done at 37° C. in phosphate buffered saline containing 0.01% human serum albumin, 0.3 uM RNA, and 30 nM bFGF.
Figure 8:
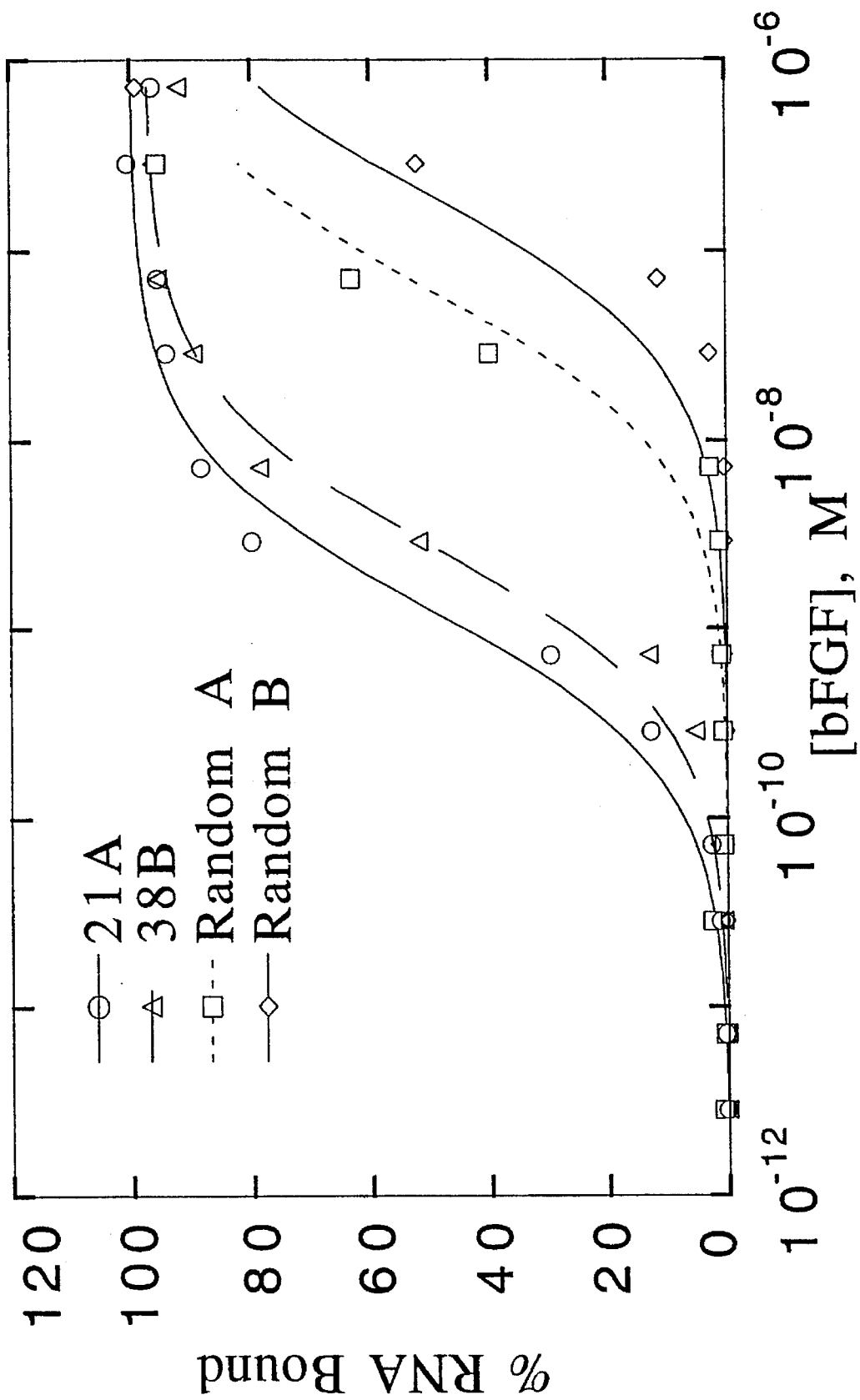
FIG. 8 shows the binding curves for 2'-NH$_2$ modified RNA ligands 21A (SEQ ID NO:104) (o) (SELEX experiment A), 38B (SEQ ID NO:112) (Δ) (SELEX experiment B) and the initial (random) RNAs (A and B) from which these ligands were selected (□, ◊).
Figure 9B:
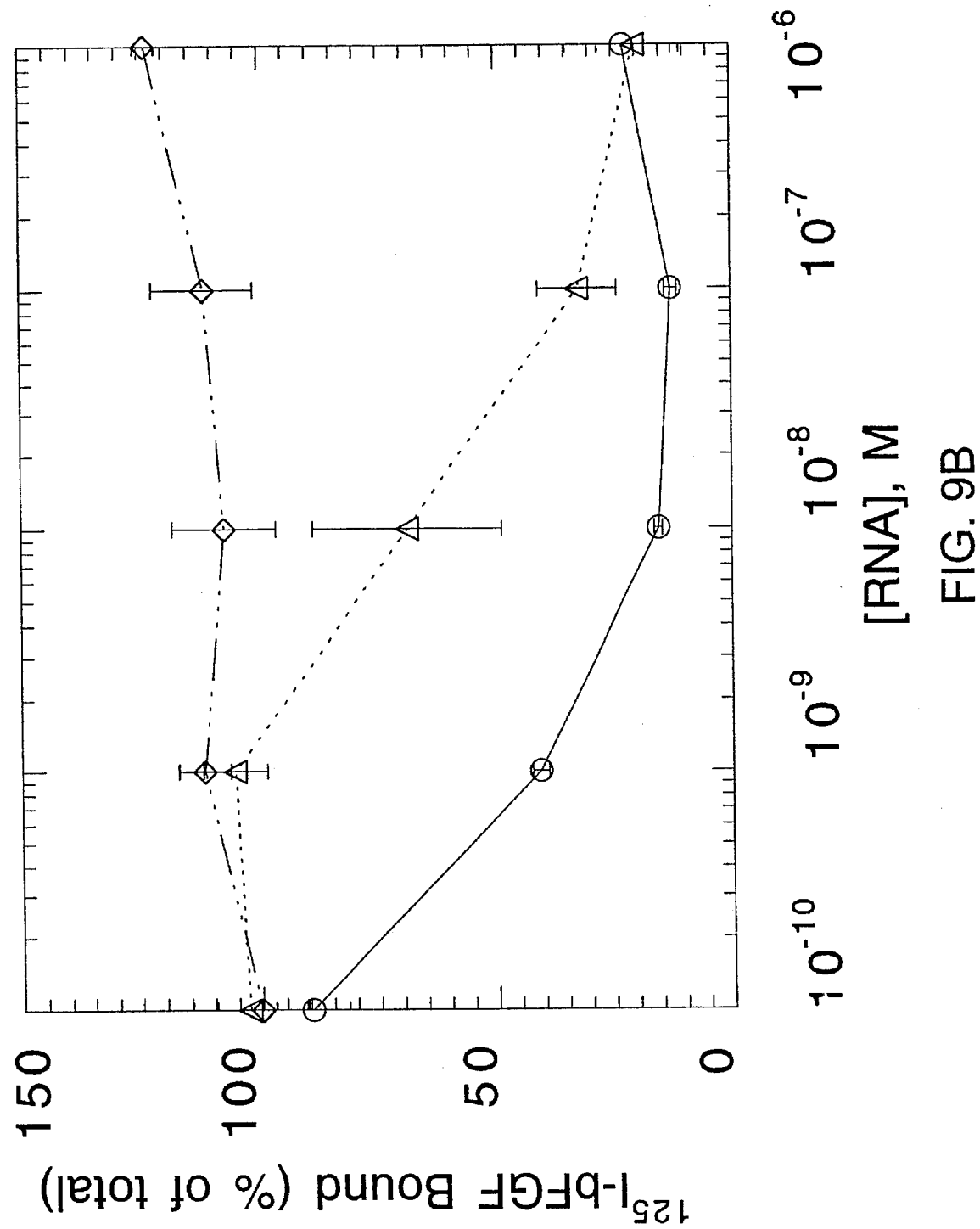
FIG. 9 shows 2'-NH$_2$-modified RNA ligand inhibition of $^{125}$I-bFGF binding to the low-affinity (Panel A) and the high-affinity (Panel B) cell surface receptors. The ligands tested were 21A (SEQ ID NO:104) (Δ), 21A-tc (SEQ ID NO:186) (o), and random RNA A (◊).

Binding curves for modified RNA ligands 21A, 38B and random RNAs were determined (FIG. 8). RNA concentrations were determined from their absorbance reading at 260 nm and were typically less than 100 pM. Binding reactions were conducted at 37° C. in phosphate buffered saline containing 0.01% human serum albumin and 1 mM DTT. Heparin competitively displaced RNA ligands from both sequence families (FIG. 3), although higher concentrations of heparin were required to displace members of family 2 from bFGF.

The selective advantage obtained through the SELEX procedure is based on affinity to bFGF. RNA ligands can in principle bind to any site on the protein, and it is therefore important to examine the activity of the ligands in an appropriate functional assay. The relevant functional experiment for the selected high-affinity ligands is testing their ability to inhibit binding of bFGF to its cell-surface receptors since this is how bFGF exerts its biological activity. The fact that several representative high-affinity RNA ligands inhibited binding of bFGF to both receptor classes (in accord with their relative binding affinities) suggests that these ligands bind at or near the receptor binding site(s). Further support for this notion comes from the observation that heparin competes for binding of these ligands to bFGF. High affinity ligands from family 1 and family 2 may bind to different sites on bFGF. This invention includes covalently connecting components from the two ligand families into a single, more potent inhibitor of bFGF.

Example 5. Modified 2'-NH₂ pyrimidine RNA Ligands to bFGF.

In order to generate ligands with improved stability in vivo, two SELEX experiments (A and B) targeting bFGF were initiated with separate pools of randomized RNA containing amino ($NH_2$) functionalities at the 2'-position of each pyrimidine. Starting ligand pools for the two experiments contained approximately $10^{14}$ molecules (500 pmols) of modified RNA randomized at 30 (SELEX experiment A) and 50 (SELEX experiment B) contiguous positions. The starting RNAs and the corresponding PCR primers are defined in FIG. 7. Following twelve rounds of SELEX, the affinity of the modified RNA pools was improved by 1–2 orders of magnitude. Sequences corresponding to the evolved regions of modified RNA are shown in Table VIII. It is interesting to note that individual nucleotides occur at substantially different frequencies with guanine being conspicuously overrepresented (43%), adenine and uridine occurring at about equal frequencies (22% and 21%) and cytosine being underrepresented (14%).

Ligands with similar primary structures were grouped into families and their consensus sequences are shown below each sequence set (Table VIII). Groups of sequences with similar primary structure (families) have been aligned in Table VIII and their consensus sequences are shown below each set. Pairs of similar/related sequences, sequences that could not be included in any of the families ("other sequences") and sequences that correspond to ligands that bind additionally to nitrocellulose filters with high affinity have been shown in separate groups. Letter N in a sequence indicates an ambiguous position on a sequencing gel. Italicized letter N in a consensus sequence indicates a position that is not conserved (i.e., any nucleotide may be found at that position).

All unique ligands were screened for their binding affinities for bFGF by measuring the fraction of RNA bound to bFGF at two protein concentrations (5.0 and 0.5 nM bFGF). This affinity screening allowed identification of those ligands with highest affinity for bFGF. Binding of a group of these ligands was analyzed over a range of bFGF concentrations (FIG. 8) and their dissociation constants (Kd's) were determined as described (Jellinek et al. (1993) Proc. Natl. Acad. Sci. U.S.A. 90:11227–11231) (Table IX). RNA concentrations were determined from their absorbance reading at 260 nM (and were typically <100 pM). Binding reactions were done at 37° C. in phosphate buffered saline containing 0.01% human serum albumin and 1 mM DTT.

The minimal sequence information required for high-affinity binding to bFGF was examined for several of the 2'-NH₂ modified ligands by deletion analyses as described (Tuerk et al. (1990) J. Mol. Biol. 213:749–761). Truncated ligands 21A-t (GGUGUGUGGAAGACAGCGGGUGGuuc (SEQ ID NO:186); the letter "t" is used to designate truncated sequences derived from the corresponding parent sequences; underlined G's are those guanine nucleotides added to improve the efficiency of transcription; lowercase letters are from the constant sequence region), 58A-t (GGACGGCGUGGUCCGAGGGUGGCGAGU) (SEQ ID NO:187) and 34B-t (GgaggacgaugcggAACGGGAGGUACGA GAGCGGGAGC) (SEQ ID NO:188) were synthesized enzymatically using T7 RNA polymerase from synthetic DNA templates and their binding affinity for bFGF was examined. Ligand 21A-t binds to bFGF in a biphasic manner with a dissociation constant of the higher affinity component ($K_{d1}$) of 0.1 nM, mole fraction of the higher affinity component ($x1$) of 0.5 and a dissociation constant of the lower affinity component ($K_{d2}$) of 270 nM (for interpretation of biphasic binding see Jellinek et al. (1993) supra). Binding of ligand 58A-t to bFGF is also biphasic ($K_{d1}$=1.8 nM, $x1$=0.5, $K_{d2}$=180 nM). Binding of ligand 34B-t is monophasic ($K_{d1}$=3 nM).

The ability to inhibit the binding of $^{125}$I-bFGF to high and low-affinity cell-surface receptors was examined (FIG. 9). Experiments were conducted as described in Moscatelli (1987) supra using confluent cultures of baby hamster kidney cells. Specific activity of bFGF was 915 cpm/fmol. Each data point represents the average of two experiments.

Several high-affinity ligands were found to inhibit binding of bFGF to its cell-surface receptors, with truncated versions of ligand 21A being the most effective inhibitors (FIG. 9). Random RNA was ineffective in this concentration range (up to 1μM). pck Example 6. In Vivo Inhibition of bFGF Activity With 2 -NH₂-modified RNA Ligands.

The potential in vivo activity of the bFGF antagonist oligonucleotide ligand A2/C2 was evaluated in the rat corneal angiogenesis assay. The basic approach for this assay was originally developed and reported by Gimbrone et al. (1974) JNCI 52:413 using rabbit corneas for implantation of tumor cells or tumor cell extracts in polyacrylamide gel. The technique was later refined by Langer and Folkman (1976) Nature 263:797 to utilize a less irritating polymer, hydroxyethylmethacrylate (Hydron). The corneal implantation method for assessing angiogenic activity associated with cell extracts or growth factors suspended in Hydron has been used in guinea pigs by Polverini et. al. (1977) Nature 269:804 and more recently in rats by Koch et. al. (1992) Science 258:1798.

The corneal angiogenesis assay used herein is a modification of the techniques described in the above references. The assay is conducted in rat corneas; however, the implantation method is different in that the corneal pocket is made using small scissors instead of a spatula for the blunt dissection of the corneal stroma. Additionally, Hydron could not be used as the carrier substance for bFGF because the protein was denatured by the high concentration of ethanol and/or the polymerization reaction. Other carriers were studied and it was determined that nitrocellulose filter material (Millipore) was the most suitable medium for implantation since it readily absorbs the protein, is not denaturing to proteins, and is not proinflammatory or irritating to the corneal stroma.

The basic design of the first in vivo assay was to compare the potential angiogenic effects of (1) untreated nitrocellulose, (2) nitrocellulose soaked in oligonucleotide ligand A2/C2, (3) nitrocellulose soaked in bFGF, and (4) nitrocellulose soaked in a solution of ligand A2/C2 and bFGF combined.

The disks to be implanted were punched out of a standard

Millipore nitrocellulose filter using a punch made from a 16 gauge hypodermic needle. The diameter of the implanted disks was approximately 1 mm. Prior to implantation the disks were soaked in a given test solution for at least one hour to ensure saturation. The four solutions in this experiment were (1) Ringer's physiologic salt solution, (2) RNA ligand A2/C2 in 10% PBS/90% water, (3) bFGF in Ringer's solution, and (4) 1:1 mixture of ligand A2/C2 and bFGF.

The respective soaked disks were implanted into the corneal stroma of three rats for each treatment group. Both eyes of each rat received the same treatment so that there were six test eyes in each test group. The test solutions were handled using sterile technique. The animals were anesthetized with a general anesthetic mixture containing acepromazine, ketamine, and xylazine. The corneal surgery, which involved making an incision through the corneal epithelium into the underlying stroma with subsequent dissection of a pocket in the stroma, was conducted under a stereomicroscope. The surgical site was cleaned with a dilute solution of organic iodine. A single dose of ophthamic antibiotic was administered post-surgically.

Following implantation of the disks, the animals were returned to their cages where they were maintained under standard husbandry conditions until their eyes were examined stereomicroscopically on post-surgical days seven and fourteen. The eyes were evaluated for amount of corneal cloudiness around the implant and for amount of vascular ingrowth into the normally avascular cornea. The scoring system used for quantitation of vascular ingrowth was based on degrees of vascularization around the circumference of the cornea (potential total=360°) multiplied by the extent of vascular ingrowth toward the implant (1=no growth; 2=ingrowth ⅓ of distance to implant; 3=ingrowth ⅔× of distance to implant; 4= ingrowth to implant; 5=ingrowth into and around implant). The mean score of the eyes in each group was then determined. The minimum score of 360 (360×1) is normal while the maximum possible score with extensive vascular ingrowth into the implant is 1800 (360×5). The results are shown in Table X.

The results from this preliminary experiment provide two important findings for this ligand. First, although the ligand did not prevent the bFGF stimulated ingrowth of vessels into the cornea (Group IV vs. Group III), it did diminish the amount of vascular ingrowth as well as the amount of corneal cloudiness observed microscopically at both seven and fourteen days following implantation. Secondly, the introduction of the oligonucleotide alone (Group II) into the cornea did not result in any adverse effects such as irritation, inflammation, or angiogenesis. These findings suggest that the oligonucleotide has the desired antagonistic effect for bFGF and that it is biocompatible when administered in vivo at relatively high local concentration (60 uM).

SEQUENCE LISTING ( 1 ) GENERAL INFORMATION:

( i i i ) NUMBER OF SEQUENCES: 227

( 2 ) INFORMATION FOR SEQ ID NO:1:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
GGGAGCUCAG  AAUAAACGCU  CAANNNNNN   NNNNNNNNN   NNNNNNNNN              50
NNNUUCGACA  UGAGGCCCGG  AUCCGGC                                         77
```

( 2 ) INFORMATION FOR SEQ ID NO:2:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
CCGAAGCTTA   ATACGACTCA   CTATAGGGAG   CTCAGAATAA   ACGCTCAA            48
```

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GCCGGATCCG GGCCTCATGT CGAA 24

( 2 ) INFORMATION FOR SEQ ID NO:4:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GGGAGAUGCC UGUCGAGCAU GCUGNNNNN NNNNNNNNN NNNNNNNNN 50

NNNNGUAGCU AAACAGCUUU GUCGACGGG 79

( 2 ) INFORMATION FOR SEQ ID NO:5:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

CCCGAAGCTT AATACGACTC ACTATAGGGA GATGCCTGTC GAGCATGCTG 50

( 2 ) INFORMATION FOR SEQ ID NO:6:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

CCCGTCGACA AAGCTGTTTA GCTAC 25

( 2 ) INFORMATION FOR SEQ ID NO:7:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

CUAACCNGG 9

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

UGCUAUUCGC CUAACUCGGC GCUCCUACCU 30

( 2 ) INFORMATION FOR SEQ ID NO:9:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

AUCUCCUCCC GUCGAAGCUA ACCUGGCCAC   30

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

UCGGCGAGCU AACCAAGACA CUCGCUGCAC   30

( 2 ) INFORMATION FOR SEQ ID NO:11:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GUAGCACUAU CGGCCUAACC CGGUAGCUCC   30

( 2 ) INFORMATION FOR SEQ ID NO:12:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

ACCCGCGGCC UCCGAAGCUA ACCAGGACAC   30

( 2 ) INFORMATION FOR SEQ ID NO:13:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

UGGGUGCUAA CCAGGACACA CCCACGCUGU   30

( 2 ) INFORMATION FOR SEQ ID NO:14:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

CACGCACAGC UAACCAAGCC ACUGUGCCCC   30

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

CUGCGUGGUA UAACCACAUG CCCUGGGCGA                    30

( 2 ) INFORMATION FOR SEQ ID NO:16:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

UGGGUGCUUA ACCAGGCCAC ACCCUGCUGU                    30

( 2 ) INFORMATION FOR SEQ ID NO:17:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

CUAGGUGCUA UCCAGGACUC UCCCUGGUCC                    30

( 2 ) INFORMATION FOR SEQ ID NO:18:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

UGCUAUUCGC CUAGCUCGGC GCUCCUACCU                    30

( 2 ) INFORMATION FOR SEQ ID NO:19:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

AGCUAUUCGC CCAACCCGGC GCUCCCGACC                    30

( 2 ) INFORMATION FOR SEQ ID NO:20:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

ACCAGCUGCG UGCAACCGCA CAUGCCUGG                     29

( 2 ) INFORMATION FOR SEQ ID NO:21:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

CAGGCCCCGU CGUAAGCUAA CCUGGACCCU                            30

( 2 ) INFORMATION FOR SEQ ID NO:22:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

UGGGUGCUAA CCACCACACA CUCACGCUGU                            30

( 2 ) INFORMATION FOR SEQ ID NO:23:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

RRGGHAACGY WNNGDCAAGN NCACYY                                26

( 2 ) INFORMATION FOR SEQ ID NO:24:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

GGGUAACGUU GUGACAAGUA CACCUGCGUC                            30

( 2 ) INFORMATION FOR SEQ ID NO:25:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

GGGGCAACGC UACAGACAAG UGCACCCAAC                            30

( 2 ) INFORMATION FOR SEQ ID NO:26

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

CGUCAGAAGG CAACGUAUAG GCAAGCACAC                            30

( 2 ) INFORMATION FOR SEQ ID NO:27:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

CCUCUCGAAG ACAACGCUGU GACAAGACAC                            30

( 2 ) INFORMATION FOR SEQ ID NO:28:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:28:

AGUGGGAAAC GCUACUUGAC AAGACACCAC                         30

( 2 ) INFORMATION FOR SEQ ID NO:29:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:29:

GGCUACGCUA AUGACAAGUG CACUUGGGUG                         30

( 2 ) INFORMATION FOR SEQ ID NO:30:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:30:

CUCUGGUAAC GCAAUGUCAA GUGCACAUGA                         30

( 2 ) INFORMATION FOR SEQ ID NO:31:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:31:

AGCCGCAGGU AACGGACCGG CGAGACCAUU                         30

( 2 ) INFORMATION FOR SEQ ID NO:32:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:32:

ACGAGCUUCG UAACGCUAUC GACAAGUGCA                         30

( 2 ) INFORMATION FOR SEQ ID NO:33:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:33:

AAGGGGAAAC GUUGAGUCCG GUACACCCUG                         30

5,459,015

31

32

-continued ( 2 ) INFORMATION FOR SEQ ID NO:34:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

AGGGUAACGU ACUGGCAAGC UCACCUCAGC                 30

( 2 ) INFORMATION FOR SEQ ID NO:35:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:35:

GAGGUAACGU ACGACAAGAC CACUCCAACU                 30

( 2 ) INFORMATION FOR SEQ ID NO:36:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:36:

AGGUAACGCU GAGUCAAGUG CACUCGACAU                 30

( 2 ) INFORMATION FOR SEQ ID NO:37:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:37:

GGGAAACGCU AUCGACGAGU GCACCCGGCA                 30

( 2 ) INFORMATION FOR SEQ ID NO:38:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:38:

CCGAGGGUAA CGUUGGGUCA AGCACACCUC                 30

( 2 ) INFORMATION FOR SEQ ID NO:39:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

UCGGGGUAAC GUAUUGGCAA GGCACCCGAC                 30

( 2 ) INFORMATION FOR SEQ ID NO:40:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:40:

GGUAACGCUG UGGACAAGUG CACCAGCUGC     30

( 2 ) INFORMATION FOR SEQ ID NO: 41:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

AGGGUAACGU ACUGGCAAGC UCACCUCAGC     30

( 2 ) INFORMATION FOR SEQ ID NO:42:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:42:

AGGGUAACGU AUAGUCAAGA CACCUCAAGU     30

( 2 ) INFORMATION FOR SEQ ID NO:43:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:43:

GGGUAACGCA UUGGCAAGAC ACCCAGCCCC     30

( 2 ) INFORMATION FOR SEQ ID NO:44:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:44:

GAGGAAACGU ACCGUCGAGC CACUCCAUGC     30

( 2 ) INFORMATION FOR SEQ ID NO:45:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:45:

AGGUAACGCU GAGUCAAGUG CACUCGACAU     30

( 2 ) INFORMATION FOR SEQ ID NO:46:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (xi) SEQUENCE DESCRIPTION: SEQ ID NO:46:

GGGUAACGUG UGACAAGAUC ACCCAGUUUG                    30

(2) INFORMATION FOR SEQ ID NO:47:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (xi) SEQUENCE DESCRIPTION: SEQ ID NO:47:

CACAGGGCAA CGCUGCUGAC AAGUGCACCU                    30

(2) INFORMATION FOR SEQ ID NO:48:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (xi) SEQUENCE DESCRIPTION: SEQ ID NO:48:

ACGCCAAGUG AGUCAGCAAC AGAGCGUCCG                    30

(2) INFORMATION FOR SEQ ID NO:49:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (xi) SEQUENCE DESCRIPTION: SEQ ID NO:49:

CCAGUGAGUC CUGGUAAUCC GCAUCGGGCU                    30

(2) INFORMATION FOR SEQ ID NO:50:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (xi) SEQUENCE DESCRIPTION: SEQ ID NO:50:

CUUCAGAACG GCAUAGUGGU CGGCCGCGCC                    30

(2) INFORMATION FOR SEQ ID NO:51:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (xi) SEQUENCE DESCRIPTION: SEQ ID NO:51:

AGGUCACUGC GUCACCGUAC AUGCCUGGCC                    30

(2) INFORMATION FOR SEQ ID NO:52:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:52:

UCCAACGAAC GGCCCUCGUA UUCAGCCACC      30

( 2 ) INFORMATION FOR SEQ ID NO:53:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

ACUGGAACCU GACGUAGUAC AGCGACCCUC      30

( 2 ) INFORMATION FOR SEQ ID NO:54:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:54:

UCUCGCUGCG CCUACACGGC AUGCCGGGA      29

( 2 ) INFORMATION FOR SEQ ID NO:55:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:55:

GAUCACUGCG CAAUGCCUGC AUACCUGGUC      30

( 2 ) INFORMATION FOR SEQ ID NO:56:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:56:

UCUCGCUGCG CCUACACGGC AUGCCCGGGA      30

( 2 ) INFORMATION FOR SEQ ID NO:57:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:57:

UGACCAGCUG CAUCCGACGA UAUACCCUGG      30

( 2 ) INFORMATION FOR SEQ ID NO:58:

( i ) SEQUENCE CHARACTERISTICS:

( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:58:

GGCACACUCC AACGAGGUAA CGUUACGGCG 30

( 2 ) INFORMATION FOR SEQ ID NO:59:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:59:

AGCGGAACGC CACGUAGUAC GCCGACCCUC 30

( 2 ) INFORMATION FOR SEQ ID NO:60:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:60:

ACCCACGCCC GACAACCGAU GAGUUCUCGG 30

( 2 ) INFORMATION FOR SEQ ID NO:61:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:61:

UGCUUUGAAG UCCUCCCCGC CUCUCGAGGU 30

( 2 ) INFORMATION FOR SEQ ID NO:62:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:62:

AUGCUGAGGA UAUUGUGACC ACUUCGGCGU 30

( 2 ) INFORMATION FOR SEQ ID NO:63:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( x i ) SEQUENCE DESCRIPTION: SEQ ID NO:63:

ACCCACGCCC GACAACCGAU GAGCUCGGA 29

( 2 ) INFORMATION FOR SEQ ID NO:64:

( i ) SEQUENCE CHARACTERISTICS:
( A ) LENGTH: 30 base pairs (B) TYPE: nucleic acid
        (C) STRANDEDNESS: single
        (D) TOPOLOGY: linear (xi) SEQUENCE DESCRIPTION: SEQ ID NO:64:

AGUCCGGAUG CCCCACUGGG ACUACAUUGU                30

(2) INFORMATION FOR SEQ ID NO:65:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:65:

AAGUCCGAAU GCCACUGGGA CUACCACUGA                30

(2) INFORMATION FOR SEQ ID NO:66:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:66:

ACUCUCACUG CGAUUCGAAA UCAUGCCUGG                30

(2) INFORMATION FOR SEQ ID NO:67:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:67:

AGGCUGGGUC ACCGACAACU GCCCGCCAGC                30

(2) INFORMATION FOR SEQ ID NO:68:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:68:

AGCCGCAGGU AACGGACCGG CGAGACCACU                30

(2) INFORMATION FOR SEQ ID NO:69:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:69:

GCAUGAAGCG GAACUGUAGU ACGCGAUCCA                30

(2) INFORMATION FOR SEQ ID NO:70:

(i) SEQUENCE CHARACTERISTICS:
        (A) LENGTH: 30 base pairs
        (B) TYPE: nucleic acid (C) STRANDEDNESS: single
(D) TOPOLOGY: linear (x i) SEQUENCE DESCRIPTION: SEQ ID NO:70:

GGGUAACGUU GUGACAAGUA CACCUGCGUU 30

(2) INFORMATION FOR SEQ ID NO:71:

(i) SEQUENCE CHARACTERISTICS:
(A) LENGTH: 30 base pairs
(B) TYPE: nucleic acid
(C) STRANDEDNESS: single
(D) TOPOLOGY: linear (x i) SEQUENCE DESCRIPTION: SEQ ID NO:71:

GGGUAACGUU GUGACAAGUA CACCUGCGUC 30

(2) INFORMATION FOR SEQ ID NO:72:

(i) SEQUENCE CHARACTERISTICS:
(A) LENGTH: 30 base pairs
(B) TYPE: nucleic acid
(C) STRANDEDNESS: single
(D) TOPOLOGY: linear (x i) SEQUENCE DESCRIPTION: SEQ ID NO:72:

GGGUAACGUU GUGACAAGUA CACCUGCGUC 30

(2) INFORMATION FOR SEQ ID NO:73:

(i) SEQUENCE CHARACTERISTICS:
(A) LENGTH: 30 base pairs
(B) TYPE: nucleic acid
(C) STRANDEDNESS: single
(D) TOPOLOGY: linear (x i) SEQUENCE DESCRIPTION: SEQ ID NO:73:

GGGUAACGUU GUGACAACUA CACCUGCGUC 30

(2) INFORMATION FOR SEQ ID NO:74:

(i) SEQUENCE CHARACTERISTICS:
(A) LENGTH: 30 base pairs
(B) TYPE: nucleic acid
(C) STRANDEDNESS: single
(D) TOPOLOGY: linear (x i) SEQUENCE DESCRIPTION: SEQ ID NO:74:

GGGUAACGUU GUGACAACUA CACCUGCGUC 30

(2) INFORMATION FOR SEQ ID NO:75:

(i) SEQUENCE CHARACTERISTICS:
(A) LENGTH: 30 base pairs
(B) TYPE: nucleic acid
(C) STRANDEDNESS: single
(D) TOPOLOGY: linear (x i) SEQUENCE DESCRIPTION: SEQ ID NO:75:

GGGUAACGUU GUGACAACUA CACCUGCGUC 30

(2) INFORMATION FOR SEQ ID NO:76:

(i) SEQUENCE CHARACTERISTICS:
(A) LENGTH: 30 base pairs
(B) TYPE: nucleic acid
(C) STRANDEDNESS: single (D) TOPOLOGY: linear (xi) SEQUENCE DESCRIPTION: SEQ ID NO:76:

CGUCAGAAGG CAACGUAUAG GCAAGCACAC 30

(2) INFORMATION FOR SEQ ID NO:77:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:77:

GUAGCACUAU CGGCCUAACC CGGUAGCUCC 30

(2) INFORMATION FOR SEQ ID NO:78:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:78:

ACCCGCGGCC UCCGAAGCUA ACCAGGACAC 30

(2) INFORMATION FOR SEQ ID NO:79:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:79:

AGGUCACUGC GUCACCGUAC AUGCCUGGCC 30

(2) INFORMATION FOR SEQ ID NO:80:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:80:

AGGUCACUGC GUCACCGUAC AUGCCUGGCC 30

(2) INFORMATION FOR SEQ ID NO:81:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:81:

GGCACACUCC AACGAGGUAA CGUUACGGCG 30

(2) INFORMATION FOR SEQ ID NO:82:

(i) SEQUENCE CHARACTERISTICS:
(A) LENGTH: 30 base pairs
(B) TYPE: nucleic acid
(C) STRANDEDNESS: single
(D) TOPOLOGY: linear ( x i ) SEQUENCE DESCRIPTION: SEQ ID NO:82:

GGGGCAACGC UACAGACAAG UGCACCCAAC    30

( 2 ) INFORMATION FOR SEQ ID NO:83:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:83:

GGGGCAACGC UACAGACAAG UGCACCCAAC    30

( 2 ) INFORMATION FOR SEQ ID NO:84:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:84:

GGGGCAACGC UACAGACAAG UGCACCCAAC    30

( 2 ) INFORMATION FOR SEQ ID NO:85:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:85:

UGGGUGCUAA CCAGGACACA CCCACGCUGU    30

( 2 ) INFORMATION FOR SEQ ID NO:86:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:86:

CCGAGGGUAA CGUUGGGUCA AGCACACCUC    30

( 2 ) INFORMATION FOR SEQ ID NO:87:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:87:

GGGAAACGCU AUCGACGAGU GCACCCGGCA    30

( 2 ) INFORMATION FOR SEQ ID NO:88:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear (x i) SEQUENCE DESCRIPTION: SEQ ID NO:88:

GGGAAACGCU AUCGACGAGU GCACCCGGCA 30

(2) INFORMATION FOR SEQ ID NO:89:

(i) SEQUENCE CHARACTERISTICS:
(A) LENGTH: 30 base pairs
(B) TYPE: nucleic acid
(C) STRANDEDNESS: single
(D) TOPOLOGY: linear (x i) SEQUENCE DESCRIPTION: SEQ ID NO:89:

ACUCUCACUG CGAUUCGAAA UCAUGCCUGG 30

(2) INFORMATION FOR SEQ ID NO:90:

(i) SEQUENCE CHARACTERISTICS:
(A) LENGTH: 30 base pairs
(B) TYPE: nucleic acid
(C) STRANDEDNESS: single
(D) TOPOLOGY: linear (x i) SEQUENCE DESCRIPTION: SEQ ID NO:90:

GCAUGAAGCG GAACUGUAGU ACGCGAUCCA 30

(2) INFORMATION FOR SEQ ID NO:91:

(i) SEQUENCE CHARACTERISTICS:
(A) LENGTH: 30 base pairs
(B) TYPE: nucleic acid
(C) STRANDEDNESS: single
(D) TOPOLOGY: linear (x i) SEQUENCE DESCRIPTION: SEQ ID NO:91:

GCAUGAAGCG GAACUGUAGU ACGCGAUCCA 30

(2) INFORMATION FOR SEQ ID NO:92:

(i) SEQUENCE CHARACTERISTICS:
(A) LENGTH: 30 base pairs
(B) TYPE: nucleic acid
(C) STRANDEDNESS: single
(D) TOPOLOGY: linear (x i) SEQUENCE DESCRIPTION: SEQ ID NO:92:

AGGGUAACGU ACUGGCAAGC UCACCUCAGC 30

(2) INFORMATION FOR SEQ ID NO:93:

(i) SEQUENCE CHARACTERISTICS:
(A) LENGTH: 30 base pairs
(B) TYPE: nucleic acid
(C) STRANDEDNESS: single
(D) TOPOLOGY: linear (x i) SEQUENCE DESCRIPTION: SEQ ID NO:93:

AGGGUAACGU ACUGGCAAGC UCACCUCAGC 30

(2) INFORMATION FOR SEQ ID NO:94:

(i) SEQUENCE CHARACTERISTICS:
(A) LENGTH: 30 base pairs
(B) TYPE: nucleic acid
(C) STRANDEDNESS: single
(D) TOPOLOGY: linear (x i) SEQUENCE DESCRIPTION: SEQ ID NO:94:

GGUAACGCUG UGGACAAGUG CACCAGCUGC    30

( 2 ) INFORMATION FOR SEQ ID NO:95:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-$NH_2$ 2 cytosine ( i x ) FEATURE:
        ( D ) OTHER INFORMATION: All U's are 2'-$NH_2$ 2 uracil ( x i ) SEQUENCE DESCRIPTION: SEQ ID NO:95:

GGGAGACAAG AAUAACGCUC AANNNNNNN NNNNNNNNN NNNNNNNNN    50

NNUUCGACAG GAGGCUCACA ACAGGC    76

( 2 ) INFORMATION FOR SEQ ID NO:96:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:96:

TAATACGACT CACTATAGGG AGACAAGAAU AACGCUCAA    39

( 2 ) INFORMATION FOR SEQ ID NO:97:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:97:

GCCTGTTGTG AGCCTCCTGT CGAA    24

( 2 ) INFORMATION FOR SEQ ID NO:98:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-$NH_2$ 2 cytosine ( i x ) FEATURE:
        ( D ) OTHER INFORMATION: All U's are 2'-$NH_2$ 2 uracil ( x i ) SEQUENCE DESCRIPTION: SEQ ID NO:98:

GGGAGGACGA UGCGGNNNNN NNNNNNNNNN NNNNNNNNNN NNNNNNNNN    50

NNNNNNNNN NNNNCAGAC GACTCGCCCG A    81

( 2 ) INFORMATION FOR SEQ ID NO:99:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear -continued ( x i ) SEQUENCE DESCRIPTION: SEQ ID NO:99:

TAATACGACT CACTATAGGG AGGACGAUGC GG        32

( 2 ) INFORMATION FOR SEQ ID NO:100:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:100:

TCGGGCGAGT CGTCTG        16

( 2 ) INFORMATION FOR SEQ ID NO:101:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-$NH_2$ 2 cytosine ( i x ) FEATURE:
        ( D ) OTHER INFORMATION: All U's are 2'-$NH_2$ 2 uracil ( x i ) SEQUENCE DESCRIPTION: SEQ ID NO:101:

ACANGGAGUU GUGUGGAAGG CAGGGGGAGG        30

( 2 ) INFORMATION FOR SEQ ID NO:102:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-$NH_2$ 2 cytosine ( i x ) FEATURE:
        ( D ) OTHER INFORMATION: All U's are 2'-$NH_2$ 2 uracil ( x i ) SEQUENCE DESCRIPTION: SEQ ID NO:102:

UGUGUGGAAG GCAGUGGGAG GUUCAGUGGU        30

( 2 ) INFORMATION FOR SEQ ID NO:103:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-$NH_2$ 2 cytosine ( i x ) FEATURE:
        ( D ) OTHER INFORMATION: All U's are 2'-$NH_2$ 2 uracil ( x i ) SEQUENCE DESCRIPTION: SEQ ID NO:103:

AAAGUUGUGU GGAAGACAGU GGGAGGUGAA        30

( 2 ) INFORMATION FOR SEQ ID NO:104:

( i ) SEQUENCE CHARACTERISTICS:

(A) LENGTH: 30 base pairs
(B) TYPE: nucleic acid
(C) STRANDEDNESS: single
(D) TOPOLOGY: linear (ix) FEATURE:
(D) OTHER INFORMATION: All C's are 2'-NH$_2$ 2 cytosine (ix) FEATURE:
(D) OTHER INFORMATION: All U's are 2'-NH$_2$ 2 uracil (xi) SEQUENCE DESCRIPTION: SEQ ID NO:104:

GUAGACUAAU GUGUGGAAGA CAGCGGGUGG 30

(2) INFORMATION FOR SEQ ID NO:105:

(i) SEQUENCE CHARACTERISTICS:
(A) LENGTH: 30 base pairs
(B) TYPE: nucleic acid
(C) STRANDEDNESS: single
(D) TOPOLOGY: linear (ix) FEATURE:
(D) OTHER INFORMATION: All C's are 2'-NH$_2$ 2 cytosine (ix) FEATURE:
(D) OTHER INFORMATION: All U's are 2'-NH$_2$ 2 uracil (xi) SEQUENCE DESCRIPTION: SEQ ID NO:105:

NNAGUUGUGU GGAAGACAGU GGGGGGUUGA 30

(2) INFORMATION FOR SEQ ID NO:106:

(i) SEQUENCE CHARACTERISTICS:
(A) LENGTH: 30 base pairs
(B) TYPE: nucleic acid
(C) STRANDEDNESS: single
(D) TOPOLOGY: linear (ix) FEATURE:
(D) OTHER INFORMATION: All C's are 2'-NH$_2$ 2 cytosine (ix) FEATURE:
(D) OTHER INFORMATION: All U's are 2'-NH$_2$ 2 uracil (xi) SEQUENCE DESCRIPTION: SEQ ID NO:106:

GGUGUGUNGA AGACAGUGGG UNGUUUAGNC 30

(2) INFORMATION FOR SEQ ID NO:107:

(i) SEQUENCE CHARACTERISTICS:
(A) LENGTH: 30 base pairs
(B) TYPE: nucleic acid
(C) STRANDEDNESS: single
(D) TOPOLOGY: linear (ix) FEATURE:
(D) OTHER INFORMATION: All C's are 2'-NH$_2$ 2 cytosine (ix) FEATURE:
(D) OTHER INFORMATION: All U's are 2'-NH$_2$ 2 uracil (xi) SEQUENCE DESCRIPTION: SEQ ID NO:107:

AUGGUGUGUG GAAGACAGUG GGUGGUUGCA 30

(2) INFORMATION FOR SEQ ID NO:108:

(i) SEQUENCE CHARACTERISTICS:
(A) LENGTH: 30 base pairs
(B) TYPE: nucleic acid
(C) STRANDEDNESS: single (D) TOPOLOGY: linear (ix) FEATURE:
                (D) OTHER INFORMATION: All C's are 2'-NH$_2$ 2 cytosine (ix) FEATURE:
                (D) OTHER INFORMATION: All U's are 2'-NH$_2$ 2 uracil (xi) SEQUENCE DESCRIPTION: SEQ ID NO:108:

ACUGUUGUGU GGAAGACAGC GGGUGGUUGA                                                        30

(2) INFORMATION FOR SEQ ID NO:109:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (ix) FEATURE:
                (D) OTHER INFORMATION: All C's are 2'-NH$_2$ 2 cytosine (ix) FEATURE:
                (D) OTHER INFORMATION: All U's are 2'-NH$_2$ 2 uracil (xi) SEQUENCE DESCRIPTION: SEQ ID NO:109:

AAUGUAGGCU GUGUGGUAGA CAGUGGGUGG                                                        30

(2) INFORMATION FOR SEQ ID NO:110:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (ix) FEATURE:
                (D) OTHER INFORMATION: All C's are 2'-NH$_2$ 2 cytosine (ix) FEATURE:
                (D) OTHER INFORMATION: All U's are 2'-NH$_2$ 2 uracil (xi) SEQUENCE DESCRIPTION: SEQ ID NO:110:

GAUGUGUGGA GGGCAGUGGG GGGUACCAUA                                                        30

(2) INFORMATION FOR SEQ ID NO:111:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (ix) FEATURE:
                (D) OTHER INFORMATION: All C's are 2'-NH$_2$ 2 cytosine (ix) FEATURE:
                (D) OTHER INFORMATION: All U's are 2'-NH$_2$ 2 uracil (xi) SEQUENCE DESCRIPTION: SEQ ID NO:111:

GGGGUCAAGG ACAGUGGGUG GUGGUGGUGU                                                        30

(2) INFORMATION FOR SEQ ID NO:112:

(i) SEQUENCE CHARACTERISTICS:
                (A) LENGTH: 50 base pairs
                (B) TYPE: nucleic acid
                (C) STRANDEDNESS: single
                (D) TOPOLOGY: linear (ix) FEATURE:

(D) OTHER INFORMATION: All C's are 2'-NH₂ 2 cytosine (ix) FEATURE:
(D) OTHER INFORMATION: All U's are 2'-NH₂ 2 uracil (xi) SEQUENCE DESCRIPTION: SEQ ID NO:112:

UGCUGCGGUG CGCAUGUGUG GAAGACAGAG GGAGGUUAGA AUCAUGACGU  50

(2) INFORMATION FOR SEQ ID NO:113:

(i) SEQUENCE CHARACTERISTICS:
(A) LENGTH: 50 base pairs
(B) TYPE: nucleic acid
(C) STRANDEDNESS: single
(D) TOPOLOGY: linear (ix) FEATURE:
(D) OTHER INFORMATION: All C's are 2'-NH₂ 2 cytosine (ix) FEATURE:
(D) OTHER INFORMATION: All U's are 2'-NH₂ 2 uracil (xi) SEQUENCE DESCRIPTION: SEQ ID NO:113:

ACAGACCGUG UGUGGAAGAC AGUGGGAGGU UAUUAACGUA GUGAUGGCGC  50

(2) INFORMATION FOR SEQ ID NO:114:

(i) SEQUENCE CHARACTERISTICS:
(A) LENGTH: 49 base pairs
(B) TYPE: nucleic acid
(C) STRANDEDNESS: single
(D) TOPOLOGY: linear (ix) FEATURE:
(D) OTHER INFORMATION: All C's are 2'-NH₂ 2 cytosine (ix) FEATURE:
(D) OTHER INFORMATION: All U's are 2'-NH₂ 2 uracil (xi) SEQUENCE DESCRIPTION: SEQ ID NO:114:

GCUGCGGUGC GCAUGUGUGG AAGACAGAGG GAGGUUAGAA UCGUGCCGC  49

(2) INFORMATION FOR SEQ ID NO:115:

(i) SEQUENCE CHARACTERISTICS:
(A) LENGTH: 50 base pairs
(B) TYPE: nucleic acid
(C) STRANDEDNESS: single
(D) TOPOLOGY: linear (ix) FEATURE:
(D) OTHER INFORMATION: All C's are 2'-NH₂ 2 cytosine (ix) FEATURE:
(D) OTHER INFORMATION: All U's are 2'-NH₂ 2 uracil (xi) SEQUENCE DESCRIPTION: SEQ ID NO:115:

GAAAACUACG GUGUGUGGAA GACAGUGGGA GGUUGGCAGU CUGUGUCCGU  50

(2) INFORMATION FOR SEQ ID NO:116:

(i) SEQUENCE CHARACTERISTICS:
(A) LENGTH: 49 base pairs
(B) TYPE: nucleic acid
(C) STRANDEDNESS: single
(D) TOPOLOGY: linear (ix) FEATURE:
(D) OTHER INFORMATION: All C's are 2'-NH₂ 2 cytosine (ix) FEATURE:

(D) OTHER INFORMATION: All U's are 2'-NH₂ 2 uracil (xi) SEQUENCE DESCRIPTION: SEQ ID NO:116:

UCCAUCGUGG AAGACAGUGG GAGGUUAGAA UCAUGACGUC AGACGACUC 49

(2) INFORMATION FOR SEQ ID NO:117:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ix) FEATURE:
        (D) OTHER INFORMATION: All C's are 2'-NH₂ 2 cytosine (ix) FEATURE:
        (D) OTHER INFORMATION: All U's are 2'-NH₂ 2 uracil (xi) SEQUENCE DESCRIPTION: SEQ ID NO:117:

UGUGAUUUGU GUGGAAGGCA GUGGGAGGUG UCGAUGUAGA UCUGGCGAUG 50

(2) INFORMATION FOR SEQ ID NO:118:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ix) FEATURE:
        (D) OTHER INFORMATION: All C's are 2'-NH₂ 2 cytosine (ix) FEATURE:
        (D) OTHER INFORMATION: All U's are 2'-NH₂ 2 uracil (xi) SEQUENCE DESCRIPTION: SEQ ID NO:118:

UGUGUGGAAG ACAGUGGGWG GUU 23

(2) INFORMATION FOR SEQ ID NO:119:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (D) OTHER INFORMATION: All C's are 2'-NH₂ 2 cytosine (ix) FEATURE:
        (D) OTHER INFORMATION: All U's are 2'-NH₂ 2 uracil (xi) SEQUENCE DESCRIPTION: SEQ ID NO:119:

UGUGUGGAAG GGUACCUGAG UGGGGAUGGG 30

(2) INFORMATION FOR SEQ ID NO:120:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ix) FEATURE:
        (D) OTHER INFORMATION: All C's are 2'-NH₂ 2 cytosine (ix) FEATURE:
        (D) OTHER INFORMATION: All U's are 2'-NH₂ 2 uracil (xi) SEQUENCE DESCRIPTION: SEQ ID NO:120:

AAGACUGUGU GGAAGGGGUG UAGGGGUUGG G                                                    31

( 2 ) INFORMATION FOR SEQ ID NO:121:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-$NH_2$ 2 cytosine ( i x ) FEATURE:
        ( D ) OTHER INFORMATION: All U's are 2'-$NH_2$ 2 uracil ( x i ) SEQUENCE DESCRIPTION: SEQ ID NO:121:

UAGGGCCGCA ACUGUGUGGA AGGGAGGAUG CGUCAUGGGG GUUGGGCUG                                  49

( 2 ) INFORMATION FOR SEQ ID NO:122:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-$NH_2$ 2 cytosine ( i x ) FEATURE:
        ( D ) OTHER INFORMATION: All U's are 2'-$NH_2$ 2 uracil ( x i ) SEQUENCE DESCRIPTION: SEQ ID NO:122:

UGUGUGGAAG GGNNNNUGNG UGGGGUUGGG                                                       30

( 2 ) INFORMATION FOR SEQ ID NO:123:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-$NH_2$ 2 cytosine ( i x ) FEATURE:
        ( D ) OTHER INFORMATION: All U's are 2'-$NH_2$ 2 uracil ( x i ) SEQUENCE DESCRIPTION: SEQ ID NO:123:

AUUGUGUGGG AUAGGGCAUA GAGGGUGUGG GAAACCCCAG ACCGGGGCGU                                 50

( 2 ) INFORMATION FOR SEQ ID NO:124:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-$NH_2$ 2 cytosine ( i x ) FEATURE:
        ( D ) OTHER INFORMATION: All U's are 2'-$NH_2$ 2 uracil ( x i ) SEQUENCE DESCRIPTION: SEQ ID NO:124:

UGUGUGGGAC AGCGGAUCAG GGGUGUGGGA GCGCAUAACA UCCUACNUGC                                 50

U                                                                                                          51

(2) INFORMATION FOR SEQ ID NO:125:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ix) FEATURE:
        (D) OTHER INFORMATION: All C's are 2'-$NH_2$ cytosine (ix) FEATURE:
        (D) OTHER INFORMATION: All U's are 2'-$NH_2$ uracil (xi) SEQUENCE DESCRIPTION: SEQ ID NO:125:

ANNNNUNUGC AUGUGUGGGA CAGGGUGCAU GUGGGUUGCG GGACCUUGGU                                                      50

(2) INFORMATION FOR SEQ ID NO:126:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ix) FEATURE:
        (D) OTHER INFORMATION: All C's are 2'-$NH_2$ cytosine (ix) FEATURE:
        (D) OTHER INFORMATION: All U's are 2'-$NH_2$ uracil (xi) SEQUENCE DESCRIPTION: SEQ ID NO:126:

UGUGUGGGAC AGGGNAUANA NGGGUGUGGG A                                                                         31

(2) INFORMATION FOR SEQ ID NO:127:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (D) OTHER INFORMATION: All C's are 2'-$NH_2$ cytosine (ix) FEATURE:
        (D) OTHER INFORMATION: All U's are 2'-$NH_2$ uracil (xi) SEQUENCE DESCRIPTION: SEQ ID NO:127:

GCAGGAGGAU AGGGAUCGGA UGGGGUAGGA                                                                           30

(2) INFORMATION FOR SEQ ID NO:128:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (D) OTHER INFORMATION: All C's are 2'-$NH_2$ cytosine (ix) FEATURE:
        (D) OTHER INFORMATION: All U's are 2'-$NH_2$ uracil (xi) SEQUENCE DESCRIPTION: SEQ ID NO:128:

UGAGGAUCGG AUGGGGAGCA GGCGGAGGAA                                                                           30

( 2 ) INFORMATION FOR SEQ ID NO:129:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ 2 cytosine ( i x ) FEATURE:
        ( D ) OTHER INFORMATION: All U's are 2'-NH$_2$ 2 uracil ( x i ) SEQUENCE DESCRIPTION: SEQ ID NO:129:

GUGGAUUGGA AGGGGUGCUG GAGGAGGACG        30

( 2 ) INFORMATION FOR SEQ ID NO:130:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ 2 cytosine ( i x ) FEATURE:
        ( D ) OTHER INFORMATION: All U's are 2'-NH$_2$ 2 uracil ( x i ) SEQUENCE DESCRIPTION: SEQ ID NO:130:

UAGGAAUGGA UGGGGUUGGA ACAGAGUUCU AAUGUCGACC UCACAUGUGG        50

( 2 ) INFORMATION FOR SEQ ID NO:131:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ 2 cytosine ( i x ) FEATURE:
        ( D ) OTHER INFORMATION: All U's are 2'-NH$_2$ 2 uracil ( x i ) SEQUENCE DESCRIPTION: SEQ ID NO:131:

CAGGAAUGGA UGGGGUUGGA ACAGAGUUCU AAUGUCGACC UCACAUGCGU        50

( 2 ) INFORMATION FOR SEQ ID NO:132:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ 2 cytosine ( i x ) FEATURE:
        ( D ) OTHER INFORMATION: All U's are 2'-NH$_2$ 2 uracil ( x i ) SEQUENCE DESCRIPTION: SEQ ID NO:132:

CAGGAUAGGA UGGGGUCGGA ACCGUGUAUC AUAACGAGUC AUCUCCUGGU        50

( 2 ) INFORMATION FOR SEQ ID NO:133:

( i ) SEQUENCE CHARACTERISTICS:

(A) LENGTH: 14 base pairs
                (B) TYPE: nucleic acid
                (C) STRANDEDNESS: single
                (D) TOPOLOGY: linear (ix) FEATURE:
                (D) OTHER INFORMATION: All C's are 2'-NH$_2$ 2 cytosine (ix) FEATURE:
                (D) OTHER INFORMATION: All U's are 2'-NH$_2$ 2 uracil (xi) SEQUENCE DESCRIPTION: SEQ ID NO:133:

GGAUHGGAUG GGGU                                                                         14

(2) INFORMATION FOR SEQ ID NO:134:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (ix) FEATURE:
                (D) OTHER INFORMATION: All C's are 2'-NH$_2$ 2 cytosine (ix) FEATURE:
                (D) OTHER INFORMATION: All U's are 2'-NH$_2$ 2 uracil (xi) SEQUENCE DESCRIPTION: SEQ ID NO:134:

UUAACGGCGU GGUCCGAGGG UGGCGAGUAC                                                         30

(2) INFORMATION FOR SEQ ID NO:135:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (ix) FEATURE:
                (D) OTHER INFORMATION: All C's are 2'-NH$_2$ 2 cytosine (ix) FEATURE:
                (D) OTHER INFORMATION: All U's are 2'-NH$_2$ 2 uracil (xi) SEQUENCE DESCRIPTION: SEQ ID NO:135:

GACUAGGCGC GGACCGUGGG UGGUGAGUGG                                                         30

(2) INFORMATION FOR SEQ ID NO:136:

(i) SEQUENCE CHARACTERISTICS:
                (A) LENGTH: 47 base pairs
                (B) TYPE: nucleic acid
                (C) STRANDEDNESS: single
                (D) TOPOLOGY: linear (ix) FEATURE:
                (D) OTHER INFORMATION: All C's are 2'-NH$_2$ 2 cytosine (ix) FEATURE:
                (D) OTHER INFORMATION: All U's are 2'-NH$_2$ 2 uracil (xi) SEQUENCE DESCRIPTION: SEQ ID NO:136:

AGUGGCAUGG GCCGUGGGAG GUGAGUGUCG AGACUGGUGU UGGGCCU                                      47

(2) INFORMATION FOR SEQ ID NO:137:

(i) SEQUENCE CHARACTERISTICS:
                (A) LENGTH: 49 base pairs
                (B) TYPE: nucleic acid
                (C) STRANDEDNESS: single (D) TOPOLOGY: linear (ix) FEATURE:
(D) OTHER INFORMATION: All C's are 2'-NH₂ 2 cytosine (ix) FEATURE:
(D) OTHER INFORMATION: All U's are 2'-NH₂ 2 uracil (xi) SEQUENCE DESCRIPTION: SEQ ID NO:137:

CGUGGUUCCG UGGGUGGUGA GAUGAGACUU AAUCAGUUCG UAGACCGGU 49

(2) INFORMATION FOR SEQ ID NO:138:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(D) OTHER INFORMATION: All C's are 2'-NH₂ 2 cytosine (ix) FEATURE:
(D) OTHER INFORMATION: All U's are 2'-NH₂ 2 uracil (xi) SEQUENCE DESCRIPTION: SEQ ID NO:138:

CCGUGGGUGG UGAGU 15

(2) INFORMATION FOR SEQ ID NO:139:

(i) SEQUENCE CHARACTERISTICS:
(A) LENGTH: 50 base pairs
(B) TYPE: nucleic acid
(C) STRANDEDNESS: single
(D) TOPOLOGY: linear (ix) FEATURE:
(D) OTHER INFORMATION: All C's are 2'-NH₂ 2 cytosine (ix) FEATURE:
(D) OTHER INFORMATION: All U's are 2'-NH₂ 2 uracil (xi) SEQUENCE DESCRIPTION: SEQ ID NO:139:

NAAAUACGAG AGAGGANCAU ANNUGACUGA ACAUUGAUGU AUUAACGAGU 50

(2) INFORMATION FOR SEQ ID NO:140:

(i) SEQUENCE CHARACTERISTICS:
(A) LENGTH: 51 base pairs
(B) TYPE: nucleic acid
(C) STRANDEDNESS: single
(D) TOPOLOGY: linear (ix) FEATURE:
(D) OTHER INFORMATION: All C's are 2'-NH₂ 2 cytosine (ix) FEATURE:
(D) OTHER INFORMATION: All U's are 2'-NH₂ 2 uracil (xi) SEQUENCE DESCRIPTION: SEQ ID NO:140:

GAGGUACGAG AGAGGAGCGU AGGUGACUGA ACAUUGAUGU AUUAACGUGU 50
C 51

(2) INFORMATION FOR SEQ ID NO:141:

(i) SEQUENCE CHARACTERISTICS:
(A) LENGTH: 50 base pairs
(B) TYPE: nucleic acid
(C) STRANDEDNESS: single
(D) TOPOLOGY: linear ( i x ) FEATURE:
    ( D ) OTHER INFORMATION: All C's are 2'-NH$_2$ 2 cytosine ( i x ) FEATURE:
    ( D ) OTHER INFORMATION: All U's are 2'-NH$_2$ 2 uracil ( x i ) SEQUENCE DESCRIPTION: SEQ ID NO:141:

AGGGUGGCUG GGAGGACCCG CGGUGAAUCG GUAGCACAGU GAUGUUCGGU    50

( 2 ) INFORMATION FOR SEQ ID NO:142:

( i ) SEQUENCE CHARACTERISTICS:
    ( A ) LENGTH: 50 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-NH$_2$ 2 cytosine ( i x ) FEATURE:
    ( D ) OTHER INFORMATION: All U's are 2'-NH$_2$ 2 uracil ( x i ) SEQUENCE DESCRIPTION: SEQ ID NO:142:

GAGGGUGGCA GGGAGGACCC GCGGUGAAUC GGUAGCACAG UGAGUUCGGU    50

( 2 ) INFORMATION FOR SEQ ID NO:143:

( i ) SEQUENCE CHARACTERISTICS:
    ( A ) LENGTH: 30 base-pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-NH$_2$ 2 cytosine ( i x ) FEATURE:
    ( D ) OTHER INFORMATION: All U's are 2'-NH$_2$ 2 uracil ( x i ) SEQUENCE DESCRIPTION: SEQ ID NO:143:

CGCGAGGGCU GGCGGGGUAG GAUGGGUAGA    30

( 2 ) INFORMATION FOR SEQ ID NO:144:

( i ) SEQUENCE CHARACTERISTICS:
    ( A ) LENGTH: 50 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-NH$_2$ 2 cytosine ( i x ) FEATURE:
    ( D ) OTHER INFORMATION: All U's are 2'-NH$_2$ 2 uracil ( x i ) SEQUENCE DESCRIPTION: SEQ ID NO:144:

CGCGAGUGCU ACGAGGCGUG GGGGGGUGGA AACUAGUUGU GCUCUGGCCG    50

( 2 ) INFORMATION FOR SEQ ID NO:145:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i x ) FEATURE:
    ( D ) OTHER INFORMATION: All C's are 2'-NH$_2$ 2 cytosine ( i x ) FEATURE:
        ( D ) OTHER INFORMATION: All U's are 2'-NH$_2$ 2 uracil ( x i ) SEQUENCE DESCRIPTION: SEQ ID NO:145:

GAUUGGAAGC AGGGUGUGGG UUAGGAGGGC         30

( 2 ) INFORMATION FOR SEQ ID NO:146:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ 2 cytosine ( i x ) FEATURE:
        ( D ) OTHER INFORMATION: All U's are 2'-NH$_2$ 2 uracil ( x i ) SEQUENCE DESCRIPTION: SEQ ID NO:146:

GACCACAGUU UAAACGCCCA UCAGUGGUAG GGUGUGGGUA AGGAGGGCUG         50

( 2 ) INFORMATION FOR SEQ ID NO:147:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ 2 cytosine ( i x ) FEATURE:
        ( D ) OTHER INFORMATION: All U's are 2'-NH$_2$ 2 uracil ( x i ) SEQUENCE DESCRIPTION: SEQ ID NO:147:

CGCGAGGGCU GGCGGGGUAG GAUGGGUAGA         30

( 2 ) INFORMATION FOR SEQ ID NO:148:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ 2 cytosine ( i x ) FEATURE:
        ( D ) OTHER INFORMATION: All U's are 2'-NH$_2$ 2 uracil ( x i ) SEQUENCE DESCRIPTION: SEQ ID NO:148:

UGGGCCGCCG GUCUUGGGUG UAUGUGUGAA         30

( 2 ) INFORMATION FOR SEQ ID NO:149:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ 2 cytosine ( i x ) FEATURE:
        ( D ) OTHER INFORMATION: All U's are 2'-NH$_2$ 2 uracil ( x i ) SEQUENCE DESCRIPTION: SEQ ID NO:149:

AGUUGGGGGC UCGUGCGGCG UGGGGCGUGC                        30

( 2 ) INFORMATION FOR SEQ ID NO:150:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-$NH_2$ 2 cytosine ( i x ) FEATURE:
        ( D ) OTHER INFORMATION: All U's are 2'-$NH_2$ 2 uracil ( x i ) SEQUENCE DESCRIPTION: SEQ ID NO:150:

GGGAUGGUUG GAGACCGGGA GAUGGGAGGA                        30

( 2 ) INFORMATION FOR SEQ ID NO:151:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-$NH_2$ 2 cytosine ( i x ) FEATURE:
        ( D ) OTHER INFORMATION: All U's are 2'-$NH_2$ 2 uracil ( x i ) SEQUENCE DESCRIPTION: SEQ ID NO:151:

AAACGGGGCG AUGGAAAGUG UGGGGUACGA                        30

( 2 ) INFORMATION FOR SEQ ID NO:152:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-$NH_2$ 2 cytosine ( i x ) FEATURE:
        ( D ) OTHER INFORMATION: All U's are 2'-$NH_2$ 2 uracil ( x i ) SEQUENCE DESCRIPTION: SEQ ID NO:152:

GAGGAGGAUG GAGAGGAGCG GUGUGCAGGG                        30

( 2 ) INFORMATION FOR SEQ ID NO:153:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-$NH_2$ 2 cytosine ( i x ) FEATURE:
        ( D ) OTHER INFORMATION: All U's are 2'-$NH_2$ 2 uracil ( x i ) SEQUENCE DESCRIPTION: SEQ ID NO:153:

GAGAGGGUGA AGUGGGCAGG AUGGGGUAGG                                               30

( 2 ) INFORMATION FOR SEQ ID NO:154:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ 2 cytosine ( i x ) FEATURE:
        ( D ) OTHER INFORMATION: All U's are 2'-NH$_2$ 2 uracil ( x i ) SEQUENCE DESCRIPTION: SEQ ID NO:154:

CUGAAAUUGC GGGUGUGGAG GUAUGCUGGG AAAGGUGGAU GGUACACGU                         49

( 2 ) INFORMATION FOR SEQ ID NO:155:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ 2 cytosine ( i x ) FEATURE:
        ( D ) OTHER INFORMATION: All U's are 2'-NH$_2$ 2 uracil ( x i ) SEQUENCE DESCRIPTION: SEQ ID NO:155:

CAAUGUUUGG AGUCUGCUAA UGUGGGUGGG UUAGACGUAC CGAUGGUIJGC                       50

( 2 ) INFORMATION FOR SEQ ID NO:156:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ 2 cytosine ( i x ) FEATURE:
        ( D ) OTHER INFORMATION: All U's are 2'-NH$_2$ 2 uracil ( x i ) SEQUENCE DESCRIPTION: SEQ ID NO:156:

ACGGGGAAGU ACGAGAGCGG ACUGUAAGUC UAGUGGGUCA GUUCGGUG                          48

( 2 ) INFORMATION FOR SEQ ID NO:157:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ 2 cytosine ( i x ) FEATURE:
        ( D ) OTHER INFORMATION: All U's are 2'-NH$_2$ 2 uracil ( x i ) SEQUENCE DESCRIPTION: SEQ ID NO:157:

UUCAGCGCGC AUUAGUGCAG CGGGUUCAAC AAAAGAGGUG UUCGUGUGUG                        50

( 2 ) INFORMATION FOR SEQ ID NO:158:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ 2 cytosine ( i x ) FEATURE:
        ( D ) OTHER INFORMATION: All U's are 2'-NH$_2$ 2 uracil ( x i ) SEQUENCE DESCRIPTION: SEQ ID NO:158:

CGGAUUGUGU GGUCGGGAGG GCAGUAGUUU ACACUCACCC GUGGUCUGCU    50

( 2 ) INFORMATION FOR SEQ ID NO:159:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ 2 cytosine ( i x ) FEATURE:
        ( D ) OTHER INFORMATION: All U's are 2'-NH$_2$ 2 uracil ( x i ) SEQUENCE DESCRIPTION: SEQ ID NO:159:

GGUGUGUGAC AAUGUGCGUG GGUUGGGCAG GUACAAAGCG UAUGGGCGUG    50

( 2 ) INFORMATION FOR SEQ ID NO:160:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ 2 cytosine ( i x ) FEATURE:
        ( D ) OTHER INFORMATION: All U's are 2'-NH$_2$ 2 uracil ( x i ) SEQUENCE DESCRIPTION: SEQ ID NO:160:

AACGGGAGGU ACGAGAGCGG GAGCGCAUAA AUAGGAAACU CCUUGCACGU    50

( 2 ) INFORMATION FOR SEQ ID NO:161:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ 2 cytosine ( i x ) FEATURE:
        ( D ) OTHER INFORMATION: All U's are 2'-NH$_2$ 2 uracil ( x i ) SEQUENCE DESCRIPTION: SEQ ID NO:161:

AGGCAGUAUU GGGGGUGGUC AGCGCCUCCC CAAAACUCGC ACCUUAGCCC    50

( 2 ) INFORMATION FOR SEQ ID NO:162:

( i ) SEQUENCE CHARACTERISTICS:

( A ) LENGTH: 50 base pairs
( B ) TYPE: nucleic acid
( C ) STRANDEDNESS: single
( D ) TOPOLOGY: linear ( i x ) FEATURE:
( D ) OTHER INFORMATION: All C's are 2'-NH₂ 2 cytosine ( i x ) FEATURE:
( D ) OTHER INFORMATION: All U's are 2'-NH₂ 2 uracil ( x i ) SEQUENCE DESCRIPTION: SEQ ID NO:162:

GGGUUGGGUG GCAAGCGGAG AGCAGGGUUA GGUGCGGACU CAUUGGUGUG     50

( 2 ) INFORMATION FOR SEQ ID NO:163:

( i ) SEQUENCE CHARACTERISTICS:
( A ) LENGTH: 50 base pairs
( B ) TYPE: nucleic acid
( C ) STRANDEDNESS: single
( D ) TOPOLOGY: linear ( i x ) FEATURE:
( D ) OTHER INFORMATION: All C's are 2'-NH₂ 2 cytosine ( i x ) FEATURE:
( D ) OTHER INFORMATION: All U's are 2'-NH₂ 2 uracil ( x i ) SEQUENCE DESCRIPTION: SEQ ID NO:163:

GGAGGGCAG GUUCGAUGCG GGAGCGACUG ACCACGAGAA AUGUGCGGGU     50

( 2 ) INFORMATION FOR SEQ ID NO:164:

( i ) SEQUENCE CHARACTERISTICS:
( A ) LENGTH: 50 base pairs
( B ) TYPE: nucleic acid
( C ) STRANDEDNESS: single
( D ) TOPOLOGY: linear ( i x ) FEATURE:
( D ) OTHER INFORMATION: All C's are 2'-NH₂ 2 cytosine ( i x ) FEATURE:
( D ) OTHER INFORMATION: All U's are 2'-NH₂ 2 uracil ( x i ) SEQUENCE DESCRIPTION: SEQ ID NO:164:

CUCAGCAUCC AGGAAGGGGA CUUGGUAGGG CACCAUCGAG AUCUUGGCGU     50

( 2 ) INFORMATION FOR SEQ ID NO:165:

( i ) SEQUENCE CHARACTERISTICS:
( A ) LENGTH: 50 base pairs
( B ) TYPE: nucleic acid
( C ) STRANDEDNESS: single
( D ) TOPOLOGY: linear ( i x ) FEATURE:
( D ) OTHER INFORMATION: All C's are 2'-NH₂ 2 cytosine ( i x ) FEATURE:
( D ) OTHER INFORMATION: All U's are 2'-NH₂ 2 uracil ( x i ) SEQUENCE DESCRIPTION: SEQ ID NO:165:

ACCCUAGGCA UCCAGGUUGG GGAUAGCGGU UGGAGUGAAU GUGUUGUGCC     50

( 2 ) INFORMATION FOR SEQ ID NO:166:

( i ) SEQUENCE CHARACTERISTICS:
( A ) LENGTH: 30 base pairs
( B ) TYPE: nucleic acid
( C ) STRANDEDNESS: single (D) TOPOLOGY: linear (ix) FEATURE:
(D) OTHER INFORMATION: All C's are 2'-NH$_2$ 2 cytosine (ix) FEATURE:
(D) OTHER INFORMATION: All U's are 2'-NH$_2$ 2 uracil (xi) SEQUENCE DESCRIPTION: SEQ ID NO:166:

CACGGAGGAG GAGGUCAGAC UUAGCGGUCA 30

(2) INFORMATION FOR SEQ ID NO:167:

(i) SEQUENCE CHARACTERISTICS:
(A) LENGTH: 30 base pairs
(B) TYPE: nucleic acid
(C) STRANDEDNESS: single
(D) TOPOLOGY: linear (ix) FEATURE:
(D) OTHER INFORMATION: All C's are 2'-NH$_2$ 2 cytosine (ix) FEATURE:
(D) OTHER INFORMATION: All U's are 2'-NH$_2$ 2 uracil (xi) SEQUENCE DESCRIPTION: SEQ ID NO:167:

UACAGGGGAA GGAGNGAAUU GCAAGAUGAA 30

(2) INFORMATION FOR SEQ ID NO:168:

(i) SEQUENCE CHARACTERISTICS:
(A) LENGTH: 30 base pairs
(B) TYPE: nucleic acid
(C) STRANDEDNESS: single
(D) TOPOLOGY: linear (ix) FEATURE:
(D) OTHER INFORMATION: All C's are 2'-NH$_2$ 2 cytosine (ix) FEATURE:
(D) OTHER INFORMATION: All U's are 2'-NH$_2$ 2 uracil (xi) SEQUENCE DESCRIPTION: SEQ ID NO:168:

AAAGUUGUGU GGAAGACAGU GGGAGGUGAA 30

(2) INFORMATION FOR SEQ ID NO:169:

(i) SEQUENCE CHARACTERISTICS:
(A) LENGTH: 30 base pairs
(B) TYPE: nucleic acid
(C) STRANDEDNESS: single
(D) TOPOLOGY: linear (ix) FEATURE:
(D) OTHER INFORMATION: All C's are 2'-NH$_2$ 2 cytosine (ix) FEATURE:
(D) OTHER INFORMATION: All U's are 2'-NH$_2$ 2 uracil (xi) SEQUENCE DESCRIPTION: SEQ ID NO:169:

UGAUGGCGGU AGUGGAGGUA AUGAGCGUNA 30

(2) INFORMATION FOR SEQ ID NO:170:

(i) SEQUENCE CHARACTERISTICS:
(A) LENGTH: 30 base pairs
(B) TYPE: nucleic acid
(C) STRANDEDNESS: single
(D) TOPOLOGY: linear (ix) FEATURE:

(D) OTHER INFORMATION: All C's are 2'-NH₂ 2 cytosine (ix) FEATURE:
(D) OTHER INFORMATION: All U's are 2'-NH₂ 2 uracil (xi) SEQUENCE DESCRIPTION: SEQ ID NO:170:

UAGGAGGUUG GAGGAAAGCU UCACAGCCGA                30

(2) INFORMATION FOR SEQ ID NO:171:

(i) SEQUENCE CHARACTERISTICS:
(A) LENGTH: 30 base pairs
(B) TYPE: nucleic acid
(C) STRANDEDNESS: single
(D) TOPOLOGY: linear (ix) FEATURE:
(D) OTHER INFORMATION: All C's are 2'-NH₂ 2 cytosine (ix) FEATURE:
(D) OTHER INFORMATION: All U's are 2'-NH₂ 2 uracil (xi) SEQUENCE DESCRIPTION: SEQ ID NO:171:

UGAGGAGGAG GAGGACAGGA UUCAACGAGU                30

(2) INFORMATION FOR SEQ ID NO:172:

(i) SEQUENCE CHARACTERISTICS:
(A) LENGTH: 30 base pairs
(B) TYPE: nucleic acid
(C) STRANDEDNESS: single
(D) TOPOLOGY: linear (ix) FEATURE:
(D) OTHER INFORMATION: All C's are 2'-NH₂ 2 cytosine (ix) FEATURE:
(D) OTHER INFORMATION: All U's are 2'-NH₂ 2 uracil (xi) SEQUENCE DESCRIPTION: SEQ ID NO:172:

GUUAGGAGGG UGGAGGUUCG AGUGUGGCAA                30

(2) INFORMATION FOR SEQ ID NO:173:

(i) SEQUENCE CHARACTERISTICS:
(A) LENGTH: 30 base pairs
(B) TYPE: nucleic acid
(C) STRANDEDNESS: single
(D) TOPOLOGY: linear (ix) FEATURE:
(D) OTHER INFORMATION: All C's are 2'-NH₂ 2 cytosine (ix) FEATURE:
(D) OTHER INFORMATION: All U's are 2'-NH₂ 2 uracil (xi) SEQUENCE DESCRIPTION: SEQ ID NO:173:

CGUCGAGUGC GAUGGAGGAG GAGGGAUGCA                30

(2) INFORMATION FOR SEQ ID NO:174:

(i) SEQUENCE CHARACTERISTICS:
(A) LENGTH: 30 base pairs
(B) TYPE: nucleic acid
(C) STRANDEDNESS: single
(D) TOPOLOGY: linear (ix) FEATURE:
(D) OTHER INFORMATION: All C's are 2'-NH₂ 2 cytosine (ix) FEATURE:

( D ) OTHER INFORMATION: All U's are 2'-NH₂ 2 uracil ( x i ) SEQUENCE DESCRIPTION: SEQ ID NO:174:

GGGGUCAAGG ACAGUGGGUG GUGGUGGUGU                30

( 2 ) INFORMATION FOR SEQ ID NO:175:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH₂ 2 cytosine ( i x ) FEATURE:
        ( D ) OTHER INFORMATION: All U's are 2'-NH₂ 2 uracil ( x i ) SEQUENCE DESCRIPTION: SEQ ID NO:175:

GGAGGGAGGA GGGAUGAUGA GCUCAUCAGC                30

( 2 ) INFORMATION FOR SEQ ID NO:176:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH₂ 2 cytosine ( i x ) FEATURE:
        ( D ) OTHER INFORMATION: All U's are 2'-NH₂ 2 uracil ( x i ) SEQUENCE DESCRIPTION: SEQ ID NO:176:

CAAACAGGAG GGAAUGGAGG GNG                23

( 2 ) INFORMATION FOR SEQ ID NO:177:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH₂ 2 cytosine ( i x ) FEATURE:
        ( D ) OTHER INFORMATION: All U's are 2'-NH₂ 2 uracil ( x i ) SEQUENCE DESCRIPTION: SEQ ID NO:177:

AGGGGUGGUC GGUAAGCUCG GUGGUGGUGG                30

( 2 ) INFORMATION FOR SEQ ID NO:178:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH₂ 2 cytosine ( i x ) FEATURE:
        ( D ) OTHER INFORMATION: All U's are 2'-NH₂ 2 uracil ( x i ) SEQUENCE DESCRIPTION: SEQ ID NO:178:

AGGAGGGUUA AGGAGGGAGA UUAAGCGUUG G     31

( 2 ) INFORMATION FOR SEQ ID NO:179:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ 2 cytosine ( i x ) FEATURE:
        ( D ) OTHER INFORMATION: All U's are 2'-NH$_2$ 2 uracil ( x i ) SEQUENCE DESCRIPTION: SEQ ID NO:179:

GUGGAGGGUA CGUGGAGGGG AGAGCGACA     29

( 2 ) INFORMATION FOR SEQ ID NO:180:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ 2 cytosine ( i x ) FEATURE:
        ( D ) OTHER INFORMATION: All U's are 2'-NH$_2$ 2 uracil ( x i ) SEQUENCE DESCRIPTION: SEQ ID NO:180:

AUAAUUCAAG GAGGUGGAGG ACAGAUGCGC     30

( 2 ) INFORMATION FOR SEQ ID NO:181:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ 2 cytosine ( i x ) FEATURE:
        ( D ) OTHER INFORMATION: All U's are 2'-NH$_2$ 2 uracil ( x i ) SEQUENCE DESCRIPTION: SEQ ID NO:181:

GAUGAGGACU CGGGGCGGAG GGUGGUACCA     30

( 2 ) INFORMATION FOR SEQ ID NO:182:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i x ) FEATURE:
        ( D ) OTHER INFORMATION: All C's are 2'-NH$_2$ 2 cytosine ( i x ) FEATURE:
        ( D ) OTHER INFORMATION: All U's are 2'-NH$_2$ 2 uracil ( x i ) SEQUENCE DESCRIPTION: SEQ ID NO:182:

AGGUCGUGGC UGGGAUUCGU CCUCGACAUG UACAUUGUGG CUCUGGUGCC     50

( 2 ) INFORMATION FOR SEQ ID NO:183:

( i ) SEQUENCE CHARACTERISTICS:
       ( A ) LENGTH: 43 base pairs
       ( B ) TYPE: nucleic acid
       ( C ) STRANDEDNESS: single
       ( D ) TOPOLOGY: linear ( i x ) FEATURE:
       ( D ) OTHER INFORMATION: All C's are 2'-NH$_2$ 2 cytosine ( i x ) FEATURE:
       ( D ) OTHER INFORMATION: All U's are 2'-NH$_2$ 2 uracil ( x i ) SEQUENCE DESCRIPTION: SEQ ID NO:183:

AAGUUAGUCA UCGUGCAAAC UGCGAGUGCA CUGCUCGGGA UCC    43

( 2 ) INFORMATION FOR SEQ ID NO:184:

( i ) SEQUENCE CHARACTERISTICS:
       ( A ) LENGTH: 50 base pairs
       ( B ) TYPE: nucleic acid
       ( C ) STRANDEDNESS: single
       ( D ) TOPOLOGY: linear ( i x ) FEATURE:
       ( D ) OTHER INFORMATION: All C's are 2'-NH$_2$ 2 cytosine ( i x ) FEATURE:
       ( D ) OTHER INFORMATION: All U's are 2'-NH$_2$ 2 uracil ( x i ) SEQUENCE DESCRIPTION: SEQ ID NO:184:

GACCACAGUU UAAACGCCCA UCAGUGGUAG GGUGUGGGUA AGGAGGGCUG    50

( 2 ) INFORMATION FOR SEQ ID NO:185:

( i ) SEQUENCE CHARACTERISTICS:
       ( A ) LENGTH: 50 base pairs
       ( B ) TYPE: nucleic acid
       ( C ) STRANDEDNESS: single
       ( D ) TOPOLOGY: linear ( i x ) FEATURE:
       ( D ) OTHER INFORMATION: All C's are 2'-NH$_2$ 2 cytosine ( i x ) FEATURE:
       ( D ) OTHER INFORMATION: All U's are 2'-NH$_2$ 2 uracil ( x i ) SEQUENCE DESCRIPTION: SEQ ID NO:185:

CGCGAGUGCU ACGAGGCGUG GGGGGGUGGA AACUAGUUGU GCUCUGGCCG    50

( 2 ) INFORMATION FOR SEQ ID NO:186:

( i ) SEQUENCE CHARACTERISTICS:
       ( A ) LENGTH: 26 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:186:

GGUGUGUGGA AGACAGCGGG UGGUUC    26

( 2 ) INFORMATION FOR SEQ ID NO:187:

( i ) SEQUENCE CHARACTERISTICS:
       ( A ) LENGTH: 27 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:187:

GGACGGCGUG GUCCGAGGGU GGCGAGU 27

( 2 ) INFORMATION FOR SEQ ID NO:188:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:188:

GGAGGACGAU GCGGAACGGG AGGUACGAGA GCGGGAGC 38

( 2 ) INFORMATION FOR SEQ ID NO:189:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:189:

GGGAGCUCAG AAUAAACGCU CAAUGCUAUU CGCCUAACUC GGCGCUCCUA 50

CCUUUCGACA UGAGGCCCGG AUCCGGC 77

( 2 ) INFORMATION FOR SEQ ID NO:190:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:190:

GGGAGCUCAG AAUAAACGCU CAAAUCUCCU CCCGUCGAAG CUAACCUGGC 50

CACUUCGACA UGAGGCCCGG AUCCGGC 77

( 2 ) INFORMATION FOR SEQ ID NO:191:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:191:

GGGAGCUCAG AAUAAACGCU CAAUCGGCGA GCUAACCAAG ACACUCGCUG 50

CACUUCGACA UGAGGCCCGG AUCCGGC 77

( 2 ) INFORMATION FOR SEQ ID NO:192:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:192:

GGGAGCUCAG AAUAAACGCU CAAGUAGCAC UAUCGGCCUA ACCCGGUAGC 50

UCCUUCGACA UGAGGCCCGG AUCCGGC 77

( 2 ) INFORMATION FOR SEQ ID NO:193:

( i ) SEQUENCE CHARACTERISTICS:
   ( A ) LENGTH: 77 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:193:

GGGAGCUCAG AAUAAACGCU CAAACCCGCG GCCUCCGAAG CUAACCAGGA    50

CACUUCGACA UGAGGCCCGG AUCCGGC    77

( 2 ) INFORMATION FOR SEQ ID NO:194:

( i ) SEQUENCE CHARACTERISTICS:
      ( A ) LENGTH: 77 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:194:

GGGAGCUCAG AAUAAACGCU CAAUGGGUGC UAACCAGGAC ACACCCACGC    50

UGUUUCGACA UGAGGCCCGG AUCCGGC    77

( 2 ) INFORMATION FOR SEQ ID NO:195:

( i ) SEQUENCE CHARACTERISTICS:
      ( A ) LENGTH: 77 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:195:

GGGAGCUCAG AAUAAACGCU CAACACGCAC AGCUAACCAA GCCACUGUGC    50

CCCUUCGACA UGAGGCCCGG AUCCGGC    77

( 2 ) INFORMATION FOR SEQ ID NO:196:

( i ) SEQUENCE CHARACTERISTICS:
      ( A ) LENGTH: 77 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:196:

GGGAGCUCAG AAUAAACGCU CAACUGCGUG GUAUAACCAC AUGCCCUGGG    50

CGAUUCGACA UGAGGCCCGG AUCCGGC    77

( 2 ) INFORMATION FOR SEQ ID NO:197:

( i ) SEQUENCE CHARACTERISTICS:
      ( A ) LENGTH: 77 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:197:

GGGAGCUCAG AAUAAACGCU CAAUGGGUGC UUAACCAGGC CACACCCUGC    50

UGUUUCGACA UGAGGCCCGG AUCCGGC    77

( 2 ) INFORMATION FOR SEQ ID NO:198:

( i ) SEQUENCE CHARACTERISTICS:
      ( A ) LENGTH: 77 base pairs
      ( B ) TYPE: nucleic acid ( C ) STRANDEDNESS: single
( D ) TOPOLOGY: linear ( x i ) SEQUENCE DESCRIPTION: SEQ ID NO:198:

GGGAGCUCAG AAUAAACGCU CAACUAGGUG CUAUCCAGGA CUCUCCUGG  50

UCCUUCGACA UGAGGCCCGG AUCCGGC  77

( 2 ) INFORMATION FOR SEQ ID NO:199:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:199:

GGGAGCUCAG AAUAAACGCU CAAUGCUAUU CGCCUAGCUC GGCGCUCCUA  50

CCUUUCGACA UGAGGCCCGG AUCCGGC  77

( 2 ) INFORMATION FOR SEQ ID NO:200:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:200:

GGGAGCUCAG AAUAAACGCU CAAAGCUAUU CGCCCAACCC GGCGCUCCCG  50

ACCUUCGACA UGAGGCCCGG AUCCGGC  77

( 2 ) INFORMATION FOR SEQ ID NO:201:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:201:

GGGAGCUCAG AAUAAACGCU CAAACCAGCU GCGUGCAACC GCACAUGCCU  50

GGUUCGACAU GAGGCCCGGA UCCGGC  76

( 2 ) INFORMATION FOR SEQ ID NO:202:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:202:

GGGAGCUCAG AAUAAACGCU CAACAGGCCC CGUCGUAAGC UAACCUGGAC  50

CCUUUCGACA UGAGGCCCGG AUCCGGC  77

( 2 ) INFORMATION FOR SEQ ID NO:203:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:203:

```
GGGAGCUCAG  AAUAAACGCU  CAAGGGUAAC  GUUGUGACAA  GUACACCUGC              50

GUCUUCGACA  UGAGGCCCGG  AUCCGGC                                         77
```

( 2 ) INFORMATION FOR SEQ ID NO:204:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:204:

```
GGGAGCUCAG  AAUAAACGCU  CAAGGGGCAA  CGCUACAGAC  AAGUGCACCC              50

AACUUCGACA  UGAGGCCCGG  AUCCGGC                                         77
```

( 2 ) INFORMATION FOR SEQ ID NO:205:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:205:

```
GGGAGCUCAG  AAUAAACGCU  CAACGUCAGA  AGGCAACGUA  UAGGCAAGCA              50

CACUUCGACA  UGAGGCCCGG  AUCCGGC                                         77
```

( 2 ) INFORMATION FOR SEQ ID NO:206:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:206:

```
GGGAGCUCAG  AAUAAACGCU  CAACCUCUCG  AAGACAACGC  UGUGACAAGA              50

CACUUCGACA  UGAGGCCCGG  AUCCGGA                                         77
```

( 2 ) INFORMATION FOR SEQ ID NO:207:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:207:

```
GGGAGCUCAG  AAUAAACGCU  CAAAGUGGGA  AACGCUACUU  GACAAGACAC              50

CACUUCGACA  UGAGGCCCGG  AUCCGGC                                         77
```

( 2 ) INFORMATION FOR SEQ ID NO:208:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:208:

```
GGGAGCUCAG  AAUAAACGCU  CAAGGCUACG  CUAAUGACAA  GUGCACUUGG              50

GUGUUCGACA  UGAGGCCCGG  AUCCGGC                                         77
```

( 2 ) INFORMATION FOR SEQ ID NO:209:

( i ) SEQUENCE CHARACTERISTICS:
    ( A ) LENGTH: 79 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:209:

| | | | | |
|---|---|---|---|---|
| GGGAGAUGCC | UGUCGAGCAU | GCUGCUCUGG | UAACGCAAUG | UCAAGUGCAC | 50 |
| AUGAGUAGCU | AAACAGCUUU | GUCGACGGG | | | 79 |

( 2 ) INFORMATION FOR SEQ ID NO:210:

( i ) SEQUENCE CHARACTERISTICS:
    ( A ) LENGTH: 79 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:210:

GGGAGAUGCC UGUCGAGCAU GCUGAGCCGC AGGUAACGGA CCGGCGAGAC 50
CAUUGUAGCU AAACAGCLTUU GUCGACGGG 79

( 2 ) INFORMATION FOR SEQ ID NO:211:

( i ) SEQUENCE CHARACTERISTICS:
    ( A ) LENGTH: 79 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:211:

GGGAGAUGCC UGUCGAGCAU GCUGACGAGC UUCGUAACGC UAUCGACAAG 50
UGCAGUAGCU AAACAGCUUU GUCGACGGG 79

( 2 ) INFORMATION FOR SEQ ID NO:212:

( i ) SEQUENCE CHARACTERISTICS:
    ( A ) LENGTH: 79 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:212:

GGGAGAUGCC UGUCGAGCAU GCUGAAGGGG AAACGUUGAG UCCGGUACAC 50
CCUGGUAGCU AAACAGCLTUU GUCGACGGG 79

( 2 ) INFORMATION FOR SEQ ID NO:213:

( i ) SEQUENCE CHARACTERISTICS:
    ( A ) LENGTH: 79 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:213:

GGGAGAUGCC UGUCGAGCAU GCUGAGGGUA ACGUACUGGC AAGCUCACCU 50
CAGCGUAGCU AAACAGCUUU GUCGACGGG 79

( 2 ) INFORMATION FOR SEQ ID NO:214:

( i ) SEQUENCE CHARACTERISTICS:
( A ) LENGTH: 79 base pairs
( B ) TYPE: nucleic acid
( C ) STRANDEDNESS: single
( D ) TOPOLOGY: linear ( x i ) SEQUENCE DESCRIPTION: SEQ ID NO:214:

| GGGAGAUGCC | UGUCGAGCAU | GCUGGAGGUA | ACGUACGACA | AGACCACUCC | 50 |
| AACUGUAGCU | AAACAGCUUU | GUCGACGGG | | | 79 |

( 2 ) INFORMATION FOR SEQ ID NO:215:

( i ) SEQUENCE CHARACTERISTICS:
( A ) LENGTH: 79 base pairs
( B ) TYPE: nucleic acid
( C ) STRANDEDNESS: single
( D ) TOPOLOGY: linear ( x i ) SEQUENCE DESCRIPTION: SEQ ID NO:215:

| GGGAGAUGCC | UGUCGAGCAU | GCUGAGGUAA | CGCUGAGUCA | AGUGCACUCG | 50 |
| ACAUGUAGCU | AAACAGCUUU | GUCGACGGG | | | 79 |

( 2 ) INFORMATION FOR SEQ ID NO:216:

( i ) SEQUENCE CHARACTERISTICS:
( A ) LENGTH: 79 base pairs
( B ) TYPE: nucleic acid
( C ) STRANDEDNESS: single
( D ) TOPOLOGY: linear ( x i ) SEQUENCE DESCRIPTION: SEQ ID NO:216:

| GGGAGAUGCC | UGUCGAGCAU | GCUGGGGAAA | CGCUAUCGAC | GAGUGCACCC | 50 |
| GGCAGUAGCU | AAACAGCUUU | GUCGACGGG | | | 79 |

( 2 ) INFORMATION FOR SEQ ID NO:217:

( i ) SEQUENCE CHARACTERISTICS:
( A ) LENGTH: 79 base pairs
( B ) TYPE: nucleic acid
( C ) STRANDEDNESS: single
( D ) TOPOLOGY: linear ( x i ) SEQUENCE DESCRIPTION: SEQ ID NO:217:

| GGGAGAUGCC | UGUCGAGCAU | GCUGCCGAGG | GUAACGUUGG | GUCAAGCACA | 50 |
| CCUCGUAGCU | AAACAGCUUU | GUCGACGGG | | | 79 |

( 2 ) INFORMATION FOR SEQ ID NO:218:

( i ) SEQUENCE CHARACTERISTICS:
( A ) LENGTH: 79 base pairs
( B ) TYPE: nucleic acid
( C ) STRANDEDNESS: single
( D ) TOPOLOGY: linear ( x i ) SEQUENCE DESCRIPTION: SEQ ID NO:218:

| GGGAGAUGCC | UGUCGAGCAU | GCUGUCGGGG | UAACGUAUUG | GCAAGGCACC | 50 |
| CGACGUAGCU | AAACAGCUUU | GUCGACGGG | | | 79 |

( 2 ) INFORMATION FOR SEQ ID NO:219:

( i ) SEQUENCE CHARACTERISTICS:
( A ) LENGTH: 79 base pairs
( B ) TYPE: nucleic acid
( C ) STRANDEDNESS: single (D) TOPOLOGY: linear (xi) SEQUENCE DESCRIPTION: SEQ ID NO:219:

```
GGGAGAUGCC UGUCGAGCAU GCUGGGUAAC GCUGUGGACA AGUGCACCAG        50
CUGCGUAGCU AAACAGCUUU GUCGACGGG                               79
```

(2) INFORMATION FOR SEQ ID NO:220:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:220:

```
GGGAGAUGCC UGUCGAGCAU GCUGAGGGUA ACGUACUGGC AAGCUCACCU        50
CAGCGUAGCU AAACAGCUUU GUCGACGGG                               79
```

(2) INFORMATION FOR SEQ ID NO:221:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:221:

```
GGGAGAUGCC UGUCGAGCAU GCUGAGGGUA ACGUAUAGUC AAGACACCUC        50
AAGUGUAGCU AAACAGCUUU GUCGACGGG                               79
```

(2) INFORMATION FOR SEQ ID NO:222:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:222:

```
GGGAGAUGCC UGUCGAGCAU GCUGGGGUAA CGCAUUGGCA AGACACCCAG        50
CCCCGUAGCU AAACAGCUUU GUCGAC&GG                               79
```

(2) INFORMATION FOR SEQ ID NO:223:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:223:

```
GGGAGAUGCC UGUCGAGCAU GCUGGAGGAA ACGUACCGUC GAGCCACUCC        50
AUGCGUAGCU AAACAGCUUU GUCGACGG                                79
```

(2) INFORMATION FOR SEQ ID NO:224:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (xi) SEQUENCE DESCRIPTION: SEQ ID NO:224:

-continued

GGGAGAUGCC UGUCGAGCAU GCUGAGGUAA CGCUGAGUCA AGUGCACUCG 50

ACAUGUAGCU AAACAGCUUU GUCGACGGG 79

( 2 ) INFORMATION FOR SEQ ID NO:225:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:225:

GGGAGAUGCC UGUCGAGCAU GCUGGGGUAA CGUGUGACAA GAUCACCCAG 50

UUUGGUAGCU AAACAGCUUU GUCGACGGG 79

( 2 ) INFORMATION FOR SEQ ID NO:226:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:226:

GGGAGAUGCC UGUCGAGCAU GCUGCACAGG GCAACGCUGC UGACAAGUGC 50

ACCUGUAGCU AAACAGCUUU GUCGACGGG 79

( 2 ) INFORMATION FOR SEQ ID NO:227:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:227:

GGGAGCUCAG AAUAAACGCU CAAUGGGUGC UAACCACCAC ACACUCACGC 50

UGUUUCGACA UGAGGCCCGG AUCCGGC 77

TABLE I

OLIGONUCLEOTIDES USED IN SELEX EXPERIMENTS A AND B.

| | SEQUENCE 5'-3' | SEQ ID NUMBER |
|---|---|---|
| EXPERIMENT A | | |
| Starting RNA | GGGAGCUCAGAAUAAACGCUCAANNNNNNN NNNNNNNNNNNNNNNNNNNNNNNUUCGACA UGAGGCCCGGAUCCGGC | SEQ ID NO: 1 |
| PCR Primer 1 | <u>HindIII</u><br>CCGAAGCTTAATACGACTCACTATAGGGAG<br>              T7 Promoter<br>CTCAGAATAAACGCTCAA | SEQ ID NO: 2 |
| PCR Primer 2 | <u>BamH1</u><br>GCCGGATCCGGGCCTCATGTCGAA | SEQ ID NO: 3 |
| EXPERIMENT B | | |
| Starting RNA | GGGAGAUGCCUGUCGAGCAUGCUGNNNNNNN NNNNNNNNNNNNNNNNNNNNNNNGUAGCUAA ACAGCUUUGUCGACGGG | SEQ ID NO: 4 |

TABLE I-continued

OLIGONUCLEOTIDES USED IN SELEX EXPERIMENTS A AND B.

| | SEQUENCE 5'-3' | SEQ ID NUMBER |
|---|---|---|
| PCR Primer 1 | HindIII<br>CCCGAAGCTT AATACGACTCACTATAGGGAG<br>T7 Promoter<br>ATGCCTGTCGAGCATGCTG | SEQ ID NO: 5 |
| PCR Primer 2 | SalI<br>CCCGTCGACAAAGCTGTTTAGCTAC | SEQ ID NO: 6 |

TABLE II

FAMILY 1 SEQUENCES OF THE RANDOM REGION FROM SELIX EXPERIMENT A AND B.

| FAMILY 1 | CONSENSUS SEQUENCE<br>CUAACCNGG (SEQ ID NO: 7) | SEQ ID NUMBER |
|---|---|---|
| 4A | UGCUAUUCGCCUAACUCGGCGCUCCUACCU | SEQ ID NO: 8 |
| 5A | AUCUCCUCCCGUCGAAGCUAACCUGGCCAC | SEQ ID NO: 9 |
| 7A | UCGGCGAGCUAACCAAGACACUCGCUGCAC | SEQ ID NO: 10 |
| 10A | GUAGCACUAUCGGCCUAACCCGGUAGCUCC | SEQ ID NO: 11 |
| 13A | ACCCGCGGCCUCCGAAGCUAACCAGGACAC | SEQ ID NO: 12 |
| 14A | UGGGUGCUAACCAGGACACACCCACGCUGU | SEQ ID NO: 13 |
| 16A | CACGCACAGCUAACCAAGCCACUGUGCCCC | SEQ ID NO: 14 |
| 18A | CUGCGUGGUAUAACCACAUGCCCUGGGCGA | SEQ ID NO: 15 |
| 21A | UGGGUGCUUAACCAGGCCACACCCUGCUGU | SEQ ID NO: 16 |
| 25A | CUAGGUGCUAUCCAGGACUCUCCCUGGUCC | SEQ ID NO: 17 |
| 29A | UGCUAUUCGCCUAGCUCGGCGCUCCUACCU | SEQ ID NO: 18 |
| 38A | AGCUAUUCGCCCAACCCGGCGCUCCCGACC | SEQ ID NO: 19 |
| 39A | ACCAGCUGCGUGCAACCGCACAUGCCUGG | SEQ ID NO: 20 |
| 56A | CAGGCCCCGUCGUAAGCUAACCUGGACCCU | SEQ ID NO: 21 |
| 61A | UGGGUGCUAACCACCACACACUCACGCUGU | SEQ ID NO: 22 |

TABLE III

FAMILY 2 SEQUENCES OF THE RANDOM REGION FROM SELEX EXPERIMENTS A AND B.

| FAMILY 2 | CONSENSUS SEQUENCE:<br>RRGGHAACGYWNNGDCAAGNNCACYY<br>(SEQ ID NO: 23) | SEQ ID NUMBER |
|---|---|---|
| 11A | GGGUAACGUUGUGACAAGUACACCUGCGUC | SEQ ID NO: 24 |
| 12A | GGGGCAACGCUACAGACAAGUGCACCCAAC | SEQ ID NO: 25 |
| 26A | CGUCAGAAGGCAACGUAUAGGCAAGCACAC | SEQ ID NO: 26 |
| 27A | CCUCUCGAAGACAACGCUGUGACAAGACAC | SEQ ID NO: 27 |
| 47A | AGUGGGAAACGCUACUUGACAAGACACCAC | SEQ ID NO: 28 |
| 65A | GGCUACGCUAAUGACAAGUGCACUUGGGUG | SEQ ID NO: 29 |
| 1B | CUCUGGUAACGCAAUGUCAAGUGCACAUGA | SEQ ID NO: 30 |
| 2B | AGCCGCAGGUAACGGACCGGCGAGACCAUU | SEQ ID NO: 31 |
| 6B | ACGAGCUUCGUAACGCUAUCGACAAGUGCA | SEQ ID NO: 32 |
| 8B | AAGGGGAAACGUUGAGUCCGGUACACCCUG | SEQ ID NO: 33 |
| 9B | AGGGUAACGUACUGGCAAGCUCACCUCAGC | SEQ ID NO: 34 |
| 11B | GAGGUAACGUACGACAAGACCACUCCAACU | SEQ ID NO: 35 |
| 12B | AGGUAACGCUGAGUCAAGUGCACUCGACAU | SEQ ID NO: 36 |
| 13B | GGGAAACGCUAUCGACGAGUGCACCCGGCA | SEQ ID NO: 37 |
| 14B | CCGAGGGUAACGUUGGGUCAAGCACACCUC | SEQ ID NO: 38 |
| 15B | UCGGGGUAACGUAUUGGCAAGGCACCCGAC | SEQ ID NO: 39 |
| 19B | GGUAACGCUGUGGACAAGUGCACCAGCUGC | SEQ ID NO: 40 |
| 22B | AGGGUAACGUACUGGCAAGCUCACCUCAGC | SEQ ID NO: 41 |
| 28B | AGGGUAACGUAUAGUCAAGACACCUCAAGU | SEQ ID NO: 42 |
| 29B | GGGUAACGCAUUGGCAAGACACCCAGCCCC | SEQ ID NO: 43 |
| 36B | GAGGAAACGUACCGUCGAGCCACUCCAUGC | SEQ ID NO: 44 |
| 38B | AGGUAACGCUGAGUCAAGUGCACUCGACAU | SEQ ID NO: 45 |
| 48B | GGGUAACGUGUGACAAGAUCACCCAGUUUG | SEQ ID NO: 46 |
| 49B | CACAGGGCAACGCUGCUGACAAGUGCACCU | SEQ ID NO: 47 |

TABLE IV

OTHER SEQUENCES OF THE RANDOM REGION FROM SELEX EXPERIMENTS A AND B.

| NUMBER | SEQUENCE | SEQ ID NUMBER |
|---|---|---|
| 8A | ACGCCAAGUGAGUCAGCAACAGAGCGUCCG | SEQ ID NO: 48 |
| 9A | CCAGUGAGUCCUGGUAAUCCGCAUCGGGCU | SEQ ID NO: 49 |
| 24A | CUUCAGAACGGCAUAGUGGUCGGCCGCGCC | SEQ ID NO: 50 |
| 33A | AGGUCACUGCGUCACCGUACAUGCCUGGCC | SEQ ID NO: 51 |
| 34A | UCCAACGAACGGCCCUCGUAUUCAGCCACC | SEQ ID NO: 52 |
| 36A | ACUGGAACCUGACGUAGUACAGCGACCCUC | SEQ ID NO: 53 |
| 37A | UCUCGCUGCGCCUACACGGCAUGCCGGGA | SEQ ID NO: 54 |
| 40A | GAUCACUGCGCAAUGCCUGCAUACCUGGUC | SEQ ID NO: 55 |
| 43A | UCUCGCUGCGCCUACACGGCAUGCCGGGA | SEQ ID NO: 56 |
| 44A | UGACCAGCUGCAUCCGACGAUAUACCCUGG | SEQ ID NO: 57 |
| 45A | GGCACACUCCAACGAGGUAACGUUACGGCG | SEQ ID NO: 58 |
| 55A | AGCGGAACGCCACGUAGUACGCCGACCCUC | SEQ ID NO: 59 |
| 4B | ACCCACGCCCGACAACCGAUGAGUUCUCGG | SEQ ID NO: 60 |
| 5B | UGCUUUGAAGUCCUCCCCGCCUCUCGAGGU | SEQ ID NO: 61 |
| 7B | AUGCUGAGGAUAUUGUGACCACUUCGGCGU | SEQ ID NO: 62 |
| 16B | ACCCACGCCCGACAACCGAUGAGCUCGGA | SEQ ID NO: 63 |
| 20B | AGUCCGGAUGCCCCACUGGGACUACAUUGU | SEQ ID NO: 64 |
| 21B | AAGUCCGAAUGCCACUGGGACUACCACUGA | SEQ ID NO: 65 |
| 23B | ACUCUCACUGCGAUUCGAAAUCAUGCCUGG | SEQ ID NO: 66 |
| 40B | AGGCUGGGUCACCGACAACUGCCCGCCAGC | SEQ ID NO: 67 |
| 42B | AGCCGCAGGUAACGGACCGGCGAGACCACU | SEQ ID NO: 68 |
| 26B | GCAUGAAGCGGAACUGUAGUACGCGAUCCA | SEQ ID NO: 69 |

TABLE V

REPEAT SEQUENCES OF THE RANDOM REGION FROM SELEX EXPERIMENTS A AND B.

| NUMBER | SEQUENCE | SEQUENCE ID NUMBER | CLONE REPEATED |
|---|---|---|---|
| 3A | GGGUAACGUUGUGACAAGUACACCUGCGUU | SEQ ID NO: 70 | 11A |
| 15A | GGGUAACGUUGUGACAAGUACACCUGCGUC | SEQ ID NO: 71 | 11A |
| 20A | GGGUAACGUUGUGACAAGUACACCUGCGUC | SEQ ID NO: 72 | 11A |
| 48A | GGGUAACGUUGUGACAACUACACCUGCGUC | SEQ ID NO: 73 | 11A |
| 58A | GGGUAACGUUGUGACAACUACACCUGCGUC | SEQ ID NO: 74 | 11A |
| 64A | GGGUAACGUUGUGACAACUACACCUGCGUC | SEQ ID NO: 75 | 11A |
| 28A | CGUCAGAAGGCAACGUAUAGGCAAGCACAC | SEQ ID NO: 76 | 26A |
| 30A | GUAGCACUAUCGGCCUAACCCGGUAGCUCC | SEQ ID NO: 77 | 10A |
| 23A | ACCCGCGGCCUCCGAAGCUAACCAGGACAC | SEQ ID NO: 78 | 13A |
| 46A | AGGUCACUGCGUCACCGUACAUGCCUGGCC | SEQ ID NO: 79 | 33A |
| 49A | AGGUCACUGCGUCACCGUACAUGCCUGGCC | SEQ ID NO: 80 | 33A |
| 50A | GGCACACUCCAACGAGGUAACGUUACGGCG | SEQ ID NO: 81 | 45A |
| 41A | GGGGCAACGCUACAGACAAGUGCACCCAAC | SEQ ID NO: 82 | 12A |
| 51A | GGGGCAACGCUACAGACAAGUGCACCCAAC | SEQ ID NO: 83 | 12A |
| 54A | GGGGCAACGCUACAGACAAGUGCACCCAAC | SEQ ID NO: 84 | 12A |
| 35A | UGGGUGCUAACCAGGACACACCCACGCUGU | SEQ ID NO: 85 | 14A |
| 18B | CCGAGGGUAACGUUGGGUCAAGCACACCUC | SEQ ID NO: 86 | 14B |
| 24B | GGGAAACGCUAUCGACGAGUGCACCCGGCA | SEQ ID NO: 87 | 13B |
| 39B | GGGAAACGCUAUCGACGAGUGCACCCGGCA | SEQ ID NO: 88 | 13B |
| 37B | ACUCUCACUGCGAUUCGAAAUCAUGCCUGG | SEQ ID NO: 89 | 23B |
| 43B | GCAUGAAGCGGAACUGUAGUACGCGAUCCA | SEQ ID NO: 90 | 26B |
| 46B | GCAUGAAGCGGAACUGUAGUACGCGAUCCA | SEQ ID NO: 91 | 26B |
| 25B | AGGGUAACGUACUGGCAAGCUCACCUCAGC | SEQ ID NO: 92 | 9B |
| 33B | AGGGUAACGUACUGGCAAGCUCACCUCAGC | SEQ ID NO: 93 | 9B |
| 31B | GGUAACGCUGUGGACAAGUGCACCAGCUGC | SEQ ID NO: 94 | 19B |

TABLE VI

SECONDARY STRUCTURES AND DISSOCIATION CONSTATNTS ($K_d$'s) FOR A REPRESENTATIVE SET OF HIGH-AFFINITY LIGANDS FROM FAMILY 1.

| LIGAND | STRUCTURE[a] | Kd, nM | SEQ ID. NO: (PARENT SEQUENCE) |
|---|---|---|---|
| 5A-t[b] | <pre>     CC              AA      
CCUC   GUCGAA --- GCU   C
ggag   cagcuu      CGG   C
  u a              CAC      U</pre> | 23 ± 3 | 190 |
| 7A-t[b] | <pre>               AA
CGGCGAG --- CU   C
GUCGCUC     GA   C
         ACA    A</pre> | 5.0 ± 0.5 | 191 |
| 13A-t[b] | <pre>     C                    A
CCG  GGCCUC ---- CGAAG ---- CU    A
ggc-ccggag       gcuuC     GA    C
        uaca          ACAG    C</pre> | 3.2 ± 0.5 | 193 |
| 14A-t[b] | <pre>       cucaa              A
aaa c g     UGGGUG --- CU  A
uuUGU-      -ACCCAC     GA  C
    CGC              ACAG    C</pre> | 3.0 ± 0.5 | 194 |
| 21A-t[b] | <pre>                  A
aa U ---- GGGU --- GCUU  A
uUG       CCCA     CGGA  C
     UCGU      CAC        C</pre> | 8.1 ± 0.8 | 197 |
| 25A-t[b] | <pre>                A
CUA -GGUG ---- CU   U
GGU  CCUC       GA  C
  C       UCAG    C</pre> | 5.9 ± 1.4 | 198 |
| 39A-t[b] | <pre>         CU        A
AACCAG    GC -- GUGC  A
u u GGUC -- CG    CACG  C
              UA      C</pre> | 8.5 ± 1.2 | 201 |

[a] Strongly conserved positions are shown in boldface symbols. Nucleotides in the constant region are in lowercase type.
[b] The letter "t" is used to designate truncated sequences derived from the corresponding parent sequences (FIG. 4).

TABLE VII

SECONDARY STRUCTURES AND DISSOCIATION CONSTANTS ($K_d$'s) FOR A REPRESENTATIVE SET OF HIGH-AFFINITY LIGANDS FROM FAMILY 2.

| LIGAND | STRUCTURE[a] | Kd, nM | SEQ ID NO. (PARENT SEQUENCE) |
|---|---|---|---|
| 12A-t[b] | ```
            CAACGCU
         G         A
                    C
   uc-aa - - - GGG  A
   ag uu     CCC    G
     c  CAA   A    A
            CGUGAAC
``` | 0.9 ± 0.2 | 204 |
| 26A-t[b] | ```
            CAACGUA
       A    G       U
      GUC  GAAG     A
      cag -cuuC     G
            A    G
            CACGAAC
``` | 0.4 ± 0.1 | 205 |
| 65A-t[b] | ```
             CUACGUA
          G         A
                     A
    aac g c u c a a G U
    uuGUGGGUUC         G
             A      A
             CGUGAAC
``` | 0.6 ± 0.04 | 208 |
| 22B-t[b] | ```
              UAACGUA
           G          C
   agc-aug c u g AGG   U
   ucg  ugCGACUCC      G
         a      A     G
              CUCGAAC
``` | 1 ± 0.6 | 220 |
| 28B-t[b] | ```
              UAACGUA
           G          U
   aug c  -u g AGG
   ugUG   ACUCC        A
          A    A    G
              CAGAACU
``` | 2 ± 1 | 221 |
| 38B-t[b] | ```
              UAACGCU
        c   G         G
   gca u g  u g AG     A
   ugUAC  GCUC         G
          A     A    U
              CGUGAAC
``` | 4 ± 1 | 224 |
| 2B-t[b] | ```
              UAACGCA
         C   G         C
       AGC  GCAG       C
       u c g  ug UU    G
           a    A     G
              CCAGAGC
``` | 170 ± 80 | 210 |

[a] Strongly conserved positions are shown in boldface symbols. Nucleotides in the constant region are in lowercase type.
[b] The letter "t" is used to designate truncated sequences derived from the corresponding patent sequences (FIG. 5).

TABLE VIII

2'-NH₂ RNA LIGANDS (RANDOM REGION) TO bFGF.

| | | SEQ ID NO: |
|---|---|---|
| FAMILY 1A | | |
| 14A | ACANGGAGUUGUGUGGAAGGCAGGGGGAGG | 101 |
| 15A | UGUGUGGAAGGCAGUGGGAGGUUCAGUGGU | 102 |
| 17A | AAAGUUGUGUGGAAGACAGUGGGAGGUGAA | 103 |
| 21A | GUAGACUAAUGUGUGGAAGACAGCGGGUGG | 104 |
| 29A | NNAGUUGUGUGGAAGACAGUGGGGGGUUGA | 105 |
| 38A | GGUGUGUNGAAGACAGUGGGUNGUUUAGNC | 106 |
| 49A | AUGGGUGUGGAAGACAGUGGGUGGUUGCA | 107 |
| 54A | ACUGUUGUGUGGAAGACAGCGGUGGUUGA | 108 |
| 60A | AAUGUAGGCUGUGUGUGUAGACAGUGGGUGG | 109 |
| 68A | GAUGUGGAGGGCAGUGGGGGUACCAUA | 110 |
| 74A | GGGGUCAAGGACAGUGGGGUGUGGUGU | 111 |
| 16B | UGCUGCGGUCGCAUGUGUGGAAGACAGAGGAGGUUAGAAUCAUGACGU | 112 |
| 31B | ACAGACCGUUGUGGAAGACAGUGGGAGGUUAUUAACGUAGAUCGCGC | 113 |
| 38B | GCUGCGGUCGCAUGUGUGGAAGACAGAGGAGGUUAGAAUCUGCCGC | 114 |
| 39B | GAAAACUACGGUGUGUGGAAGACAGUGGGCAGUCUGUGUCCGU | 115 |
| 62B | UCCAUCGUGGAAGACAGUGGGGAAGAAUCAGUCAGACGACUC | 116 |
| 79B | UGUGAUUGUGUGGAAGGCAGUGGGAGGUGCGAUGUAGAUCUGGCGAUG | 117 |
| | UGUGUGGAAGACAGUGGGWGGUU | 118 |

| | | |
|---|---|---|
| FAMILY 1B | | |
| 59A | UGUGUGGAAGGGUACCUGAGU----GGGGAUGGG | 119 |
| 82A | AAGACUGUGUGGAAGGGG---UGUA----GGGGUUGGG | 120 |
| 3B | UAGGGCCGCAACUGUGUGGAAGGGAGGAUGCGUCAUGGGGGUUGGGCUG | 121 |
| | UGUGUGGAAGGGNNNNUGNGU----GGGGUUGGG | 122 |

| | | |
|---|---|---|
| FAMILY 1C | | |
| 1B | AUUGUGUGGGAUAG-GGCAUGA-GGGUGU-GGGAAACCCAGACCGGGCGU | 123 |
| 43B | UGUGUGGGACAGCGG-AUC-AGGGGUGU-GGGAGCGCAUAACAUCCUACNUGCU | 124 |
| 30B | ANNNNUNUGCAUGUGUGGACAG-GGUGCAUGGGGUUGCGGGACCUUGGU | 125 |
| | UGUGUGGGACAG-GGNAUANANGGUGU-GGGA | 126 |

| | | |
|---|---|---|
| FAMILY 2 | | |
| 51A | GCAGGAGGAUAGGGAUCGGAUGGGGUAGGA | 127 |
| 53A | UGAGGAUCGGAUGGGGAGCAGGCGGAGGAA | 128 |
| 67A | GUGGAUUGGAAGGGUCUGGAGGAGGACG | 129 |
| 15B | UAGGAAUGGAUGGGGUUGGAACAGAGUUCUAAUGUGACCUCACAUGUGG | 130 |
| 77B | CAGGAAUGGAUGGGGUUGGAACAGUUCUAAUGUGACCUCACAUGCGU | 131 |
| 48B | CAGGAUAUGGAUGGGGUCCGAACCGUGUAUCAUAACAGUCAUCUCCUGGU | 132 |
| | GGAUHGGAUGGGGU | 133 |

| | | |
|---|---|---|
| FAMILY 3 | | |
| 58A | UUAACGGCUGUCCGAGGUGGCGAGUAC | 134 |
| 64A | GACUAGGCGCGACCGUGGUGGUGAGUGG | 135 |
| 50B | AGUGGCAUGGGCCUGGGAGGUGAGCUGUGUUGGGCCU | 136 |

TABLE VIII-continued

2'-NH₂ RNA LIGANDS (RANDOM REGION) TO bFGF

| | | SEQ ID NO: |
|---|---|---|
| 22B | CGUGGUUCCGUGGGUGGUGAGAUGAGACUUAAUCAGUUCGUAGACCGGU | 137 |
| | CCGUGGGUGGUGAGU | 138 |

TWO-MEMBER FAMILIES

| | | |
|---|---|---|
| 35B | NAAAUACGAGAGAGGANCAUANNUGACUGAACAUUGAUGAUUAACGAGU | 139 |
| 49B | GAGGUACGAGAGAGGAGCGUAGGUGACUGAACAUUGAUGUAUUAACGUGU | 140 |
| 47B | AGGGUGGCUGUGGGAGACCCGGUAGCACAGUGAUGUAUGAAUUCGGU | 141 |
| 73B | GAGGUGGCAGGGAGGACCCGGUGAAUCGGUAGCACAGUGAGUUCGGU | 142 |
| 6A | CGCGAGGGCUGGCGGGGUAGGAUGGGUAGA | 143 |
| 75B | CCGAGUGCUACGAGGCGUGGGGGAAACUAGUUGUGCUCUGGCCG | 144 |
| 55A | GAUUGGAAGCAGGUGUGGGGUUAGGAGGGC | 145 |
| 21B | GACCACAGUUUAAACGCCAUCAGUGGUAGGGUGUGGGUAAGGAGGGCUG | 146 |

OTHER SEQUENCES

| | | |
|---|---|---|
| 6A | CGCGAGGGCUGGCGGGGUAGGAUGGUAGA | 147 |
| 9A | UGGCCGCCGGUCUUGGGGUAUGUGUGAA | 148 |
| 52A | AGUUGGGGGGCUCGUGCGCUGCGUGGGCCUGC | 149 |
| 62A | GGGAUGGUUGGAGACCGGAGAGAUGGGAGGA | 150 |
| 69A | AAACGGGGCGAUGGAAAGUGUGGGUACGA | 151 |
| 73A | GAGGAGGAUGGAAGAGAGCGGUGUGCAGGG | 152 |
| 83A | GAGAGGGUGAAGUGGGCAGGAUGGGGUAGG | 153 |
| 8B | CUGAAAUUGCGGGUGUGGAUGCUGGGAAAGGUGGAUGGUACACGU | 154 |
| 13B | CAAUGUUUGGAGUCUGCUAAUGUGGGUUAGACGUACCGAUGGUUGC | 155 |
| 14B | ACGGGGAAGUACGAGAGCGGACUGUAAGUCUAGUGGGGUCAGUUCGGUG | 156 |
| 19B | UUCAGCGCCAUUAGUGCACGCGGUUCAACAAAAGAGGUGUUCGGUGUGUG | 157 |
| 26B | CGGAUUGUGUGUCGGGAGGGCAGUAGUUUACACUCACCGUGGUCUGCU | 158 |
| 29B | CGUGUGUGACAAUGUGCGUGGGUUGGCAGGUGUACAAAGCGUAUGGGCGUG | 159 |
| 34B | AACCGGGAGGUACGAGAGCGGGAGCGCAUAAAUAGGAAACUCCUUGCACGU | 160 |
| 36B | AGCAGUAUUGGGGGUGGUCAGCGCCUCCCCAAAACUCGCACCUUAGCCC | 161 |
| 44B | GGUUGGGUGGCAAGCGGGAGAGCAGGGUUAGGUGCGACUCAUUGGUGUG | 162 |
| 52B | GGAGGGCAGGUUCGGGGACCGACUGACCACGAGAAAUGUGCGGGU | 163 |
| 72B | CUCAGCAUCCAGGAAGGGGACUUGGGUAGGGCACCAUCGAGAUCUGGCGU | 164 |
| 78B | ACCUAGGCAUCCAGGUUGGGGAUAGCGGUUGGAGUGAAUGUGUUGUGCC | 165 |

NITROCELLULOSE-BINDING FAMILY

| | | |
|---|---|---|
| 5A | CACGGAGGAGGAGGUCAGACUUAGCGGUCA | 166 |
| 16A | UACAGGGAAGGAAGGAGNGAAUUGCAAGAUGAA | 167 |
| 17A* | AAAGUUGUGUGGAAGAACAGUGGAGGUGAA | 168 |
| 19A | UGAUGGCUGGGUAUAGAGCGUNA | 169 |
| 25A | UAGGAGGUUGGAGGAAAGCUUCACAGCCGA | 170 |
| 40A | UGAGGAGGAGGACAGGAAUUCAACAGAGU | 171 |
| 65A | GUUAGGAGGGUGGAGGUUCGGAGGUGGCAA | 172 |
| 66A | CGUCGAGUGCGAUGGAGGAGGAGGGAUGCA | 173 |
| 74A* | GGGUCAAGGACAGUGGGUGGUGGUGU | 174 |
| 75A | GGAGGAGGAGGGAUGAGAGCUCAUCAGC | 175 |
| 76A | CAAACAGGAGGGAAUGGAGGNG | 176 |
| 77A | AGGGUGGUCGGUAAGCUCGGUGGUGG | 177 |

TABLE VIII-continued

2'-NH₂ RNA LIGANDS (RANDOM REGION) TO bFGF

| | | SEQ ID NO: |
|---|---|---|
| 78A | AGGAGGGUUAAGGAGGAGAUUAAGCGUUGG | 178 |
| 81A | GUGGAGGGUACGUGGAGGGAGGGAGAGCGACA | 179 |
| 85A | AUAAUUCAAGGAGGUGGAGACAGAUGCGC | 180 |
| 86A | GAUGAGGACUCGGGGCGAGGUGGUACCA | 181 |
| 5BA | AGGUCGUGGCUGGGAUUCGUCCUCGACAUGUACAUUGUGGCUCUGGUGCC | 182 |
| 6BA | AAGUUAGUCAUCGUGCAAACUGCGAGUGCACUGCUCGGAUCC | 183 |
| 21B | GACCACAGUUUAAACGCCCAUCAGUGUGGUAGGGUGUGGGUAAGGAGGGCUG | 184 |
| 75B | CGCGAGUGCUACGAGGCGUGGGGGGUGGAAACUAGUGUGCUCUGGCCG | 185 |

TABLE IX

DISSOCIATION CONSTANTS FOR A REPRESENTATIVE SET OF HIGH-AFFINITY 2'-NH$_2$ RNA LIGANDS TO bFGF

| CLONE | Kd (nM) | SEQ ID. NO. |
|---|---|---|
| 21A | 1.3 ± 0.1 | 104 |
| 49A | 1.4 ± 0.3 | 107 |
| 53A | 1.5 ± 0.3 | 128 |
| 54A | 1.7 ± 0.3 | 108 |
| 58A | 1.4 ± 0.3 | 134 |
| 59A | 1.2 ± 0.2 | 119 |
| 22B | 2.8 ± 0.5 | 137 |
| 34B | 2.0 ± 0.4 | 160 |
| 47B | 2.9 ± 0.3 | 141 |
| 48B | 6.7 ± 1.1 | 132 |
| 52B | 2.3 ± 0.3 | 163 |
| 72B | 3.4 ± 0.5 | 164 |
| starting random RNA A | 65 ± 11 | |
| starting random RNA B | 240 ± 140 | |

TABLE X

INHIBITION OF RAT CORNEAL VASCULAR INGROWTH BY RNA LIGAND A2/C2

| Day | Group I (untreated) | Group II A2/C2 | Group III (bFGF) | Group IV (A2/C2 + bFGF) |
|---|---|---|---|---|
| 7 | 367 ± 4 | 363 ± 3 | 972 ± 72 | 623 ± 122* |
| 14 | 470 ± 57 | 388 ± 11 | 1528 ± 167 | 900 ± 80* |

Data are mean ± STD. Err.
*P<0.05 compared with Group III. (T-test, 2 Tailed)

We claim:

1. A method for identifying nucleic acid ligands to basic fibroblast growth factor (bFGF) comprising:

a) preparing a candidate mixture of nucleic acids, b) contacting the candidate mixture with bFGF, wherein nucleic acids having sequences with an increased affinity to bFGF relative to the total candidate mixture may be partitioned from the remainder of the nucleic acids in the candidate mixture, c) partitioning the increased affinity nucleic acids from the remainder of the candidate mixture, and d) amplifying the increased affinity nucleic acids to yield a mixture of nucleic acids enriched for sequences with increased affinity to bFGF, whereby nucleic acid ligands to bFGF may be identified.

2. The method of claim 1 further comprising e) repeating steps b) through d).

3. The method of claim 1 wherein said candidate mixture of nucleic acids is comprised of single stranded nucleic acids.

4. The method of claim 3 wherein said candidate mixture of nucleic acids is comprised of RNA.

5. The method of claim 4 wherein said candidate mixture of nucleic acids is comprised of RNA wherein all pyrimidines are 2'-deoxy-2-NH$_2$ pyrimidines.

6. A method for selecting a nucleic acid ligand which inhibits the binding of bFGF to its receptor, which comprises the additional step of screening nucleic acid ligands to bFGF identified by the method of claim 1 for their ability to inhibit the binding of bFGF to its receptor.

* * * * *